US012708894B2

(12) United States Patent
Simanzhenkov et al.

(10) Patent No.: US 12,708,894 B2
(45) Date of Patent: Aug. 18, 2026

(54) MOLYBDENUM-VANADIUM-IRON- AND/OR MOLYBDENUM-VANADIUM-ALUMINIUM-BASED OXIDATIVE DEHYDROGENATION CATALYST MATERIALS

(71) Applicant: NOVA Chemicals (International) S.A., Fribourg (CH)

(72) Inventors: Vasily Simanzhenkov, Calgary (CA); Yoonhee Kim, Calgary (CA); Xiaoliang Gao, Calgary (CA); David Sullivan, Calgary (CA); Marie Barnes, Calgary (CA); Elena Sebastiao, Calgary (CA)

(73) Assignee: NOVA Chemicals (International) S.A., Fribourg (CH)

(*) Notice: Subject to any disclaimer, the term of this patent is extended or adjusted under 35 U.S.C. 154(b) by 161 days.

(21) Appl. No.: 18/618,493

(22) Filed: Mar. 27, 2024

(65) Prior Publication Data

US 2024/0253021 A1 Aug. 1, 2024

Related U.S. Application Data

(62) Division of application No. 17/634,037, filed as application No. PCT/IB2020/058178 on Sep. 2, 2020, now Pat. No. 11,998,897.

(Continued)

(51) Int. Cl.

*B01J 23/881* (2006.01)
*B01J 23/887* (2006.01)

(Continued)

(52) U.S. Cl.

CPC ......... *B01J 23/881* (2013.01); *B01J 23/8877* (2013.01); *C07C 5/48* (2013.01);

(Continued)

(58) Field of Classification Search

CPC .. B01J 23/881; B01J 23/8877; B01J 2523/00; B01J 2523/31; B01J 2523/55;

(Continued)

(56) References Cited

U.S. PATENT DOCUMENTS

| | | | |
|---|---|---|---|
| 3,358,020 A | 12/1967 | Antonin | |
| 3,567,772 A | 3/1971 | Yanagita et al. | |

(Continued)

FOREIGN PATENT DOCUMENTS

| | | | |
|---|---|---|---|
| CN | 106311214 A * | 1/2017 | ............. C07C 5/367 |
| CN | 106693981 | 5/2017 | |

(Continued)

OTHER PUBLICATIONS

International Preliminary Report on Patentability in International Appln. No. PCT/IB2020/058178, mailed on Mar. 8, 2022, 19 pages.

(Continued)

*Primary Examiner* — Jun Li

(74) *Attorney, Agent, or Firm* — Fish & Richardson P.C.

(57) ABSTRACT

This document relates to oxidative dehydrogenation catalyst materials that include molybdenum, vanadium, oxygen, and iron; oxidative dehydrogenation catalyst materials that include molybdenum, vanadium, oxygen, and aluminum; and oxidative dehydrogenation catalyst materials that include molybdenum, vanadium, oxygen, iron, and aluminum.

13 Claims, 17 Drawing Sheets

Related U.S. Application Data

(60) Provisional application No. 62/970,378, filed on Feb. 5, 2020, provisional application No. 62/895,536, filed on Sep. 4, 2019.

(51) Int. Cl.
*C07C 5/48* (2006.01)
*B01J 35/80* (2024.01)

(52) U.S. Cl.
CPC ........... *B01J 35/80* (2024.01); *B01J 2235/00* (2024.01); *B01J 2235/10* (2024.01); *B01J 2235/15* (2024.01); *B01J 2235/30* (2024.01); *B01J 2523/31* (2013.01); *B01J 2523/55* (2013.01); *B01J 2523/68* (2013.01); *B01J 2523/842* (2013.01)

(58) Field of Classification Search
CPC .... B01J 2523/68; C07C 5/48; C07C 2521/02; C07C 2521/04; C07C 11/04
See application file for complete search history.

(56) References Cited

U.S. PATENT DOCUMENTS

| | | | | |
|---|---|---|---|---|
| 4,217,309 | A | 8/1980 | Umemura et al. | |
| 4,250,346 | A | 2/1981 | Young et al. | |
| 4,339,394 | A | 7/1982 | Grasselli et al. | |
| 4,435,607 | A | 3/1984 | Imai | |
| 5,118,868 | A * | 6/1992 | Sarup | B01J 35/58 568/474 |
| 8,105,971 | B2 | 1/2012 | Gaffney et al. | |
| 9,731,285 | B2 | 8/2017 | Tateno et al. | |
| 11,111,194 | B2 | 9/2021 | Simanzhenkov et al. | |
| 11,306,044 | B2 | 4/2022 | Olayiwola et al. | |
| 11,413,604 | B2 | 8/2022 | Simanzhenkov et al. | |
| 2002/0183580 | A1 * | 12/2002 | Dyroff | B01J 35/651 585/654 |
| 2003/0208085 | A1 | 11/2003 | Gaffney et al. | |
| 2009/0292153 | A1 | 11/2009 | Cai | |
| 2010/0256432 | A1 | 10/2010 | Arnold et al. | |
| 2019/0039050 | A1 | 2/2019 | Gao et al. | |
| 2019/0218161 | A1 | 7/2019 | Simanzhenkov et al. | |
| 2020/0038843 | A1 | 2/2020 | Simanzhenkov et al. | |
| 2022/0288564 | A1 | 9/2022 | Simanzhenkov et al. | |
| 2022/0305467 | A1 | 9/2022 | Simanzhenkov et al. | |

FOREIGN PATENT DOCUMENTS

| | | | | |
|---|---|---|---|---|
| CN | 107970954 | | 5/2018 | |
| DE | 102009014541 | | 9/2010 | |
| GB | 1538107 | | 1/1979 | |
| RU | 2692807 | C2 * | 6/2019 | B01J 23/002 |
| WO | WO-2019163707 | A1 * | 8/2019 | C07C 47/22 |
| WO | WO 2020/016828 | | 1/2020 | |
| WO | WO 2020/026193 | | 2/2020 | |
| WO | WO 2021/044316 | | 3/2021 | |

OTHER PUBLICATIONS

International Search Report and Written Opinion in International Appln. No. PCT/IB2020/058178, mailed on Apr. 7, 2021, 28 pages.

O'Connor et al., "Application of the Rietveld Refinement Procedure in Assaying Powdered Mixtures," Powder Diffraction, Mar. 1988, 3(1):2-6.

Ueda et al., "Key aspects of crystalline Mo-VO-based catalysts active in the selective oxidation of propane," Research on Chemical Intermediates, Mar. 2006, 32:217-233.

* cited by examiner

| Catalyst Material | x 15,000 | x 10,000 | x 5,000 |
| --- | --- | --- | --- |
| 1.6 | n/a |  |  |

| Catalyst Material | x 15,000 | x 10,000 | x 5,000 |
| --- | --- | --- | --- |
| 3.16 |  |  | n/a |
| 3.15 | n/a |  |  |
| 3.12 | n/a |  |  |
| 3.18 |  |  |  |

| Catalyst Material | x 15,000 | x 10,000 | x 5,000 |
|---|---|---|---|
| 4.2 | n/a | n/a |  |
| 4.1 | n/a | n/a |  |
| 4.6 |  |  |  |
| 4.9 |  |  |  |
| 4.7 |  |  |  |
| 4.8 |  |  |  |

MOLYBDENUM-VANADIUM-IRON- AND/OR MOLYBDENUM-VANADIUM-ALUMINIUM-BASED OXIDATIVE DEHYDROGENATION CATALYST MATERIALS

CROSS-REFERENCE TO RELATED APPLICATION

This application is a divisional and claims the benefit of priority to U.S. application Ser. No. 17/634,037, filed on Feb. 9, 2022, which is a National Stage Application under 35 U.S.C. § 371 and claims the benefit of International Application No. PCT/IB2020/058178, filed Sep. 2, 2020, which claims priority to U.S. Ser. No. 62/895,536, filed on Sep. 4, 2019 and U.S. Ser. No. 62/970,378, filed Feb. 5, 2020. The disclosure of the prior applications is considered part of and is incorporated by reference in the disclosure of this application.

TECHNICAL FIELD

This document relates to oxidative dehydrogenation catalyst materials of alkanes such as ethane.

SUMMARY OF INVENTION

Provided herein is an oxidative dehydrogenation catalyst material that includes molybdenum (Mo), vanadium (V), oxygen (O), and iron (Fe). The molar ratio of molybdenum to vanadium is from 1:0.25 to 1:0.50. The molar ratio of molybdenum to iron is from 1:0.25 to 1:5.5. Further, oxygen is present at least in an amount to satisfy the valency of any present metal oxides.

In some embodiments, the molar ratio of molybdenum to vanadium is from 1:0.30 to 1:0.45. In some embodiments, the molar ratio of molybdenum to vanadium is from 1:0.30 to 1:0.35. In some embodiments, the molar ratio of molybdenum to vanadium is from 1:0.35 to 1:0.45.

In some embodiments, the molar ratio of molybdenum to iron is from 1:3 to 1:5.5. In some embodiments, the molar ratio of molybdenum to iron is from 1:4.25 to 1:4.75. In some embodiments, the molar ratio of molybdenum to iron is from 1:4.45 to 1:4.55. In some embodiments, the molar ratio of molybdenum to iron is from 1:0.1 to 1:1. In some embodiments, the molar ratio of molybdenum to iron is from 1:0.25 to 1:0.75. In some embodiments, the molar ratio of molybdenum to iron is from 1:0.4 to about 1:0.6. In some embodiments, the molar ratio of molybdenum to iron is about 1:0.4. In some embodiments, the molar ratio of molybdenum to iron is about 1:0.6. In some embodiments, the molar ratio of molybdenum to iron is from 1:1.3 to 1:2.2. In some embodiments, the molar ratio of molybdenum to iron is from 1:1.6 to 1:2.0. In some embodiments, the molar ratio of molybdenum to iron is from 1:1.80 to 1:1.90.

In some embodiments, the catalyst material has a 35% conversion temperature from about 300° C. to about 400° C. In some embodiments, the catalyst material has a 35% conversion temperature from about 300° C. to about 350° C. In some embodiments, the catalyst material has a 35% conversion temperature from about 315° C. to about 335° C.

In some embodiments, the catalyst material has a selectivity to ethylene from about 65% to about 99%. In some embodiments, the catalyst material has a selectivity to ethylene from about 75% to about 95%.

In some embodiments, at least a portion of the iron in the catalyst material is present as Fe(III).

In some embodiments, at least a portion of the iron in the catalyst material is present as amorphous iron.

In some embodiments, at least a portion of the iron in the catalyst material is present as an iron oxide, an iron oxide hydroxide, or a combination thereof. In some embodiments, the iron oxide includes an iron oxide selected from hematite ($\alpha$-$Fe_2O_3$), maghemite ($\gamma$-$Fe_2O_3$), magnetite ($Fe_3O_4$), or a combination thereof. In some embodiments, the iron oxide includes hematite. In some embodiments, the iron oxide hydroxide includes an iron oxide hydroxide selected from a goethite, an akageneite, a lepidocrocite, or a combination thereof. In some embodiments, the iron oxide hydroxide includes a goethite.

In some embodiments, at least a portion of the iron in the catalyst material is present as a goethite and at least a portion of the iron in the catalyst material is present a hematite.

In some embodiments, the catalyst material is prepared by a method that includes providing a catalyst including molybdenum, vanadium, and oxygen; preparing an aqueous mixture including the catalyst, an iron compound, and a water; removing a substantial amount of the water from the mixture to provide a precatalyst material; and heating the precatalyst material to provide the catalyst material.

In some embodiments, the molar ratio of molybdenum to vanadium in the catalyst is from 1:0.25 to 1:0.5. In some embodiments, the molar ratio of molybdenum to vanadium in the catalyst is from 1:0.3 to 1:0.49.

In some embodiments, the catalyst includes a mixed metal oxide having the empirical formula:

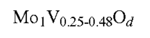

wherein d is a number to satisfy the valence of the oxide.

In some embodiments, providing the catalyst including molybdenum, vanadium, and oxygen includes preparing an aqueous mixture of molybdenum and vanadium; hydrothermally reacting the aqueous mixture to form a precalcined catalyst; and calcining the precalcined catalyst to provide the catalyst including molybdenum, vanadium, and oxygen.

In some embodiments, the aqueous mixture of molybdenum and vanadium is prepared by combining an aqueous mixture including molybdenum and an aqueous mixture including vanadium. The aqueous mixture including molybdenum can be prepared from at least $(NH_4)_6Mo_7O_{24}\cdot4H_2O$ and a first water. The aqueous mixture including vanadium can be prepared from at least $VOSO_4\cdot XH_2O$ and a second water. In some embodiments, the molar ratio of $(NH_4)_6Mo_7O_{24}\cdot4H_2O$ to $VOSO_4\cdot XH_2O$ is from 1:1.5 to 1:2. In some embodiments, the molar ratio of $(NH_4)_6Mo_7O_{24}\cdot4H_2O$ to $VOSO_4\cdot XH_2O$ is about 1:1.75. In some embodiments, the concentration of molybdenum in the aqueous mixture of molybdenum and vanadium is less than $6.3\times10^{-1}$ mol/L. In some embodiments, the concentration of molybdenum in the aqueous mixture of molybdenum and vanadium is from $2.09\times10^{-1}$ mol/L to $3.13\times10^{-1}$ mol/L. In some embodiments, the concentration of vanadium in the aqueous mixture of molybdenum and vanadium is less than $15.60\times10^{-2}$ mol/L. In some embodiments, the concentration of vanadium in the aqueous mixture of molybdenum and vanadium is from $5.20\times10^{-2}$ mol/L to $7.80\times10^{-2}$ mol/L.

In some embodiments, providing the catalyst further includes contacting the aqueous mixture of molybdenum and vanadium with a templating agent.

In some embodiments, the templating agent includes a surfactant, a catalyst seed, or a combination thereof. In some embodiments, the catalyst seed includes a catalyst seed selected from a catalyst seed including molybdenum and vanadium; a catalyst seed including molybdenum, vanadium, tellurium, and niobium, or a combination thereof. In some embodiments, the weight ratio of the catalyst seed to the $(NH_4)_6Mo_7O_{24}\cdot 4H_2O$ used to prepare the aqueous mixture is about 0.5:100 to about 4.0:100.

In some embodiments, the templating agent includes a surfactant. In some embodiments, the surfactant molar loading is from about 0.005 to about 0.2.

In some embodiments, the first and the second water are selected from a distilled water, a deionized water, a demineralized water, a mineral water, or a combination thereof. In some embodiments, the first and second water include a distilled water.

In some embodiments, hydrothermally reacting the aqueous mixture to form a precalcined catalyst includes heating the aqueous mixture of molybdenum and vanadium at a temperature of about 150° C. to about 300° C. In some embodiments, hydrothermally reacting the aqueous mixture to form a precalcined catalyst includes heating the aqueous mixture of molybdenum and vanadium at a temperature of about 200° C. to about 250° C. In some embodiments, hydrothermally reacting the aqueous mixture to form a precalcined catalyst includes heating the aqueous mixture of molybdenum and vanadium at a temperature of about 220° C. to about 230° C.

In some embodiments, hydrothermally reacting the aqueous mixture to form a precalcined catalyst includes contacting the aqueous mixture with a glass liner, a steel liner, or a Teflon liner. In some embodiments, hydrothermally reacting the aqueous mixture to form a precalcined catalyst includes contacting the aqueous mixture with a glass liner. In some embodiments, hydrothermally reacting the aqueous mixture to form a precalcined catalyst includes contacting the aqueous mixture with a Teflon liner.

In some embodiments, providing the catalyst further includes treating the precalcined catalyst in air from 250° C. to 300° C. In some embodiments, providing the catalyst further includes treating the precalcined catalyst in air at about 280° C.

In some embodiments, the precalcined catalyst is calcined at about 300° C. to about 500° C. In some embodiments, the precalcined catalyst is calcined at about 375° C. to about 425° C.

In some embodiments, the precalcined catalyst is calcined at about 300° C. to about 500° C. for about 1 hour to about 24 hours. In some embodiments, the precalcined catalyst is calcined at about 375° C. to about 425° C. for about 1 hour to about 4 hours.

In some embodiments, the precalcined catalyst is calcined in air, an inert atmosphere, or a combination thereof.

In some embodiments, the precalcined catalyst is calcined in an inert atmosphere. In some embodiments, wherein the inert atmosphere includes nitrogen.

In some embodiments, the iron compound in the mixture including the catalyst, the iron compound, and the water includes an Fe(III) compound.

In some embodiments, the iron compound in the mixture including the catalyst, the iron compound, and the water includes an iron compound selected from an iron oxide, an iron oxide hydroxide, or a combination thereof. In some embodiments, the iron oxide includes an iron oxide selected from hematite ($\alpha$-$Fe_2O_3$), maghemite ($\gamma$-$Fe_2O_3$), magnetite ($Fe_3O_4$), or a combination thereof. In some embodiments, the iron oxide includes hematite. In some embodiments, the iron oxide hydroxide includes an iron oxide hydroxide selected from a goethite, an akageneite, a lepidocrocite, or a combination thereof. In some embodiments, the iron oxide hydroxide includes a goethite.

In some embodiments, removing a substantial amount of water from the mixture including the catalyst, the iron compound, and the water to provide a precatalyst material includes heating the aqueous mixture at a temperature from about 50° C. to about 100° C. In some embodiments, removing a substantial amount of water from the aqueous mixture including the catalyst, the iron compound, and the water to provide a precatalyst material includes heating the aqueous mixture at a temperature of about 80° C.

In some embodiments, removing a substantial amount of water from the aqueous mixture including the catalyst, the iron compound, and the water to provide a precatalyst material includes removing from about 50 wt. % to about 99 wt. % of the added water.

In some embodiments, the precatalyst material to provide the catalyst material includes heating the precatalyst material at a temperature from about 300° C. to about 500° C. In some embodiments, heating the precatalyst material to provide the catalyst material includes heating the precatalyst material at a temperature from about 350° C. to about 450° C.

In some embodiments, heating the precatalyst material to provide the catalyst material includes heating the precatalyst material in the presence of air, an oxidizing atmosphere, an inert atmosphere, or a combination thereof. In some embodiments, heating the precatalyst material to provide the catalyst material includes heating the precatalyst material the presence of air.

In some embodiments, the catalyst material is treated with a gas including ethane. In some embodiments, the gas further includes oxygen. In some embodiments, the gas further includes ethylene. In some embodiments, the catalyst material is treated with the gas including ethane at a temperature from about 100° C. to about 500° C. In some embodiments, the catalyst material is treated with the gas including ethane for about 18 hours to about 72 hours.

Also provided in this disclosure is an oxidative dehydrogenation catalyst material that molybdenum, vanadium, oxygen, and aluminum. The molar ratio of molybdenum to vanadium is from 1:0.1 to 1:0.50. The molar ratio of molybdenum to aluminum is from 1:1.5 to 1:6.5. Oxygen is present at least in an amount to satisfy the valency of any present metal oxides.

In some embodiments, the molar ratio of molybdenum to vanadium in the catalyst material is from 1:0.25 to 1:0.50. In some embodiments, the molar ratio of molybdenum to vanadium is from 1:0.30 to 1:0.45. In some embodiments, the molar ratio of molybdenum to vanadium is about 1:0.30 to about 1:0.35. In some embodiments, the molar ratio of molybdenum to vanadium is about 1:0.35 to about 1:0.45.

In some embodiments, the molar ratio of molybdenum to aluminum is from 1:3.0 to 1:6.5. In some embodiments, the molar ratio of molybdenum to aluminum is from 1:3.25 to 1:5.5.5. In some embodiments, the molar ratio of molybdenum to aluminum is from 1:3.5 to 1:4.1. In some embodiments, the molar ratio of molybdenum to aluminum is from 1:4.95 to 1:5.05. In some embodiments, the molar ratio of molybdenum to aluminum is from 1:4.55 to 1:4.65. In some embodiments, the molar ratio of molybdenum to aluminum is from 1:1.5 to 1:3.5. In some embodiments, the molar ratio of molybdenum to aluminum is from 1:2.0 to 1:2.2. In some embodiments, the molar ratio of molybdenum to aluminum is from 1:2.9 to 1:3.1.

In some embodiments, the catalyst material has a 35% conversion temperature from about 300° C. to about 400° C. In some embodiments, the catalyst material has a 35% conversion temperature from about 300° C. to about 350° C. In some embodiments, the catalyst material has a 35% conversion temperature from about 315° C. to about 335° C.

In some embodiments, the catalyst material has a selectivity to ethylene from about 65% to 99%. In some embodiments, the catalyst material has a selectivity to ethylene from about 75% to 95%.

In some embodiments, at least a portion of the aluminum in the catalyst material is present as an aluminum oxide. In some embodiments, the aluminum oxide is an aluminum oxide hydroxide. In some embodiments, the aluminum oxide hydroxide includes an aluminum oxide hydroxide selected from a gibbsite, a bayerite, a boehmite, or a combination thereof. In some embodiments, the aluminum oxide hydroxide includes a boehmite.

In some embodiments, at least a portion of the aluminum in the catalyst material is present as gamma alumina.

In some embodiments, the catalyst material is prepared by a method that includes providing a catalyst including molybdenum, vanadium, and oxygen; preparing an aqueous mixture including the catalyst, an aluminum compound, and a water; removing a substantial amount of the water from the mixture to provide a precatalyst material; and heating the precatalyst material to provide the catalyst material.

In some embodiments, the molar ratio of molybdenum to vanadium in the catalyst is from 1:0.25 to 1:0.5. In some embodiments, the molar ratio of molybdenum to vanadium in the catalyst is from 1:0.3 to 1:0.49.

In some embodiments, the catalyst includes a mixed metal oxide having the empirical formula:

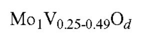

$$Mo_1V_{0.25\text{-}0.49}O_d$$

wherein d is a number to satisfy the valence of the oxide.

In some embodiments, providing the catalyst including molybdenum, vanadium, and oxygen includes preparing an aqueous mixture of molybdenum and vanadium; hydrothermally reacting the aqueous mixture to form a precalcined catalyst; and calcining the precalcined catalyst to provide the catalyst including molybdenum, vanadium, and oxygen.

In some embodiments, the aqueous mixture of molybdenum and vanadium is prepared by combining an aqueous mixture including molybdenum and an aqueous mixture including vanadium and wherein the aqueous mixture including molybdenum is prepared from at least $(NH_4)_6Mo_7O_{24}{\cdot}4H_2O$ and a first water, and the aqueous mixture including vanadium is prepared from at least $VOSO_4{\cdot}XH_2O$ and a second water. In some embodiments, the molar ratio of $(NH_4)_6Mo_7O_{24}{\cdot}4H_2O$ to $VOSO_4{\cdot}XH_2O$ is from 1:1.5 to 1:2. In some embodiments, the molar ratio of $(NH_4)_6Mo_7O_{24}{\cdot}4H_2O$ to $VOSO_4{\cdot}XH_2O$ is about 1:1.75. In some embodiments, the concentration of molybdenum in the aqueous mixture of molybdenum and vanadium is less than $6.3\times10^{-1}$ mol/L. In some embodiments, the concentration of molybdenum in the aqueous mixture of molybdenum and vanadium is from $2.09\times10^{-1}$ mol/L to $3.13\times10^{-1}$ mol/L. In some embodiments, the concentration of vanadium in the aqueous mixture of molybdenum and vanadium is less than $15.60\times10^{-2}$ mol/L. In some embodiments, the concentration of vanadium in the aqueous mixture of molybdenum and vanadium is from $5.20\times10^{-2}$ mol/L to $7.80\times10^{-2}$ mol/L.

In some embodiments, providing the catalyst further includes contacting the aqueous mixture of molybdenum and vanadium with a templating agent.

In some embodiments, the templating agent includes a surfactant, a catalyst seed, or a combination thereof. In some embodiments, the catalyst seed includes a catalyst seed selected from a catalyst seed including molybdenum and vanadium; a catalyst seed including molybdenum, vanadium, tellurium, and niobium, or a combination thereof. In some embodiments, the weight ratio of the catalyst seed to the $(NH_4)_6Mo_7O_{24}{\cdot}4H_2O$ used to prepare the aqueous mixture is about 0.5:100 to about 4.0:100.

In some embodiments, the templating agent includes a surfactant. In some embodiments, the surfactant molar loading is from about 0.005 to about 0.2.

In some embodiments, the first and the second water are selected from a distilled water, a deionized water, a demineralized water, a mineral water, or a combination thereof. In some embodiments, the first and second water include a distilled water.

In some embodiments, hydrothermally reacting the aqueous mixture to form a precalcined catalyst includes heating the aqueous mixture of molybdenum and vanadium at a temperature of about 150° C. to about 300° C. In some embodiments, hydrothermally reacting the aqueous mixture to form a precalcined catalyst includes heating the aqueous mixture of molybdenum and vanadium at a temperature of about 200° C. to about 250° C. In some embodiments, hydrothermally reacting the aqueous mixture to form a precalcined catalyst includes heating the aqueous mixture of molybdenum and vanadium at a temperature of about 220° C. to about 230° C.

In some embodiments, hydrothermally reacting the aqueous mixture to form a precalcined catalyst includes contacting the aqueous mixture with a glass liner, a steel liner, or a Teflon liner. In some embodiments, hydrothermally reacting the aqueous mixture to form a precalcined catalyst includes contacting the aqueous mixture with a glass liner. In some embodiments, hydrothermally reacting the aqueous mixture to form a precalcined catalyst includes contacting the aqueous mixture with a Teflon liner.

In some embodiments, providing the catalyst further includes treating the precalcined catalyst in air from 250° C. to 300° C. In some embodiments, providing the catalyst further includes treating the precalcined catalyst in air at about 280° C.

In some embodiments, the precalcined catalyst is calcined at about 300° C. to about 500° C. In some embodiments, the precalcined catalyst is calcined at about 375° C. to about 425° C. In some embodiments, the precalcined catalyst is calcined at about 300° C. to about 500° C. for about 1 hour to about 24 hours. In some embodiments, the precalcined catalyst is calcined at about 375° C. to about 425° C. for about 1 hour to about 4 hours.

In some embodiments, the precalcined catalyst is calcined in air, an inert atmosphere, or a combination thereof. In some embodiments, the precalcined catalyst is calcined in an inert atmosphere. In some embodiments, the inert atmosphere includes nitrogen.

In some embodiments, the aluminum compound in the aqueous mixture including the catalyst, the aluminum compound, and the water includes an aluminum oxide. In some embodiments, the aluminum oxide includes an aluminum oxide hydroxide. In some embodiments, the aluminum oxide hydroxide includes an aluminum oxide hydroxide selected from a gibbsite, a bayerite, a boehmite, or a combination thereof. In some embodiments, the aluminum oxide hydroxide includes a boehmite.

In some embodiments, removing a substantial amount of water from the mixture including the catalyst, the aluminum compound, and the water to provide a precatalyst material includes heating the aqueous mixture at a temperature from about 50° C. to about 100° C. In some embodiments, removing a substantial amount of water from the mixture including the catalyst, the aluminum compound, and the water to provide a precatalyst material includes heating the aqueous mixture at a temperature of about 80° C.

In some embodiments, removing a substantial amount of water from the aqueous mixture including the catalyst, the aluminum compound, and the water to provide a precatalyst material includes removing from about 50 wt. % to about 99 wt. % of the water.

In some embodiments, heating the precatalyst material to provide the catalyst material includes heating the precatalyst material at a temperature from about 300° C. to about 500° C. In some embodiments, heating the precatalyst material to provide the catalyst material includes heating the precatalyst material at a temperature from about 350° C. to about 450° C.

In some embodiments, heating the precatalyst material to provide the catalyst material includes heating the precatalyst material in air.

In some embodiments, the catalyst material is treated with a gas including ethane. In some embodiments, the gas further includes oxygen. In some embodiments, the gas further includes ethylene.

In some embodiments, the catalyst material is treated with the gas including ethane at a temperature from about 100° C. to about 500° C.

In some embodiments, the catalyst material is treated with the gas including ethane for about 18 hours to about 72 hours.

Also provided in this disclosure is an oxidative dehydrogenation catalyst material that includes molybdenum, vanadium, oxygen, aluminum, and iron. The molar ratio of molybdenum to vanadium is from 1:0.1 to 1:0.5. The molar ratio of molybdenum to aluminum is from 1:1.5 to 1:6.0. The molar ratio of molybdenum to iron is from 1:0.25 to 5:5. Oxygen is present at least in an amount to satisfy the valency of any present metal oxides.

In some embodiments, the molar ratio of molybdenum to vanadium is from 1:0.30 to 1:0.45. In some embodiments, the molar ratio of molybdenum to vanadium is from 1:0.30 to 1:0.35. In some embodiments, the molar ratio of molybdenum to vanadium is from 1:0.35 to 1:0.45.

In some embodiments, the molar ratio of molybdenum to iron is from 1:0.1 to 1:1, and the molar ratio of molybdenum to aluminum is from 1:3.5 to 1:5.5.

In some embodiments, the molar ratio of molybdenum to iron is from 1:0.25 to 1:0.75, and the molar ratio of molybdenum to aluminum is from 1:3.75 to 1:5.25.

In some embodiments, the molar ratio of molybdenum to iron is from 1:0.35 to 1:0.65, and the molar ratio of molybdenum to aluminum is from 1:3.75 to 1:5.25.

In some embodiments, the molar ratio of molybdenum to iron is from about 1:0.35 to about 1:0.45, and the molar ratio of molybdenum to aluminum is from 1:3.9 to 1:4.0.

In some embodiments, the molar ratio of molybdenum to iron is about 1:0.55 to about 0:65, and the molar ratio of molybdenum to aluminum is from 1:4.95 to 1:5.05.

In some embodiments, the molar ratio of molybdenum to iron is from 1:1.3 to 1:2.2, and the molar ratio of molybdenum to aluminum is from 1:2.0 to 1:4.0.

In some embodiments, the molar ratio of molybdenum to iron is from 1:1.6 to 1:2.0, and the molar ratio of molybdenum to aluminum is from 1:2.5 to 1:3.5.

In some embodiments, the molar ratio of molybdenum to iron is from about 1:1.80 to about 1:1.90, and the molar ratio of molybdenum to aluminum is from 1:2.9 to 1:3.1.

In some embodiments, the catalyst material has a 35% conversion temperature from about 300° C. to about 400° C. In some embodiments, the catalyst material has a 35% conversion temperature from about 300° C. to about 350° C. In some embodiments, the catalyst material has a 35% conversion temperature from about 315° C. to about 335° C.

In some embodiments, the catalyst material has a selectivity to ethylene from about 65% to 99%. In some embodiments, the catalyst material has a selectivity to ethylene from about 75% to 95%.

In some embodiments, at least a portion of the iron in the catalyst material is present as Fe(III).

In some embodiments, at least a portion of the iron in the catalyst material is present as amorphous iron.

In some embodiments, at least a portion of the iron in the catalyst material is present as an iron oxide, an iron oxide hydroxide, or a combination thereof. In some embodiments, the iron oxide includes an iron oxide selected from hematite ($\alpha$-$Fe_2O_3$), maghemite ($\gamma$-$Fe_2O_3$), magnetite ($Fe_3O_4$), or a combination thereof. In some embodiments, the iron oxide includes a hematite. In some embodiments, iron oxide hydroxide includes an iron oxide hydroxide selected from a goethite, an akageneite, a lepidocrocite, or a combination thereof. In some embodiments, the iron oxide hydroxide includes a goethite.

In some embodiments, at least a portion of the iron in the catalyst material is present as a goethite and at least a portion of the iron in the catalyst material is present a hematite.

In some embodiments, at least a portion of the aluminum in the catalyst material is present as an aluminum oxide. In some embodiments, the aluminum oxide includes an aluminum oxide hydroxide. In some embodiments, the aluminum oxide hydroxide includes an aluminum oxide hydroxide selected from a gibbsite, a bayerite, a boehmite, or a combination thereof. In some embodiments, the aluminum oxide hydroxide includes a boehmite.

In some embodiments, at least a portion of the aluminum in the catalyst material is present as a gamma alumina.

In some embodiments, the catalyst material is prepared by a method that includes providing a catalyst including molybdenum, vanadium, and oxygen; preparing an aqueous mixture including the catalyst, an iron compound, an aluminum compound, and a water; removing a substantial amount of the water from the aqueous mixture to provide a precatalyst material; and heating the precatalyst material to provide the catalyst material.

In some embodiments, the molar ratio of molybdenum to vanadium in the catalyst is from 1:0.25 to 1:0.5. In some embodiments, the molar ratio of molybdenum to vanadium in the catalyst is from 1:0.3 to 1:0.49.

In some embodiments, the catalyst includes a mixed metal oxide having the empirical formula:

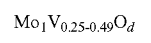

$$Mo_1V_{0.25\text{-}0.49}O_d$$

wherein d is a number to satisfy the valence of the oxide.

In some embodiments, providing the catalyst including molybdenum, vanadium, and oxygen includes preparing an aqueous mixture of molybdenum and vanadium; hydrothermally reacting the aqueous mixture to form a precalcined catalyst; and calcining the precalcined catalyst to provide the catalyst including molybdenum, vanadium, and oxygen.

In some embodiments, the aqueous mixture of molybdenum and vanadium is prepared by combining an aqueous mixture including molybdenum and an aqueous mixture including vanadium and wherein the aqueous mixture including molybdenum is prepared from at least $(NH_4)_6Mo_7O_{24}\cdot 4H_2O$ and a first water, and the aqueous mixture including vanadium is prepared from at least $VOSO_4\cdot XH_2O$ and a second water. In some embodiments, the molar ratio of $(NH_4)_6Mo_7O_{24}\cdot 4H_2O$ to $VOSO_4\cdot XH_2O$ is from 1:1.5 to 1:2. In some embodiments, the molar ratio of $(NH_4)_6Mo_7O_{24}\cdot 4H_2O$ to $VOSO_4\cdot XH_2O$ is about 1:1.75. In some embodiments, the concentration of molybdenum in the aqueous mixture of molybdenum and vanadium is less than $6.3\times 10^{-1}$ mol/L. In some embodiments, the concentration of molybdenum in the aqueous mixture of molybdenum and vanadium is from $2.09\times 10^{-1}$ mol/L to $3.13\times 10^{-1}$ mol/L. In some embodiments, the concentration of vanadium in the aqueous mixture of molybdenum and vanadium is less than $15.60\times 10^{-2}$ mol/L. In some embodiments, the concentration of vanadium in the aqueous mixture of molybdenum and vanadium is from $5.20\times 10^{-2}$ mol/L to $7.80\times 10^{-2}$ mol/L.

In some embodiments, providing the catalyst further includes contacting the aqueous mixture of molybdenum and vanadium with a templating agent. In some embodiments, the templating agent includes a surfactant, a catalyst seed, or a combination thereof. In some embodiments, the catalyst seed includes a catalyst seed selected from a catalyst seed including molybdenum and vanadium; a catalyst seed including molybdenum, vanadium, tellurium, and niobium, or a combination thereof. In some embodiments, the weight ratio of the catalyst seed to the $(NH_4)_6Mo_7O_{24}\cdot 4H_2O$ used to prepare the aqueous mixture is about 0.5:100 to about 4.0:100. In some embodiments, the templating agent includes a surfactant. In some embodiments, the surfactant molar loading is from about 0.005 to about 0.2.

In some embodiments, the first and the second water are selected from a distilled water, a deionized water, a demineralized water, a mineral water, or a combination thereof. In some embodiments, the first and second water include a distilled water.

In some embodiments, hydrothermally reacting the aqueous mixture to form a precalcined catalyst includes heating the aqueous mixture of molybdenum and vanadium at a temperature from about 150° C. to about 300° C. In some embodiments, hydrothermally reacting the aqueous mixture to form a precalcined catalyst includes heating the aqueous mixture of molybdenum and vanadium at a temperature of about 200° C. to about 250° C. In some embodiments, hydrothermally reacting the aqueous mixture to form a precalcined catalyst includes heating the aqueous mixture of molybdenum and vanadium at a temperature of about 220° C. to about 230° C.

In some embodiments, hydrothermally reacting the aqueous mixture to form a precalcined catalyst includes contacting the aqueous mixture with a glass liner, a steel liner, or a Teflon liner. In some embodiments, hydrothermally reacting the aqueous mixture to form a precalcined catalyst includes contacting the aqueous mixture with a glass liner. In some embodiments, hydrothermally reacting the aqueous mixture to form a precalcined catalyst includes contacting the aqueous mixture with a Teflon liner.

In some embodiments, providing the catalyst further includes treating the precalcined catalyst in air from 250° C. to 300° C. In some embodiments, providing the catalyst further includes treating the precalcined catalyst in air at about 280° C.

In some embodiments, the precalcined catalyst is calcined at about 300° C. to about 500° C. In some embodiments, the precalcined catalyst is calcined at about 375° C. to about 425° C.

In some embodiments, the precalcined catalyst is calcined at about 300° C. to about 500° C. for about 1 hour to about 24 hours. In some embodiments, the precalcined catalyst is calcined at about 375° C. to about 425° C. for about 1 hour to about 4 hours.

In some embodiments, the precalcined catalyst is calcined in air, an inert atmosphere, or a combination thereof. In some embodiments, the precalcined catalyst is calcined in an inert atmosphere. In some embodiments, the inert atmosphere includes nitrogen.

In some embodiments, the iron compound in the aqueous mixture including the catalyst, the iron compound, the alumina compound, and the water includes an Fe(III) compound. In some embodiments, the iron compound in the aqueous mixture including the catalyst, the iron compound, and the water includes an iron compound selected from an iron oxide, an iron oxide hydroxide, or a combination thereof. In some embodiments, the iron oxide includes an iron oxide selected from a hematite ($\alpha$-$Fe_2O_3$), maghemite ($\gamma$-$Fe_2O_3$), magnetite ($Fe_3O_4$), or a combination thereof. In some embodiments, the iron oxide includes hematite. In some embodiments, the iron oxide hydroxide includes an iron oxide hydroxide selected from a goethite, an akageneite, a lepidocrocite, or a combination thereof. In some embodiments, the iron oxide hydroxide includes a goethite.

In some embodiments, the aluminum compound in the aqueous mixture including the catalyst, the aluminum compound, and the water includes an aluminum oxide. In some embodiments, the aluminum oxide includes an aluminum oxide hydroxide. In some embodiments, the aluminum oxide hydroxide includes an aluminum oxide hydroxide selected from a gibbsite, a bayerite, a boehmite, or a combination thereof. In some embodiments, the aluminum oxide hydroxide includes a boehmite.

In some embodiments, removing a substantial amount of water from the aqueous mixture including the catalyst, the iron compound, the aluminum compound, and the water to provide a precatalyst material includes heating the aqueous mixture at a temperature from about 50° C. to about 100° C. In some embodiments, removing a substantial amount of water from the aqueous mixture including the catalyst, the iron compound, the aluminum compound, and the water to provide a precatalyst material includes heating the aqueous mixture at a temperature of about 80° C. In some embodiments, removing a substantial amount of water from the aqueous mixture including the catalyst, the iron compound, the aluminum compound, and the water to provide a precatalyst material includes removing from about 50 wt. % to about 99 wt. % of the water.

In some embodiments, heating the precatalyst material to provide the catalyst material includes heating the precatalyst material at a temperature from about 300° C. to about 500° C. In some embodiments, heating the precatalyst material to provide the catalyst material includes heating the precatalyst material at a temperature from about 350° C. to about 450° C. In some embodiments, heating the precatalyst material to provide the catalyst material includes heating the precatalyst material in the presence of air, an oxidizing atmosphere, an inert atmosphere, or a combination thereof. In some embodiments, heating the precatalyst material to provide the catalyst material includes heating the precatalyst material the presence of air.

In some embodiments, the catalyst material is treated with a gas including ethane. In some embodiments, the gas further includes oxygen. In some embodiments, the gas further includes ethylene. In some embodiments, the catalyst material is treated with the gas including ethane at a temperature from about 100° C. to about 500° C. In some embodiments, the catalyst material is treated with the gas including ethane for about 18 hours to about 72 hours.

DESCRIPTION OF EMBODIMENTS

Figure 1:
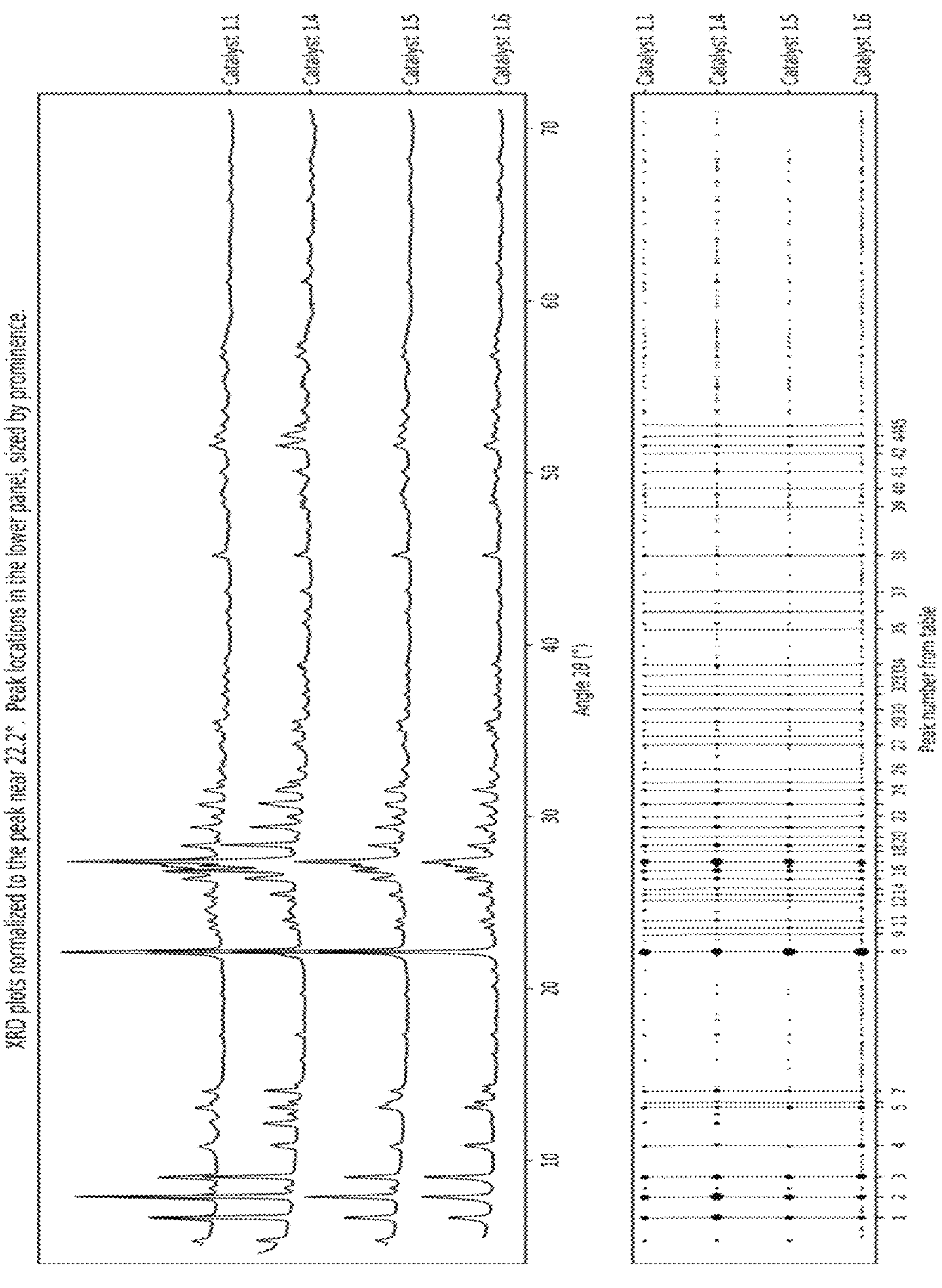
FIG. 1 shows the overlaid XRD plots of Catalysts 1.1 and 1.4-1.6.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B". In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. A comma can be used as a delimiter or digit group separator to the left or right of a decimal mark; for example, "0.000.1" is equivalent to "0.0001". All publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "room temperature" as used herein refers to a temperature of about 15° C. to about 28° C.

The molar ratio of molybdenum, vanadium, iron, aluminum, and optionally other elements in the catalysts and catalyst materials described herein can be determined by employing inductively coupled plasma mass spectrometry ICP-MS. For instance, as discussed in Examples section, the molar ratio of molybdenum, vanadium, iron, and aluminum in the catalyst materials described herein can be determined by a method that includes (1) first digesting (e.g., fully dissolving) the catalyst material (e.g., 10 mg of catalyst material) in (a) a solution that includes 10 wt. % to 15 wt. % NaOCl or (b) a solution that includes 25 mol/L NaOH; (2) heating, agitating, or heating and agitating the solution including to the catalyst material to facilitate digestion of the catalyst material, and (3) diluting the solution as necessary to prepare a sample suitable for ICP-MS analysis. For catalyst materials that cannot be adequately digested by the techniques described in the Examples section, Energy-dispersive X-ray spectroscopy (EDS) can be used to determine the molar ratio of molybdenum, vanadium, iron, aluminum, and optionally other elements in the catalysts and catalyst materials.

Catalyst Materials Including Molybdenum, Vanadium, Oxygen, and Iron

Provided in this disclosure is an oxidative dehydrogenation catalyst material that includes molybdenum, vanadium, oxygen, and iron. The molar ratio of molybdenum to vanadium in the catalyst material is from 1:0.1 to 1:0.5. The molar ratio of molybdenum to iron in the catalyst material is from 1:0.25 to 1:5.5. Further, oxygen is present in the catalyst material at least in amount to satisfy the valency of any present metal oxides.

As used herein, the term “catalyst material” refers to a material that can promote the oxidative dehydrogenation of ethane to ethylene. The catalyst material can be a plurality of particles or a formed catalyst material. Non-limiting examples of formed catalyst materials include extruded catalyst materials, pressed catalyst materials, and cast catalyst materials. Non-limiting examples of pressed and cast catalyst materials includes pellets-such as tablets, ovals, and spherical particles.

In some embodiments, the molar ratio of molybdenum to vanadium in the catalyst material is from 1:0.30 to 1:0.45. For example, the molar ratio of molybdenum to vanadium can be from 1:0.30 to 1:0.35 or from 1:0.35 to 1:0.45. In some embodiments, the molar ratio of molybdenum to vanadium is from 1:0.37 to 1:0.41.

In some embodiments, the catalyst material does not include niobium, tellurium, or both.

In some embodiments, at least a portion of the molybdenum and vanadium in the catalyst material can be present as a mixed metal oxide having the empirical formula:

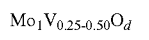

$$Mo_1V_{0.25\text{-}0.50}O_d$$

wherein d is a number to satisfy the valence of the oxide.

In some embodiments, the molar ratio of molybdenum to iron in the catalyst material is from 1:3 to 1:5.5. For example, the molar ratio of molybdenum to iron can be from 1:4.0 to 1:5.0 or from 1:4.25 to 1:4.75. In some embodiments, the molar ratio of molybdenum to iron is from 1:4.45 to 1:4.55.

In some embodiments, the molar ratio of molybdenum to vanadium in the catalyst material is from 1:0.30 to 1:0.45 and the molar ratio of molybdenum to iron is from 1:4.25 to 1:4.75.

In some embodiments, the molar ratio of molybdenum to iron in the catalyst material is from 1:0.25 to 1:1.0. For example, the molar ratio of molybdenum to iron can be from 1:0.25 to 1:0.75. In some embodiments, the molar ratio of molybdenum to iron is from 1:0.35 to 1:0.65. For example, the molar ratio of molybdenum to iron can be from 1:0.35 to 1:0.45 or from 1:0.55 to 1:0.65. In some embodiments, the molar ratio of molybdenum to iron is about 1:0.4. In some embodiments, the molar ratio of molybdenum to iron is about 1:0.6.

In some embodiments, the molar ratio of molybdenum to vanadium in the catalyst material is from 1:0.30 to 1:0.45 and the molar ratio of molybdenum to iron is from 1:0.35 to about 1:0.65.

In some embodiments, the molar ratio of molybdenum to iron in the catalyst material is from 1:1.3 to 1:2.2. For example, the molar ratio of molybdenum to iron can be from 1:1.6 to 1:2.0. In some embodiments, the molar ratio of molybdenum to iron is from 1:1.80 to 1:1.90.

In some embodiments, the molar ratio of molybdenum to vanadium in the catalyst material is from 1:0.30 to 1:0.45 and the molar ratio of molybdenum to iron is from 1:1.80 to 1:1.90.

In some embodiments, the molar ratio of molybdenum to iron in the catalyst material is from 1:2.0 to 1:2.5. For example, the molar ratio of molybdenum to iron can be from 1:2.3 to 1:2.7. In some embodiments, the molar ratio of molybdenum to iron is from 1:1.80 to 1:1.90.

In some embodiments, the molar ratio of molybdenum to vanadium in the catalyst material is from 1:0.30 to 1:0.45 and the molar ratio of molybdenum to iron is from 1:2.45 to 1:2.6.

In some embodiments, the catalyst material is characterized by having at least five XRD diffraction peaks (2θ degrees) chosen from 6.7±0.2, 7.9±0.2, 9.0±0.2, 10.9±0.2, 13.1±0.2, 14.0±0.2, 22.1±0.2, 26.3±0.2, 26.8±0.2, 27.3±0.2, 28.3±0.2, 29.3±0.2, 30.6±0.2, 31.5±0.2, 33.1±0.2, 35.6±0.2, 40.9±0.2, 45.2±0.2, 54.1±0.2, and 64.0±0.2, wherein the XRD is obtained using CuKα radiation.

In some embodiments, the catalyst material is characterized by having at least ten XRD diffraction peaks (2θ degrees) chosen from 6.7±0.2, 7.9±0.2, 9.0±0.2, 10.9±0.2, 13.1±0.2, 14.0±0.2, 22.1±0.2, 26.3±0.2, 26.8±0.2, 27.3±0.2, 28.3±0.2, 29.3±0.2, 30.6±0.2, 31.5±0.2, 33.1±0.2, 35.6±0.2, 40.9±0.2, 45.2±0.2, 54.1±0.2, and 64.0±0.2, wherein the XRD is obtained using CuKα radiation.

In some embodiments, the catalyst material is characterized by having at least fifteen XRD diffraction peaks (2θ degrees) chosen from 6.7±0.2, 7.9±0.2, 9.0±0.2, 10.9±0.2, 13.1±0.2, 14.0±0.2, 22.1±0.2, 26.3±0.2, 26.8±0.2, 27.3±0.2, 28.3±0.2, 29.3±0.2, 30.6±0.2, 31.5±0.2, 33.1±0.2, 35.6±0.2, 40.9±0.2, 45.2±0.2, 54.1±0.2, and 64.0±0.2, wherein the XRD is obtained using CuKα radiation.

In some embodiments, the catalyst material is characterized by having XRD diffraction peaks (2θ degrees) at from 6.7±0.2, 7.9±0.2, 9.0±0.2, 10.9±0.2, 13.1±0.2, 14.0±0.2, 22.1±0.2, 26.3±0.2, 26.8±0.2, 27.3±0.2, 28.3±0.2, 29.3±0.2, 30.6±0.2, 31.5±0.2, 33.1±0.2, 35.6±0.2, 40.9±0.2, 45.2±0.2, 54.1±0.2, and 64.0±0.2, wherein the XRD is obtained using CuKα radiation.

In some embodiments, the catalyst material is characterized by having at least five XRD diffraction peaks (2θ degrees) chosen from 6.7±0.2, 7.9±0.2, 9.0±0.2, 10.9±0.2, 13.1±0.2, and 22.1±0.2 wherein the XRD is obtained using CuKα radiation.

In some embodiments, the catalyst material is characterized by having XRD diffraction peaks (2θ degrees) at 6.7±0.2, 7.9±0.2, 9.0±0.2, 10.9±0.2, 13.1±0.2, and 22.1±0.2 wherein the XRD is obtained using CuKα radiation.

In some embodiments, the catalyst material has a BET surface area from 35 $m^2/g$ to 250 $m^2/g$. For example, the catalyst material can have a BET surface area from 40 $m^2/g$ to 200 $m^2/g$, 50 $m^2/g$ to 150 $m^2/g$, or from 55 $m^2/g$ to 100 $m^2/g$.

In some embodiments, the catalyst material has a pore volume from 0.03 $cm^3/g$ to 0.60 $cm^3/g$. For example, the catalyst material can have a pore volume from 0.04 $cm^3/g$ to 0.30 $cm^3/g$ or from 0.05 $cm^3/g$ to 0.20 $cm^3/g$.

In some embodiments, the catalyst material has a 35% conversion temperature from about 300° C. to about 400° C. For example, the catalyst material can have a 35% conversion temperature from about 300° C. to about 350° C. In some embodiments, the catalyst material has a 35% conversion temperature from about 315° C. to about 335° C.

As used in this disclosure, the phrase “35% conversion temperature” refers to the temperature at which 35% of ethane in a gas stream is converted to a product other than ethane. The 35% conversion temperature of an oxidative dehydrogenation catalyst can be determined by using a microreactor unit (MRU). In a microreactor unit, the 35% conversion temperature of a catalyst can be determined by passing a feed gas over a catalyst bed in a reactor tube. The MRU reactor tube has an outer diameter of about 0.5 inches and an internal diameter of about 0.4 inches and length of about 15 inches. For example, the reactor tube can be stainless-steel SWAGELOK® Tubing with a wall thickness of about 0.049 inches. The feed gas can include ethane and oxygen having a molar ratio of 70:30 to 90:10. For example, the feed gas can include ethane and oxygen having a molar ratio of 82:18. Alternatively, the feed gas can include ethane, oxygen, and nitrogen. The molar ratio of ethane to oxygen to nitrogen can be 18:18:64 to 54:18:28. For example, the molar ratio of ethane to oxygen to nitrogen can be 36:18:46 or 35:17.5:47.5. The flow rate of the feed gas can be about 70 standard cubic centimeters per minute (sccm) to about 80 sccm. For example, the flow rate of the feed gas can be about 75 sccm (e.g., 74.6 sccm). The catalyst bed consists of the oxidative dehydrogenation catalyst and a filler, such as sand, 1:0.5 to 1:3 volume ratio, with the total weight for the oxidative dehydrogenation catalyst being 1.96 to 2.00 g. Any remaining space in the reactor tube (e.g., below or above the catalyst bed) is packed with an additional filler, such as quartz sand. The 35% conversion temperature is determined at a weight hourly space velocity (WHSV) of 2.90 $h^{-1}$, with the WHSV based on the weight of $MoVO_x$ or $MoVFeO_x$ in the sample, and a gas hourly space velocity (GHSV) of about 2,000 to 3,000 $h^{-1}$. In cases where catalyst materials include an alumina—such as alumina hydroxide oxide (e.g., boehmite)—the original weight percentage of $MoVO_x$ or $MoVFeO_x$ produced from the by-weight combinations of these materials with alumina are assumed to be unchanged from post-mixing workups involving heat treatments. Therefore, the feed gas flow can be adjusted to a WHSV target of 2.90 $h^{-1}$ based on the original weight percentage of (i) $MoVO_x$ in a catalyst material that includes molybdenum, vanadium, oxygen, and aluminum (e.g., $MoVAlO_x$) or (ii) $MoVFeO_x$ in a catalyst material that includes molybdenum, vanadium, oxygen, iron, and aluminum (e.g., $MoVFeAlO_x$) at the time of mixing. Typically, the inlet pressure is in the range of about 1 pound per square inch gauge (psig) to about 2.5 psig and the outlet pressure is in the range of about 0 psig to about 0.5 psig. The gas feed exiting the catalyst bed is analyzed by gas chromatography to determine the percent of various hydrocarbons (e.g., ethane and ethylene) and, optionally other gases such as $O_2$, $CO_2$, and CO. Conversion of the feed gas is calculated as a mass flow rate change of ethane in the product compared to feed ethane mass flow rate using the following formula:

$$C = \left(\frac{2X_{Ethylene} + X_{CO_2} + X_{CO}}{2X_{Ethylene} + 2X_{Ethane} + X_{CO_2} + X_{CO}}\right) * 100$$

wherein C is the percent (molar percent) of feed gas that has been converted from ethane to another product (i.e., ethane conversion) and X is the molar concentration of the corresponding compound in the gaseous effluent exiting the reactor. The ethane conversion is then plotted as a function of temperatures to acquire a linear algebraic equation. The linear equation for ethane conversion is solved to determine the temperature in which the ethane conversion is 35% (i.e. the 35% conversion temperature). Not taken into account for calculating the 35% conversion of ethane temperature or selectivity to ethylene, were reaction the products exiting the reactor in an aqueous stream such as, but not limited to, acetic acid, maleic acid, propionic acid, ethanol, and acetaldehyde.

In some embodiments, the catalyst material has a selectivity to ethylene from about 65% to 99%. For example, the catalyst material can have a selectivity to ethylene from about 75% to 95%. In some embodiments, the catalyst material has a selectivity to ethylene from about 77% to about 85%.

As used in this disclosure, the phrase "selectivity to ethylene" refers to the percentage on a molar basis of converted or reacted ethane that forms ethylene. An oxidative dehydrogenation catalyst's selectivity to ethylene can be determined using an MRU as discussed above. An oxidative dehydrogenation catalyst's selectivity to ethylene can be determined using to the following equation:

$$S_{Ethylene} = \left(\frac{2 * X_{Ethylene}}{2 * X_{Ethylene} + X_{CO2} + X_{CO}}\right) * 100\%$$

wherein $S_{Ethylene}$ is the selectivity to ethylene, and X is the molar concentration of the corresponding compound in the gaseous effluent exiting the reactor. Notably, the selectivity to ethylene is determined at the 35% conversion temperature, unless otherwise indicated. As such, after the 35% conversion temperature is determined, the above equation for selectivity is solved using the corresponding values for $X_{Ethylene}$, $X_{CO2}$, and $X_{CO}$ at the 35% conversion temperature.

In some embodiments, the catalyst material has a selectivity to acetic acid of less than 15 wt. % in a process for the oxidative dehydrogenation of ethane to ethylene. For example, the catalyst material can have a selectivity to acetic acid of about 1 wt. % to about 15 wt. %, about 3 wt. % to about 12 wt. %, or about 7 wt. % to about 12 wt. % in a process for the oxidative dehydrogenation of ethane to ethylene. In some embodiments, the catalyst material has a selectivity to acetic acid of about 7 wt. %, 8 wt. %, 9 wt. %, 10 wt. %, 11 wt. %, 12 wt. % or about 13 wt. % in a process for the oxidative dehydrogenation of ethane to ethylene. Selectivity to acetic acid can be determined as described in the Examples section.

In some embodiments, at least a portion of the iron present in the catalyst material can be present as iron(III) (i.e., $Fe^{3+}$). The presence of iron(III) in the catalyst material can be detected by XPS.

In some embodiments, at least a portion of the iron in the catalyst material can be present as amorphous iron. The presence of amorphous iron in the catalyst material can be detected by XPS.

In some embodiments, at least a portion of the iron present in the catalyst material is present as an iron oxide, an iron oxide hydroxide, or a combination thereof. The presence of iron oxides and iron oxide hydroxides can be determined by X-ray powder diffraction (XRD).

When at least a portion of the iron in the catalyst material is present as an iron oxide, the iron oxide can include an iron oxide selected from hematite ($\alpha$-$Fe_2O_3$), maghemite ($\gamma$-$Fe_2O_3$), magnetite ($Fe_3O_4$), or a combination thereof. In some embodiments, at least a portion of the iron in the catalyst material is present as hematite.

When at least a portion of the iron in the catalyst material is present as an iron oxide hydroxide, the iron oxide hydroxide can include an iron oxide hydroxide selected from a goethite ($\alpha$-FeO(OH)), an akaganeite ($\beta$-FeO(OH)), a lepidocrocite ($\gamma$-FeO(OH)), or a combination thereof. In some embodiments, at least a portion of the iron in the catalyst material is present as a goethite.

In some embodiments, at least a portion of the iron in the catalyst material is present as a goethite and at least a portion of the iron in the catalyst material is present as hematite.

The catalyst materials provided above that include molybdenum, vanadium, oxygen, and iron can prepared by a method that includes preparing an aqueous mixture including (i) a catalyst that includes molybdenum, vanadium, and oxygen; (ii) an iron compound, and (iii) a water. The method further includes removing a substantial amount of the water from the mixture to provide a precatalyst material. Subsequently, the precatalyst material is heated to provide the catalyst material.

In some embodiments, the method further includes preparing the catalyst including molybdenum, vanadium, and oxygen.

In some embodiments, the molar ratio of molybdenum to vanadium in the provided catalyst is from 1:0.25 to 1:0.6. For example, the molar ratio of molybdenum to vanadium in the catalyst can be from 1:0.35 to 1:0.55. In some embodiments, the molar ratio of molybdenum to vanadium in the provided catalyst is from 1:0.40 to 1:0.49.

In some embodiments, the provided catalyst includes a mixed metal oxide having the empirical formula:

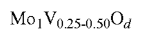

wherein d is a number to satisfy the valence of the oxide.

In some embodiments, the iron compound in the aqueous mixture includes an iron(III) compound. In some embodiments, the iron compound in the mixture of the catalyst, the iron compound, and the water includes an iron compound selected from an iron oxide, an iron oxide hydroxide, or a combination thereof. The iron oxide be an iron oxide selected from hematite (α-$Fe_2O_3$), maghemite (γ-$Fe_2O_3$), magnetite ($Fe_3O_4$), or a combination thereof. The iron oxide hydroxide can be an iron oxide hydroxide selected from a goethite, an akageneite, a lepidocrocite, or a combination thereof. In some embodiments, the iron compound in the mixture of the catalyst, the iron compound, and the water includes hematite. In some embodiments, the iron compound in the mixture of the catalyst, the iron compound, and the water includes goethite. In some embodiments, the iron compound in the mixture of the catalyst, the iron compound, and the water includes goethite and hematite.

Removing a substantial amount of water from the aqueous mixture including the catalyst, the iron compound, and the water to provide a precatalyst material can include removing from about 50 wt. % to about 99 wt. % of the water. For example, about 50 wt. % to about 75 wt. % or about 75 wt. % to about 99 wt. % of the water can be removed to provide the precatalyst material. For example, enough water can be removed from the aqueous mixture such that the provided catalyst material has a paste-like consistency.

In some embodiments, removing a substantial amount of the water from the mixture of the catalyst, the iron compound, and the water to provide a precatalyst material includes heating the aqueous mixture at a temperature from about 50° C. to about 280° C., about 50° C. to about 250° C., or about 50° C. to about 100° C. For example, the aqueous mixture can be heated at a temperature of about 80° C.

In some embodiments, heating the precatalyst material to provide the catalyst material includes heating the precatalyst material at a temperature from about 300° C. to about 500° C. For example, heating the precatalyst material to provide the catalyst material can include heating the precatalyst material at a temperature from about 350° C. to about 450° C. In some embodiments, heating the precatalyst material to provide the catalyst material includes heating the precatalyst material at a temperature of about 350° C. to about 375° C., about 375° C. to about 400° C., about 400° C. to about 425° C., or about 425° C. to about 450° C.

Further, heating the precatalyst material to provide the catalyst material can include heating the precatalyst material in the presence of air, an oxidizing atmosphere, an inert atmosphere, or a combination thereof. In some embodiments, heating the precatalyst material to provide the catalyst material includes heating the precatalyst material the presence of air.

In some embodiments, after the catalyst material is prepared, the catalyst material can be treated with a gas that includes ethane, oxygen, ethylene, or a combination thereof. For example, the catalyst material can be treated with a gas that includes ethane, oxygen, ethylene, or a combination thereof in an oxidative dehydrogenation reactor.

In some embodiments, the catalyst material is treated with a gas including ethane, oxygen, ethylene, or a combination thereof at an elevated temperature. For example, the catalyst material can be treated with a gas including ethane, oxygen, ethylene, or a combination thereof at a temperature from about 100° C. to about 500° C., about 200° C. to about 450° C., or about 300° C. to about 400° C. In some embodiments, the catalyst material is treated with a gas including ethane, oxygen, ethylene, or a combination thereof for about 6 hours to about 144 hours or about 18 hours to about 72 hours. In some embodiments, the catalyst material is treated with the gas including ethane, oxygen, ethylene, or combination thereof in an oxidative dehydrogenation reactor.

Also provided herein is a catalyst material that includes molybdenum, vanadium, oxygen, and iron. The molar ratio of molybdenum to vanadium in the catalyst material is from 1:0.30 to 1:0.45. The molar ratio of molybdenum to iron is from 1:4.25 to 1:4.75. Further, at least a portion of the iron in the catalyst material is present as goethite, hematite, or a combination thereof.

In some embodiments, the catalyst material is characterized by having at least five XRD diffraction peaks (2θ degrees) chosen from 6.7±0.2, 7.9±0.2, 9.0±0.2, 10.9±0.2, 13.1±0.2, 14.0±0.2, 22.1±0.2, 26.3±0.2, 26.8±0.2, 27.3±0.2, 28.3±0.2, 29.3±0.2, 30.6±0.2, 31.5±0.2, 33.1±0.2, 35.6±0.2, 40.9±0.2, 45.2±0.2, 54.1±0.2, and 64.0±0.2, wherein the XRD is obtained using CuKα radiation.

In some embodiments, the catalyst material is prepared by a method that includes providing a catalyst including molybdenum, vanadium, and oxygen and, subsequently, preparing an aqueous mixture that includes the catalyst, goethite, and a water. The weight ratio of catalyst to goethite in the aqueous mixture can be from 3:6 to 3:8. For example, the weight ratio can be about 3:7. The method can further include removing a substantial amount of the water from the mixture to provide a precatalyst material and, then, heating the precatalyst material to provide the catalyst material. The molar ratio of molybdenum to vanadium in the catalyst can be from 1:0.35 to 1:0.55. Further, removing a substantial amount of water from the mixture of the catalyst, the goethite, and the water to provide a precatalyst material can include heating the mixture at a temperature from about 50° C. to about 100° C. Heating the precatalyst material to provide the catalyst material can include heating the precatalyst material at a temperature from about 350° C. to about 450° C.

In some embodiments, the catalyst material is treated with a gas that includes ethane, oxygen, ethylene, or a combination thereof at a temperature from about 300° C. to about 400° C. In some embodiments, the catalyst material is treated with a gas that includes ethane, oxygen, ethylene, or a combination thereof for a time of about 18 hours to about 72 hours. The gas treatment can convert at least a portion of the goethite to hematite.

Also provided herein is a catalyst material that includes molybdenum, vanadium, oxygen, and iron. The molar ratio of molybdenum to vanadium in the catalyst material is from 1:0.30 to 1:0.45. The molar ratio of molybdenum to iron is from 1:0.5 to 1:0.7. Further, at least a portion of the iron in the catalyst material is present as goethite, hematite, or a combination thereof.

In some embodiments, the catalyst material is characterized by having at least five XRD diffraction peaks (2θ degrees) chosen from 6.7±0.2, 7.9±0.2, 9.0±0.2, 10.9±0.2, 13.1±0.2, 14.0±0.2, 22.1±0.2, 26.3±0.2, 26.8±0.2, 27.3±0.2, 28.3±0.2, 29.3±0.2, 30.6±0.2, 31.5±0.2, 33.1±0.2, 35.6±0.2, 40.9±0.2, 45.2±0.2, 54.1±0.2, and 64.0±0.2, wherein the XRD is obtained using CuKα radiation.

In some embodiments, the catalyst material is prepared by a method that includes providing a catalyst including molybdenum, vanadium, and oxygen and, subsequently, preparing an aqueous mixture that includes the catalyst, goethite, and a water. The weight ratio of catalyst to goethite in the aqueous mixture can be from 3:0.5 to 3:1.5. For example, the weight ratio can be about 3:1. The method can further include removing a substantial amount of the water from the mixture to provide a precatalyst material and, then, heating the precatalyst material to provide the catalyst material. The molar ratio of molybdenum to vanadium in the catalyst can be from 1:0.35 to 1:0.55. Further, removing a substantial amount of water from the mixture of the catalyst, the goethite, and the water to provide a precatalyst material can include heating the mixture at a temperature from about 50° C. to about 100° C. Heating the precatalyst material to provide the catalyst material can include heating the precatalyst material at a temperature from about 350° C. to about 450° C.

In some embodiments, the catalyst material is treated with a gas that includes ethane, oxygen, ethylene, or a combination thereof at a temperature from about 300° C. to about 400° C. In some embodiments, the catalyst material is treated with a gas that includes ethane, oxygen, ethylene, or a combination thereof for a time of about 18 hours to about 72 hours. The gas treatment can convert at least a portion of the goethite to hematite.

Also provided herein is a catalyst material that includes molybdenum, vanadium, oxygen, and iron. The molar ratio of molybdenum to vanadium in the catalyst material is from 1:0.30 to 1:45. The molar ratio of molybdenum to iron is from 1:1.6 to 1:2.0. Further, at least a portion of the iron in the catalyst material is present as goethite, hematite, or a combination thereof.

In some embodiments, the catalyst material is characterized by having at least five XRD diffraction peaks (2θ degrees) chosen from 6.7±0.2, 7.9±0.2, 9.0±0.2, 10.9±0.2, 13.1±0.2, 14.0±0.2, 22.1±0.2, 26.3±0.2, 26.8±0.2, 27.3±0.2, 28.3±0.2, 29.3±0.2, 30.6±0.2, 31.5±0.2, 33.1±0.2, 35.6±0.2, 40.9±0.2, 45.2±0.2, 54.1±0.2, and 64.0±0.2, wherein the XRD is obtained using CuKα radiation.

In some embodiments, the catalyst material is prepared by a method that includes providing a catalyst including molybdenum, vanadium, and oxygen and, subsequently, preparing an aqueous mixture that includes the catalyst, goethite, and a water. The weight ratio of catalyst to goethite in the aqueous mixture can be from 3:2 to 3:4. For example, the weight ratio can be about 3:3. The method can further include removing a substantial amount of the water from the mixture to provide a precatalyst material and, then, heating the precatalyst material to provide the catalyst material. The molar ratio of molybdenum to vanadium in the catalyst can be from 1:0.35 to 1:0.55. Further, removing a substantial amount of water from the mixture of the catalyst, the goethite, and the water to provide a precatalyst material can include heating the mixture at a temperature from about 50° C. to about 100° C. Heating the precatalyst material to provide the catalyst material can include heating the precatalyst material at a temperature from about 350° C. to about 450° C.

In some embodiments, the catalyst material is treated with a gas that includes ethane, oxygen, ethylene, or a combination thereof at a temperature from about 300° C. to about 400° C. In some embodiments, the catalyst material is treated with a gas that includes ethane, oxygen, ethylene, or a combination thereof for a time of about 18 hours to about 72 hours. The gas treatment can convert at least a portion of the goethite to hematite.

Also provided herein is a catalyst material that includes molybdenum, vanadium, oxygen, and iron. The molar ratio of molybdenum to vanadium in the catalyst material is from 1:0.30 to 1:45. The molar ratio of molybdenum to iron is from 1:2.3 to 1:2.70. Further, at least a portion of the iron in the catalyst material is present as goethite, hematite, or a combination thereof.

In some embodiments, the catalyst material is characterized by having at least five XRD diffraction peaks (2θ degrees) chosen from 6.7±0.2, 7.9±0.2, 9.0±0.2, 10.9±0.2, 13.1±0.2, 14.0±0.2, 22.1±0.2, 26.3±0.2, 26.8±0.2, 27.3±0.2, 28.3±0.2, 29.3±0.2, 30.6±0.2, 31.5±0.2, 33.1±0.2, 35.6±0.2, 40.9±0.2, 45.2±0.2, 54.1±0.2, and 64.0±0.2, wherein the XRD is obtained using CuKα radiation.

In some embodiments, the catalyst material is prepared by a method that includes providing a catalyst including molybdenum, vanadium, and oxygen and, subsequently, preparing an aqueous mixture that includes the catalyst, goethite, and a water. The weight ratio of catalyst to goethite in the aqueous mixture can be from 3:3 to 3:5. For example, the weight ratio can be about 3:4. The method can further include removing a substantial amount of the water from the mixture to provide a precatalyst material and, then, heating the precatalyst material to provide the catalyst material. The molar ratio of molybdenum to vanadium in the catalyst can be from 1:0.30 to 1:0.55. Further, removing a substantial amount of water from the mixture of the catalyst, the goethite, and the water to provide a precatalyst material can include heating the mixture at a temperature from about 50° C. to about 100° C. Heating the precatalyst material to provide the catalyst material can include heating the precatalyst material at a temperature from about 350° C. to about 450° C.

In some embodiments, the catalyst material is treated with a gas that includes ethane, oxygen, ethylene, or a combination thereof at a temperature from about 300° C. to about 400° C. In some embodiments, the catalyst material is treated with a gas that includes ethane, oxygen, ethylene, or a combination thereof for a time of about 18 hours to about 72 hours. The gas treatment can convert at least a portion of the goethite to hematite.

Catalyst Materials Including Molybdenum, Vanadium, Oxygen, and Aluminum

Also provided herein is an oxidative dehydrogenation catalyst material that includes molybdenum, vanadium, oxygen, and aluminum. The molar ratio of molybdenum to vanadium is from 1:0.1 to 1:0.5. The molar ratio of molybdenum to aluminum is from 1:1.5 to 1:6.5. Further, oxygen is present at least in an amount to satisfy the valency of any present metal oxides.

In some embodiments, the molar ratio of molybdenum to vanadium in the catalyst material is from 1:0.25 to 1:0.50. In some embodiments, the molar ratio of molybdenum to vanadium in the catalyst material is from 1:0.30 to 1:0.45. For example, the molar ratio of molybdenum to vanadium can be from 1:0.30 to 1:0.35 or from 1:0.35 to 1:0.45. In some embodiments, the molar ratio of molybdenum to vanadium is from 1:0.37 to 1:0.41.

In some embodiments, the molar ratio of molybdenum to vanadium in the catalyst material is from 1:2.5 to 1:6.0.

In some embodiments, the catalyst material does not include niobium, tellurium, or both.

In some embodiments, at least a portion of the molybdenum and vanadium in the catalyst material can be present as a mixed metal oxide having the empirical formula:

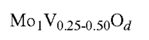

wherein d is a number to satisfy the valence of the oxide.

In some embodiments, the molar ratio of molybdenum to aluminum is from 1:3.0 to 1:6.5. For example, the molar ratio of molybdenum to aluminum can be from 1:3.25 to 1:5.5. In some embodiments, the molar ratio of molybdenum to vanadium is from 1:3.5 to 1:4.1. For example, the molar ratio of molybdenum to aluminum can be from 1:3.9 to 1:4.3. In some embodiments, the molar ratio of molybdenum to vanadium is from 1:4.8 to 5.2. For example, the molar ratio of molybdenum to aluminum can be from 1:4.95 to 1:5.05.

In some embodiments, the molar ratio of molybdenum to vanadium in the catalyst material is from 1:0.30 to 1:0.45 and the molar ratio of molybdenum to aluminum is from 1:3.8 to 1:4.3. In some embodiments, the molar ratio of molybdenum to vanadium in the catalyst material is from 1:0.30 to 1:0.45 and the molar ratio of molybdenum to aluminum is from 1:4.8 to 5.2.

In some embodiments, the molar ratio of molybdenum to aluminum is from 1:1.5 to 1:3.5. For example, the molar ratio of molybdenum to aluminum can be from 1:1.5 to 1:2.5 or from 2.5 to 3.5. In some embodiments, the molar ratio of molybdenum to aluminum is from 1:2.0 to 1:2.2 or from 1:2.9 to 1:3.1.

In some embodiments, the molar ratio of molybdenum to vanadium in the catalyst material is from 1:0.30 to 1:0.45 and the molar ratio of molybdenum to aluminum is from 1:1.5 to 1:2.5. In some embodiments, the molar ratio of molybdenum to vanadium in the catalyst material is from 1:0.30 to 1:0.45 and the molar ratio of molybdenum to aluminum is from 1:2.5 to 1:3.5.

In some embodiments, the catalyst material is characterized by having at least five XRD diffraction peaks (2θ degrees) chosen from 6.7±0.2, 7.9±0.2, 9.1±0.2, 10.9±0.2, 13.0±0.2, 13.4±0.2, 14.0±0.2, 14.4±0.2, 22.1±0.2, 23.1±0.2, 23.5±0.2, 23.9±0.2, 25.4±0.2, 25.8±0.2, 26.3±0.2, 26.8±0.2, 29.3±0.2, 29.9±0.2, 30.6±0.2, 31.5±0.2, 32.0±0.2, 32.8±0.2, 34.2±0.2, 35.0±0.2, 35.5±0.2, 36.2±0.2, 37.1±0.2, 37.5±0.2, 38.2±0.2, 38.8±0.2, 41.1±0.2, 41.8±0.2, 43.0±0.2, 45.2±0.2, 46.2±0.2, 47.2±0.2, 47.9±0.2, 48.3±0.2, 48.8±0.2, 49.3±0.2, 49.9±0.2, 51.4±0.2, 52.0±0.2, 52.7±0.2, 53.6±0.2, 55.2±0.2, 56.7±0.2, and 57.2±0.2, wherein the XRD is obtained using CuKα radiation.

In some embodiments, the catalyst material is characterized by having at least ten XRD diffraction peaks (2θ degrees) chosen from 6.7±0.2, 7.9±0.2, 9.1±0.2, 10.9±0.2, 13.0±0.2, 13.4±0.2, 14.0±0.2, 14.4±0.2, 22.1±0.2, 23.1±0.2, 23.5±0.2, 23.9±0.2, 25.4±0.2, 25.8±0.2, 26.3±0.2, 26.8±0.2, 29.3±0.2, 29.9±0.2, 30.6±0.2, 31.5±0.2, 32.0±0.2, 32.8±0.2, 34.2±0.2, 35.0±0.2, 35.5±0.2, 36.2±0.2, 37.1±0.2, 37.5±0.2, 38.2±0.2, 38.8±0.2, 41.1±0.2, 41.8±0.2, 43.0±0.2, 45.2±0.2, 46.2±0.2, 47.2±0.2, 47.9±0.2, 48.3±0.2, 48.8±0.2, 49.3±0.2, 49.9±0.2, 51.4±0.2, 52.0±0.2, 52.7±0.2, 53.6±0.2, 55.2±0.2, 56.7±0.2, and 57.2±0.2, wherein the XRD is obtained using CuKα radiation.

In some embodiments, the catalyst material is characterized by having at least fifteen XRD diffraction peaks (2θ degrees) chosen from 6.7±0.2, 7.9±0.2, 9.1±0.2, 10.9±0.2, 13.0±0.2, 13.4±0.2, 14.0±0.2, 14.4±0.2, 22.1±0.2, 23.1±0.2, 23.5±0.2, 23.9±0.2, 25.4±0.2, 25.8±0.2, 26.3±0.2, 26.8±0.2, 29.3±0.2, 29.9±0.2, 30.6±0.2, 31.5±0.2, 32.0±0.2, 32.8±0.2, 34.2±0.2, 35.0±0.2, 35.5±0.2, 36.2±0.2, 37.1±0.2, 37.5±0.2, 38.2±0.2, 38.8±0.2, 41.1±0.2, 41.8±0.2, 43.0±0.2, 45.2±0.2, 46.2±0.2, 47.2±0.2, 47.9±0.2, 48.3±0.2, 48.8±0.2, 49.3±0.2, 49.9±0.2, 51.4±0.2, 52.0±0.2, 52.7±0.2, 53.6±0.2, 55.2±0.2, 56.7±0.2, and 57.2±0.2, wherein the XRD is obtained using CuKα radiation.

In some embodiments, the catalyst material is characterized by having at least twenty XRD diffraction peaks (2θ degrees) chosen from 6.7±0.2, 7.9±0.2, 9.1±0.2, 10.9±0.2, 13.0±0.2, 13.4±0.2, 14.0±0.2, 14.4±0.2, 22.1±0.2, 23.1±0.2, 23.5±0.2, 23.9±0.2, 25.4±0.2, 25.8±0.2, 26.3±0.2, 26.8±0.2, 29.3±0.2, 29.9±0.2, 30.6±0.2, 31.5±0.2, 32.0±0.2, 32.8±0.2, 34.2±0.2, 35.0±0.2, 35.5±0.2, 36.2±0.2, 37.1±0.2, 37.5±0.2, 38.2±0.2, 38.8±0.2, 41.1±0.2, 41.8±0.2, 43.0±0.2, 45.2±0.2, 46.2±0.2, 47.2±0.2, 47.9±0.2, 48.3±0.2, 48.8±0.2, 49.3±0.2, 49.9±0.2, 51.4±0.2, 52.0±0.2, 52.7±0.2, 53.6±0.2, 55.2±0.2, 56.7±0.2, and 57.2±0.2, wherein the XRD is obtained using CuKα radiation.

In some embodiments, the catalyst material is characterized by having at least thirty XRD diffraction peaks (2θ degrees) chosen from 6.7±0.2, 7.9±0.2, 9.1±0.2, 10.9±0.2, 13.0±0.2, 13.4±0.2, 14.0±0.2, 14.4±0.2, 22.1±0.2, 23.1±0.2, 23.5±0.2, 23.9±0.2, 25.4±0.2, 25.8±0.2, 26.3±0.2, 26.8±0.2, 29.3±0.2, 29.9±0.2, 30.6±0.2, 31.5±0.2, 32.0±0.2, 32.8±0.2, 34.2±0.2, 35.0±0.2, 35.5±0.2, 36.2±0.2, 37.1±0.2, 37.5±0.2, 38.2±0.2, 38.8±0.2, 41.1±0.2, 41.8±0.2, 43.0±0.2, 45.2±0.2, 46.2±0.2, 47.2±0.2, 47.9±0.2, 48.3±0.2, 48.8±0.2, 49.3±0.2, 49.9±0.2, 51.4±0.2, 52.0±0.2, 52.7±0.2, 53.6±0.2, 55.2±0.2, 56.7±0.2, and 57.2±0.2, wherein the XRD is obtained using CuKα radiation.

In some embodiments, the catalyst material is characterized by having at least forty XRD diffraction peaks (2θ degrees) chosen from 6.7±0.2, 7.9±0.2, 9.1±0.2, 10.9±0.2, 13.0±0.2, 13.4±0.2, 14.0±0.2, 14.4±0.2, 22.1±0.2, 23.1±0.2, 23.5±0.2, 23.9±0.2, 25.4±0.2, 25.8±0.2, 26.3±0.2, 26.8±0.2, 29.3±0.2, 29.9±0.2, 30.6±0.2, 31.5±0.2, 32.0±0.2, 32.8±0.2, 34.2±0.2, 35.0±0.2, 35.5±0.2, 36.2±0.2, 37.1±0.2, 37.5±0.2, 38.2±0.2, 38.8±0.2, 41.1±0.2, 41.8±0.2, 43.0±0.2, 45.2±0.2, 46.2±0.2, 47.2±0.2, 47.9±0.2, 48.3±0.2, 48.8±0.2, 49.3±0.2, 49.9±0.2, 51.4±0.2, 52.0±0.2, 52.7±0.2, 53.6±0.2, 55.2±0.2, 56.7±0.2, and 57.2±0.2, wherein the XRD is obtained using CuKα radiation.

In some embodiments, the catalyst material is characterized by having at least forty-five XRD diffraction peaks (2θ degrees) chosen from 6.7±0.2, 7.9±0.2, 9.1±0.2, 10.9±0.2, 13.0±0.2, 13.4±0.2, 14.0±0.2, 14.4±0.2, 22.1±0.2, 23.1±0.2, 23.5±0.2, 23.9±0.2, 25.4±0.2, 25.8±0.2, 26.3±0.2, 26.8±0.2, 29.3±0.2, 29.9±0.2, 30.6±0.2, 31.5±0.2, 32.0±0.2, 32.8±0.2, 34.2±0.2, 35.0±0.2, 35.5±0.2, 36.2±0.2, 37.1±0.2, 37.5±0.2, 38.2±0.2, 38.8±0.2, 41.1±0.2, 41.8±0.2, 43.0±0.2, 45.2±0.2, 46.2±0.2, 47.2±0.2, 47.9±0.2, 48.3±0.2, 48.8±0.2, 49.3±0.2, 49.9±0.2, 51.4±0.2, 52.0±0.2, 52.7±0.2, 53.6±0.2, 55.2±0.2, 56.7±0.2, and 57.2±0.2, wherein the XRD is obtained using CuKα radiation.

In some embodiments, the catalyst material is characterized by having at least five XRD diffraction peaks (2θ degrees) chosen from 6.7±0.2, 7.9±0.2, 9.1±0.2, 10.9±0.2, 13.0±0.2, 14.0±0.2, 22.1±0.2, 26.3±0.2, 26.8±0.2, 27.3±0.2, 28.3±0.2, 30.6±0.2, 31.5±0.2, and 45.2±0.2 wherein the XRD is obtained using CuKα radiation.

In some embodiments, the catalyst material is characterized by having at least ten XRD diffraction peaks (2θ degrees) chosen from 6.7±0.2, 7.9±0.2, 9.1±0.2, 10.9±0.2, 13.0±0.2, 14.0±0.2, 22.1±0.2, 26.3±0.2, 26.8±0.2, 27.3±0.2, 28.3±0.2, 30.6±0.2, 31.5±0.2, and 45.2±0.2 wherein the XRD is obtained using CuKα radiation.

In some embodiments, the catalyst material is characterized by having XRD diffraction peaks (2θ degrees) at 6.7±0.2, 7.9±0.2, 9.1±0.2, 10.9±0.2, 13.0±0.2, 14.0±0.2, 22.1±0.2, 26.3±0.2, 26.8±0.2, 27.3±0.2, 28.3±0.2, 30.6±0.2, 31.5±0.2, and 45.2±0.2 wherein the XRD is obtained using CuKα radiation.

In some embodiments, the catalyst material is characterized by having at least five XRD diffraction peaks (2θ degrees) chosen from 6.7±0.2, 7.9±0.2, 9.1±0.2, 10.9±0.2, 13.0±0.2, 14.0±0.2, 22.1±0.2, 26.3±0.2, 26.8±0.2, 27.3±0.2, 28.3±0.2, 30.6±0.2, 31.5±0.2, and 45.2±0.2 and at least one broad peak chosen from 13.9±0.2, 28.2±0.2, 38.5±0.2, 49.1±0.2, 55.7±0.2, and 65.0±0.2 wherein the XRD is obtained using CuKα radiation.

In some embodiments, the catalyst material is characterized by having at least ten XRD diffraction peaks (2θ degrees) chosen from 6.7±0.2, 7.9±0.2, 9.1±0.2, 10.9±0.2, 13.0±0.2, 14.0±0.2, 22.1±0.2, 26.3±0.2, 26.8±0.2, 27.3±0.2, 28.3±0.2, 30.6±0.2, 31.5±0.2, and 45.2±0.2 and at least one broad peak chosen from 13.9±0.2, 28.2±0.2, 38.5±0.2, 49.1±0.2, 55.7±0.2, and 65.0±0.2 and wherein the XRD is obtained using CuKα radiation.

In some embodiments, the catalyst material is characterized by having XRD diffraction peaks (2θ degrees) at 6.7±0.2, 7.9±0.2, 9.1±0.2, 10.9±0.2, 13.0±0.2, 14.0±0.2, 22.1±0.2, 26.3±0.2, 26.8±0.2, 27.3±0.2, 28.3±0.2, 30.6±0.2, 31.5±0.2, and 45.2±0.2 and at least one broad peak chosen from 13.9±0.2, 28.2±0.2, 38.5±0.2, 49.1±0.2, 55.7±0.2, and 65.0±0.2 wherein the XRD is obtained using CuKα radiation.

In some embodiments, the catalyst material has a BET surface area from 50 $m^2/g$ to 300 $m^2/g$. For example, the catalyst material can have a BET surface area from 100 $m^2/g$ to 250 $m^2/g$ or from 125 $m^2/g$ to 225 $m^2/g$. In some embodiments, the catalyst material has a BET surface area from 125 $m^2/g$ to 175 $m^2/g$ or from 175 $m^2/g$ to 225 $m^2/g$.

In some embodiments, the catalyst material has a pore volume from 0.10 $cm^3/g$ to 1.00 $cm^3/g$. For example, the catalyst material can have a pore volume from 0.15 $cm^3/g$ to 0.65 $cm^3/g$ or from 0.20 $cm^3/g$ to 0.60 $cm^3/g$. In some embodiments, the catalyst material has a pore volume from 0.20 $cm^3/g$ to 0.40 $cm^3/g$ or from 0.40 $cm^3/g$ to 0.60 $cm^3/g$.

In some embodiments, the catalyst material has an amorphous content from about 25 wt. % to about 75 wt. %. For example, the catalyst material can have an amorphous content from about 30 wt. % to about 65 wt. %. In some embodiments, the catalyst material has an amorphous content from about 30 wt. % to about 40 wt. %. In some embodiments, the catalyst material has an amorphous content from about 50 wt. % to about 70 wt. %. For example, the catalyst material can have an amorphous content from about 55 wt. % to about 65 wt. %.

In some embodiments, the catalyst material has a 35% conversion temperature from about 300° C. to about 400° C. For example, the catalyst material can have a 35% conversion temperature from about 300° C. to about 350° C. In some embodiments, the catalyst material has a 35% conversion temperature from about 315° C. to about 335° C.

In some embodiments, the catalyst material has a selectivity to ethylene from about 65% to 99%. For example, the catalyst material can have a selectivity to ethylene from about 75% to 95%. In some embodiments, the catalyst material has a selectivity to ethylene from about 77% to about 85%.

In some embodiments, the catalyst material has a selectivity to acetic acid of less than 15 wt. % in a process for the oxidative dehydrogenation of ethane. For example, the catalyst material can have a selectivity to acetic acid of about 1 wt. % to about 15 wt. %, about 3 wt. % to about 12 wt. %, or about 7 wt. % to about 12 wt. % in a process for the oxidative dehydrogenation of ethane. In some embodiments, the catalyst material has a selectivity to acetic acid of about 7 wt. %, 8 wt. %, 9 wt. %, 10 wt. %, 11 wt. %, 12 wt. % or about 13 wt. % in a process for the oxidative dehydrogenation of ethane. Selectivity to acetic acid can be determined as described in Examples section.

In some embodiments, at least a portion of the aluminum in the catalyst material is present as an aluminum oxide. In some embodiments, the aluminum oxide is an aluminum oxide hydroxide. The aluminum oxide hydroxide can include a gibbsite, a bayerite, a boehmite, or a combination thereof. In some embodiments, at least a portion of the aluminum in the catalyst material is present as a boehmite. In some embodiments, at least a portion of the aluminum in the catalyst material is present as gamma alumina.

The catalyst materials provided herein that include molybdenum, vanadium, oxygen, and aluminum can prepared by a method that includes preparing an aqueous mixture including (i) a catalyst that includes molybdenum, vanadium, and oxygen; (ii) an aluminum compound, and (iii) a water. The method further includes removing a substantial amount of the water from the mixture to provide a precatalyst material. The method also includes the heating the precatalyst material to provide the catalyst material.

In some embodiments, the method further includes preparing the catalyst including molybdenum, vanadium, and oxygen.

In some embodiments, the molar ratio of molybdenum to vanadium in the catalyst is from 1:0.25 to 1:0.6. For example, the molar ratio of molybdenum to vanadium in the catalyst can be from 1:0.35 to 1:0.55. In some embodiments, the molar ratio of molybdenum to vanadium in the catalyst is from 1:0.40 to 1:0.49.

In some embodiments, the catalyst includes a mixed metal oxide having the empirical formula:

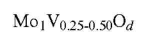

wherein d is a number to satisfy the valence of the oxide.

In some embodiments, the aluminum compound in the mixture including the catalyst, the aluminum compound, and the water includes an aluminum oxide. In some embodiments, the aluminum oxide includes an aluminum oxide hydroxide. The aluminum oxide hydroxide can include a gibbsite, a bayerite, a boehmite, or a combination thereof. In some embodiments, the aluminum compound used to prepare the aqueous mixture includes a boehmite. In some embodiments, the boehmite includes a pseudoboehmite such as VERSAL™ 250. VERSAL™ 250 has a dispersibility index (%<1 mu) of 20-30, a bulk density of 12-16 pounds per cubic foot (lbs/$ft^3$), a surface area of about 320 meters squared per gram ($m^2$/g), and a loss on ignition (LOI) of about 26 wt. %. The dispersibility index for VERSAL™ 250 can be determined by using 8 grams of sample on a volatile free basis and 96 milliliters (mL) of 0.22 normal (N) nitric acid solution, which is approximately 260 mol equivalent nitric acid per 100 grams (g) of alumina, mixing the acidic alumina slurry in a WARING® blender at low speed (17000 rpm) for 5 min, and then determining particle size distribution by using a SEDIGRAPH® PSA with the results reported as wt. % submicron particles. In some embodiments, the boehmite includes CATAPAL® B. CATAPAL® B is an alumina hydrate that has a loose bulk density of 670 to 750 g/L, a packed bulk density of 800 to 1100 g/L, a particle size ($d_{50}$) of 60 μm, a surface area (BET) after activation at 550° C. for 3 hours of 250 $m^2$/g, a pore volume after activation at 550° C. for 3 hours of 0.5 ml/g, and a crystallite size of about 4.5 nm.

Removing a substantial amount of water from the aqueous mixture including the catalyst, the aluminum compound, and the water to provide a precatalyst material can include removing from about 50 wt. % to about 99 wt. % of the water. For example, about 50 wt. % to about 75 wt. % or about 75 wt. % to about 99 wt. % of the water can be removed to provide the precatalyst material. For example, enough water can be removed from the aqueous mixture such that the provided catalyst material has a paste-like consistency.

In some embodiments, removing a substantial amount of the water from the aqueous mixture of the catalyst, the aluminum compound, and the water to provide a precatalyst material includes heating the aqueous mixture at a temperature from about 50° C. to about 280° C., about 50° C. to about 250° C., or about 50° C. to about 100° C. For example, the aqueous mixture can be heated at a temperature of about 80° C.

In some embodiments, heating the precatalyst material to provide the catalyst material includes heating the precatalyst material at a temperature from about 300° C. to about 500° C. For example, heating the precatalyst material to provide the catalyst material can include heating the precatalyst material at a temperature from about 350° C. to about 450° C. In some embodiments, heating the precatalyst material to provide the catalyst material includes heating the precatalyst material at a temperature of about 350° C. to about 375° C., about 375° C. to about 400° C., about 400° C. to about 425° C., or about 425° C. to about 450° C.

Further, heating the precatalyst material to provide the catalyst material can include heating the precatalyst material in the presence of air, an oxidizing atmosphere, an inert atmosphere, or a combination thereof. In some embodiments, heating the precatalyst material to provide the catalyst material includes heating the precatalyst material the presence of air.

In some embodiments, after the catalyst material is prepared, the catalyst material can be treated with a gas that includes ethane, oxygen, ethylene, or a combination thereof. For example, the catalyst material can be treated with a gas that includes ethane, oxygen, ethylene, or a combination thereof in an oxidative dehydrogenation reactor.

In some embodiments, the catalyst material is treated with a gas including ethane, oxygen, ethylene, or a combination thereof at an elevated temperature. For example, the catalyst material can be treated with a gas including ethane, oxygen, ethylene, or a combination thereof at a temperature from about 100° C. to about 500° C., about 200° C. to about 450° C., or about 300° C. to about 400° C. In some embodiments, the catalyst material is treated with a gas including ethane, oxygen, ethylene, or a combination thereof for about 6 hours to about 144 hours or about 18 hours to about 72 hours. In some embodiments, the catalyst material is treated with the gas including ethane, oxygen, ethylene, or combination thereof in an oxidative dehydrogenation reactor.

Also provided herein is a catalyst material that includes molybdenum, vanadium, oxygen, and aluminum. The molar ratio of molybdenum to vanadium in the catalyst material is from 1:0.30 to 1:0.45. The molar ratio of molybdenum to aluminum is from 1:3.25 to 1:5.5.

In some embodiments, the catalyst material is characterized by having at least five XRD diffraction peaks (2θ degrees) chosen from 6.7±0.2, 7.9±0.2, 9.1±0.2, 10.9±0.2, 13.0±0.2, 14.0±0.2, 22.1±0.2, 26.3±0.2, 26.8±0.2, 27.3±0.2, 28.3±0.2, 30.6±0.2, 31.5±0.2, and 45.2±0.2 wherein the XRD is obtained using CuKα radiation.

In some embodiments, the catalyst material is prepared by a method that includes preparing an aqueous mixture that includes (i) a catalyst including molybdenum, vanadium, and oxygen; (ii) a boehmite, and (iii) a water. The weight ratio of the catalyst to boehmite in the aqueous mixture can be from 3:5 to 3:8. For example, the weight ratio of the catalyst to boehmite in the aqueous mixture can be about 3:6 or about 3:7. The boehmite can be CATAPAL® B, VERSAL™ 250, or PB 250 alumina. The molar ratio of molybdenum to vanadium in the catalyst can be from 1:0.30 to 1:0.55. The method can further include removing a substantial amount of the water (e.g., from about 50 wt. % to about 99 wt. %) from the aqueous mixture to provide a precatalyst material. Removing a substantial amount of water from the aqueous mixture can include heating the mixture at a temperature from about 50° C. to about 100° C. Additionally, the method can include heating the precatalyst material to provide the catalyst material. Heating the precatalyst material to provide the catalyst material can include heating the precatalyst material at a temperature from about 350° C. to about 450° C.

Also provided herein is a catalyst material that includes molybdenum, vanadium, oxygen, and aluminum. The molar ratio of molybdenum to vanadium in the catalyst material is from 1:0.25 to 1:0.50. The molar ratio of molybdenum to aluminum is from 1:3.8 to 1:4.4.

In some embodiments, the catalyst material is characterized by having at least five XRD diffraction peaks (2θ degrees) chosen from 6.7±0.2, 7.9±0.2, 9.1±0.2, 10.9±0.2, 13.0±0.2, 14.0±0.2, 22.1±0.2, 26.3±0.2, 26.8±0.2, 27.3±0.2, 28.3±0.2, 30.6±0.2, 31.5±0.2, and 45.2±0.2 wherein the XRD is obtained using CuKα radiation.

In some embodiments, the catalyst material is prepared by a method that includes preparing an aqueous mixture that includes (i) a catalyst including molybdenum, vanadium, and oxygen; (ii) a boehmite, and (iii) a water. The weight ratio of the catalyst to boehmite in the aqueous mixture can be from 3:5 to 3:8. For example, the weight ratio of the catalyst to boehmite can be about 3:6 or about 3:7. The boehmite can be CATAPAL® B, VERSAL™ 250, or PB 250 alumina. The molar ratio of molybdenum to vanadium in the catalyst can be from 1:0.30 to 1:0.55. The method can further include removing a substantial amount of the water (e.g. from about 50 wt. % to about 99 wt. %) from the aqueous mixture to provide a precatalyst material. Removing a substantial amount of water from the aqueous mixture to provide a precatalyst material can include heating the mixture at a temperature from about 50° C. to about 100° C. Additionally, the method can include heating the precatalyst material to provide the catalyst material. Heating the precatalyst material to provide the catalyst material can include heating the precatalyst material at a temperature from about 350° C. to about 450° C.

Also provided herein is a catalyst material that includes molybdenum, vanadium, oxygen, and aluminum. The molar ratio of molybdenum to vanadium in the catalyst material is from 1:0.25 to 1:0.50. The molar ratio of molybdenum to aluminum is from 1:3.5 to 1:4.8.

In some embodiments, the catalyst material is characterized by having at least five XRD diffraction peaks (2θ degrees) chosen from 6.7±0.2, 7.9±0.2, 9.1±0.2, 10.9±0.2, 13.0±0.2, 14.0±0.2, 22.1±0.2, 26.3±0.2, 26.8±0.2, 27.3±0.2, 28.3±0.2, 30.6±0.2, 31.5±0.2, and 45.2±0.2 wherein the XRD is obtained using CuKα radiation.

In some embodiments, the catalyst material is prepared by a method that includes preparing an aqueous mixture that includes (i) a catalyst including molybdenum, vanadium, and oxygen; (ii) a boehmite, and (iii) a water. The weight ratio of the catalyst to boehmite in the aqueous mixture can be from 3:5 to 3:8. For example, the weight ratio of the catalyst to boehmite can be about 3:6 or about 3:7. The boehmite can be CATAPAL® B, VERSAL™ 250, or PB 250 alumina. The molar ratio of molybdenum to vanadium in the catalyst can be from 1:0.30 to 1:0.55. The method can further include removing a substantial amount of the water (e.g. from about 50 wt. % to about 99 wt. %) from the aqueous mixture to provide a precatalyst material. Removing a substantial amount of water from the aqueous mixture to provide a precatalyst material can include heating the mixture at a temperature from about 50° C. to about 100° C. Additionally, the method can include heating the precatalyst material to provide the catalyst material. Heating the precatalyst material to provide the catalyst material can include heating the precatalyst material at a temperature from about 350° C. to about 450° C.

Also provided herein is a catalyst material that includes molybdenum, vanadium, oxygen, and aluminum. The molar ratio of molybdenum to vanadium in the catalyst material is from 1:0.25 to 1:0.50. The molar ratio of molybdenum to aluminum is from 1:4.8 to 1:5.2.

In some embodiments, the catalyst material is characterized by having at least five XRD diffraction peaks (2θ degrees) chosen from 6.7±0.2, 7.9±0.2, 9.1±0.2, 10.9±0.2, 13.0±0.2, 14.0±0.2, 22.1±0.2, 26.3±0.2, 26.8±0.2, 27.3±0.2, 28.3±0.2, 30.6±0.2, 31.5±0.2, and 45.2±0.2 wherein the XRD is obtained using CuKα radiation.

In some embodiments, the catalyst material is prepared by a method that includes preparing an aqueous mixture that includes (i) a catalyst including molybdenum, vanadium, and oxygen; (ii) a boehmite, and (iii) a water. The weight ratio of the catalyst to boehmite in the aqueous mixture can be from 3:5 to 3:8. For example, the weight ratio of the catalyst to boehmite can be about 3:6 or about 3:7. The boehmite can be CATAPAL® B, VERSAL™ 250, or PB 250 alumina. The molar ratio of molybdenum to vanadium in the catalyst can be from 1:0.30 to 1:0.55. The method can further include removing a substantial amount of the water (e.g. from about 50 wt. % to about 99 wt. %) from the aqueous mixture to provide a precatalyst material. Removing a substantial amount of water from the aqueous mixture to provide a precatalyst material can include heating the mixture at a temperature from about 50° C. to about 100° C. Additionally, the method can include heating the precatalyst material to provide the catalyst material. Heating the precatalyst material to provide the catalyst material can include heating the precatalyst material at a temperature from about 350° C. to about 450° C.

Also provided herein is a catalyst material that includes molybdenum, vanadium, oxygen, and aluminum. The molar ratio of molybdenum to vanadium in the catalyst material is from 1:0.30 to 1:0.45. The molar ratio of molybdenum to aluminum is from 1:2.5 to 1:3.5.

In some embodiments, the catalyst material is characterized by having at least five XRD diffraction peaks (2θ degrees) chosen from 6.7±0.2, 7.9±0.2, 9.1±0.2, 10.9±0.2, 13.0±0.2, 14.0±0.2, 22.1±0.2, 26.3±0.2, 26.8±0.2, 27.3±0.2, 28.3±0.2, 30.6±0.2, 31.5±0.2, and 45.2±0.2 wherein the XRD is obtained using CuKα radiation.

In some embodiments, the catalyst material is prepared by a method that includes preparing an aqueous mixture that includes (i) a catalyst including molybdenum, vanadium, and oxygen; (ii) a boehmite, and (iii) a water. The weight ratio of the catalyst to boehmite in the aqueous mixture can be from 3:2 to 3:4. For example, the weight ratio of the catalyst to boehmite can be about 3:4. The boehmite can be CATAPAL® B, VERSAL™ 250, or PB 250 alumina. The molar ratio of molybdenum to vanadium in the catalyst can be from 1:0.30 to 1:0.55. The method can further include removing a substantial amount of the water (e.g. from about 50 wt. % to about 99 wt. %) from the aqueous mixture to provide a precatalyst material. Removing a substantial amount of water from the aqueous mixture to provide a precatalyst material can include heating the mixture at a temperature from about 50° C. to about 100° C. Additionally, the method can include heating the precatalyst material to provide the catalyst material. Heating the precatalyst material to provide the catalyst material can include heating the precatalyst material at a temperature from about 350° C. to about 450° C.

Also provided herein is a catalyst material that includes molybdenum, vanadium, oxygen, and aluminum. The molar ratio of molybdenum to vanadium in the catalyst material is from 1:0.30 to 1:0.45. The molar ratio of molybdenum to aluminum is from 1:2.5 to 1:3.5.

In some embodiments, the catalyst material is characterized by having at least five XRD diffraction peaks (2θ degrees) chosen from 6.7±0.2, 7.9±0.2, 9.1±0.2, 10.9±0.2, 13.0±0.2, 14.0±0.2, 22.1±0.2, 26.3±0.2, 26.8±0.2, 27.3±0.2, 28.3±0.2, 30.6±0.2, 31.5±0.2, and 45.2±0.2 wherein the XRD is obtained using CuKα radiation.

In some embodiments, the catalyst material is prepared by a method that includes preparing an aqueous mixture that includes (i) a catalyst including molybdenum, vanadium, and oxygen; (ii) a boehmite, and (iii) a water. The weight ratio of the catalyst to boehmite in the aqueous mixture can be from 3:3 to 3:5. For example, the weight ratio of the catalyst to boehmite can be about 3:4. The boehmite can be CATAPAL® B, VERSAL™ 250, or PB 250 alumina. The molar ratio of molybdenum to vanadium in the catalyst can be from 1:0.30 to 1:0.55. The method can further include removing a substantial amount of the water (e.g. from about 50 wt. % to about 99 wt. %) from the aqueous mixture to provide a precatalyst material. Removing a substantial amount of water from the aqueous mixture to provide a precatalyst material can include heating the mixture at a temperature from about 50° C. to about 100° C. Additionally, the method can include heating the precatalyst material to provide the catalyst material. Heating the precatalyst material to provide the catalyst material can include heating the precatalyst material at a temperature from about 350° C. to about 450° C.

Also provided herein is a catalyst material that includes molybdenum, vanadium, oxygen, and aluminum. The molar ratio of molybdenum to vanadium in the catalyst material is from 1:0.35 to 1:0.45. The molar ratio of molybdenum to aluminum is from 1:2.9 to 1:3.1.

In some embodiments, the catalyst material is characterized by having at least five XRD diffraction peaks (2θ degrees) chosen from 6.7±0.2, 7.9±0.2, 9.1±0.2, 10.9±0.2, 13.0±0.2, 14.0±0.2, 22.1±0.2, 26.3±0.2, 26.8±0.2, 27.3±0.2, 28.3±0.2, 30.6±0.2, 31.5±0.2, and 45.2±0.2 wherein the XRD is obtained using CuKα radiation.

In some embodiments, the catalyst material is prepared by a method that includes preparing an aqueous mixture that includes (i) a catalyst including molybdenum, vanadium, and oxygen; (ii) a boehmite, and (iii) a water. The weight ratio of the catalyst to boehmite in the aqueous mixture can be from 3:3 to 3:5. For example, the weight ratio of the catalyst to boehmite can be about 3:4. The boehmite can be CATAPAL® B, VERSAL™ 250, or PB 250 alumina. The molar ratio of molybdenum to vanadium in the catalyst can be from 1:0.30 to 1:0.55. The method can further include removing a substantial amount of the water (e.g. from about 50 wt. % to about 99 wt. %) from the aqueous mixture to provide a precatalyst material. Removing a substantial amount of water from the aqueous mixture to provide a precatalyst material can include heating the mixture at a temperature from about 50° C. to about 100° C. Additionally, the method can include heating the precatalyst material to provide the catalyst material. Heating the precatalyst material to provide the catalyst material can include heating the precatalyst material at a temperature from about 350° C. to about 450° C.

Catalyst Materials Including Molybdenum, Vanadium, Oxygen, Aluminum, and Iron

Also provided herein is an oxidative dehydrogenation catalyst material that includes molybdenum, vanadium, oxygen, aluminum, and iron. The molar ratio of molybdenum to vanadium is from 1:0.1 to 1:0.5. The molar ratio of molybdenum to iron is from 1:0.25 to 1:5.5. The molar ratio of molybdenum to aluminum is from 1:1.5 to 1:6.0. Further, oxygen is present at least in an amount to satisfy the valency of any present metal oxides.

In some embodiments, the molar ratio of molybdenum to vanadium in the catalyst material is from 1:0.25 to 1:0.50. In some embodiments, the molar ratio of molybdenum to vanadium in the catalyst material is from 1:0.30 to 1:0.45. For example, the molar ratio of molybdenum to vanadium can be from 1:0.30 to 1:0.35 or from 1:0.35 to 1:0.45. In some embodiments, the molar ratio of molybdenum to vanadium is from 1:0.37 to 1:0.41.

In some embodiments, the catalyst material does not include niobium, tellurium, or both.

In some embodiments, at least a portion of the molybdenum and vanadium in the catalyst material can be present as a mixed metal oxide having the empirical formula:

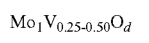

$$Mo_1V_{0.25\text{-}0.50}O_d$$

wherein d is a number to satisfy the valence of the oxide.

In some embodiments, the molar ratio of molybdenum to iron is from 1:0.25 to 1:1.0 and the molar ratio of molybdenum to aluminum is from 1:3.5 to 1:5.5. For example, the molar ratio of molybdenum to iron can be from 1:0.25 to 1:0.75 and the molar ratio of molybdenum to aluminum can be from 1:3.75 to 1:5.25. In some embodiments, the molar ratio of molybdenum to iron is from 1:0.35 to 1:0.65 and the molar ratio of molybdenum to aluminum is from 1:3.75 to 1:5.25. In some embodiments, the molar ratio of molybdenum to iron is from about 1:0.35 to about 1:0.45 and the molar ratio of molybdenum to aluminum is from 1:3.9 to 1:4.0. In some embodiments the molar ratio of molybdenum to iron is about 1:0.55 to about 0:65, and the molar ratio of molybdenum to aluminum is from 1:4.95 to 1:5.05.

In some embodiments, the molar ratio of molybdenum to vanadium is from 1:0.30 to 1:0.45, the molar ratio of molybdenum to iron is from 1:0.25 to 1:1, and the molar ratio of molybdenum to aluminum is from 1:3.5 to 1:5.5. For example, the molar ratio of molybdenum to vanadium can be from 1:0.30 to 1:0.45, the molar ratio of molybdenum to iron can be from 1:0.25 to 1:0.75, and the molar ratio of molybdenum to aluminum can be from 1:3.75 to 1:5.25. In some embodiments, the molar ratio of molybdenum to vanadium is from 1:0.30 to 1:0.45, the molar ratio of molybdenum to iron is from 1:0.35 to 1:0.65, and the molar ratio of molybdenum to aluminum is from 1:3.75 to 1:5.25.

In some embodiments, the molar ratio of molybdenum to vanadium is from 1:0.30 to 1:0.35, the molar ratio of molybdenum to iron is from about 1:0.35 to about 1:0.45, and the molar ratio of molybdenum to aluminum is from 1:3.9 to 1:4.0. In some embodiments, the molar ratio of molybdenum to vanadium is from 1:0.35 to 1:0.45, the molar ratio of molybdenum to iron is about 1:0.55 to about 0:65, and the molar ratio of molybdenum to aluminum is from 1:4.95 to 1:5.05. For example, the molar ratio of molybdenum to vanadium can be from 1:0.37 to 1:0.41, the molar ratio of molybdenum to iron can be from about 1:0.55 to about 0:65, and the molar ratio of molybdenum to aluminum can be from 1:4.95 to 1:5.05.

In some embodiments, the molar ratio of molybdenum to iron is from 1:1.3 to 1:2.2 and the molar ratio of molybdenum to aluminum is from 1:2.0 to 1:4.0. For example, the molar ratio of molybdenum to iron can be from 1:1.6 to 1:2.0 and the molar ratio of molybdenum to aluminum can be from 1:2.5 to 1:3.5. In some embodiments, the molar ratio of molybdenum to iron is from about 1:1.80 to about 1:1.90 and the molar ratio of molybdenum to aluminum is from 1:2.9 to 1:3.1.

In some embodiments, the molar ratio of molybdenum to vanadium is from 1:0.35 to 1:0.45, the molar ratio of molybdenum to iron is from 1:1.3 to 1:2.2, and the molar ratio of molybdenum to aluminum is from 1:2.0 to 1:4.0. For example, the molar ratio of molybdenum to vanadium can be from 1:0.35 to 1:0.45, the molar ratio of molybdenum to iron can be from 1:1.6 to 1:2.0, and the molar ratio of molybdenum to aluminum can be from 1:2.5 to 1:3.5. In some embodiments, the molar ratio of molybdenum to vanadium is from 1:0.35 to 1:0.45, the molar ratio of molybdenum to iron is from about 1:1.80 to about 1:1.90, and the molar ratio of molybdenum to aluminum is from 1:2.9 to 1:3.1. For example, the molar ratio of molybdenum to vanadium can be from 1:0.37 to 1:0.41, the molar ratio of molybdenum to iron is from about 1:1.80 to about 1:1.90, and the molar ratio of molybdenum to aluminum is from 1:2.9 to 1:3.1.

In some embodiments, the molar ratio of molybdenum to iron is from 1:2.2 to 1:2.8 and the molar ratio of molybdenum to aluminum is from 1:1.8 to 1:2.4. For example, the molar ratio of molybdenum to iron can be from 1:2.4 to 1:2.6 and the molar ratio of molybdenum to aluminum can be from 1:1.9 to 1:2.3. In some embodiments, the molar ratio of molybdenum to iron is from about 1:2.45 to about 1:2.6 and the molar ratio of molybdenum to aluminum is from 1:2.0 to 1:2.2.

In some embodiments, the molar ratio of molybdenum to vanadium is from 1:0.35 to 1:0.45, the molar ratio of molybdenum to iron is from is from 1:2.2 to 1:2.8, and the molar ratio of molybdenum to aluminum is from 1:1.8 to 1:2.4. For example, the molar ratio of molybdenum to vanadium can be from 1:0.35 to 1:0.45, the molar ratio of molybdenum to iron can be from 1:2.4 to 1:2.6, and the molar ratio of molybdenum to aluminum can be from 1:1.9 to 1:2.3.

In some embodiments, the catalyst material is characterized by having at least five XRD diffraction peaks (2θ degrees) chosen from 6.6±0.2, 7.8±0.2, 9.0±0.2, 10.8±0.2, 13.0±0.2, 14.0±0.2, 22.1±0.2, 26.3±0.2, 26.8±0.2, 27.3±0.2, 28.2±0.2, 29.3±0.2, 30.6±0.2, 31.4±0.2, 33.1±0.2, 35.5±0.2, 40.8±0.2, 45.1±0.2, 54.0±0.2, and 64.0±0.2 wherein the XRD is obtained using CuKα radiation.

In some embodiments, the catalyst material is characterized by having at least ten XRD diffraction peaks (2θ degrees) chosen from 6.6±0.2, 7.8±0.2, 9.0±0.2, 10.8±0.2, 13.0±0.2, 14.0±0.2, 22.1±0.2, 26.3±0.2, 26.8±0.2, 27.3±0.2, 28.2±0.2, 29.3±0.2, 30.6±0.2, 31.4±0.2, 33.1±0.2, 35.5±0.2, 40.8±0.2, 45.1±0.2, 54.0±0.2, and 64.0±0.2 wherein the XRD is obtained using CuKα radiation.

In some embodiments, the catalyst material is characterized by having at least fifteen XRD diffraction peaks (2θ degrees) chosen from 6.6±0.2, 7.8±0.2, 9.0±0.2, 10.8±0.2, 13.0±0.2, 14.0±0.2, 22.1±0.2, 26.3±0.2, 26.8±0.2, 27.3±0.2, 28.2±0.2, 29.3±0.2, 30.6±0.2, 31.4±0.2, 33.1±0.2, 35.5±0.2, 40.8±0.2, 45.1±0.2, 54.0±0.2, and 64.0±0.2 wherein the XRD is obtained using CuKα radiation.

In some embodiments, the catalyst material is characterized by having XRD diffraction peaks (2θ degrees) at 6.6±0.2, 7.8±0.2, 9.0±0.2, 10.8±0.2, 13.0±0.2, 14.0±0.2, 22.1±0.2, 26.3±0.2, 26.8±0.2, 27.3±0.2, 28.2±0.2, 29.3±0.2, 30.6±0.2, 31.4±0.2, 33.1±0.2, 35.5±0.2, 40.8±0.2, 45.1±0.2, 54.0±0.2, and 64.0±0.2 wherein the XRD is obtained using CuKα radiation.

In some embodiments, the catalyst material is characterized by having at least five XRD diffraction peaks (2θ degrees) chosen from 6.6±0.2, 7.8±0.2, 9.0±0.2, 10.8±0.2, 13.0±0.2, 14.0±0.2, 22.1±0.2, 26.3±0.2, 26.8±0.2, 27.3±0.2, 28.2±0.2, 29.3±0.2, 30.6±0.2, 31.4±0.2, 33.1±0.2, 35.5±0.2, 40.8±0.2, 45.1±0.2, 54.0±0.2, and 64.0±0.2 and at least one broad peak chosen from 13.9±0.2, 28.2±0.2, 38.5±0.2, 49.1±0.2, 55.7±0.2, and 65.0±0.2, wherein the XRD is obtained using CuKα radiation.

In some embodiments, the catalyst material is characterized by having at least ten XRD diffraction peaks (2θ degrees) chosen from 6.6±0.2, 7.8±0.2, 9.0±0.2, 10.8±0.2, 13.0±0.2, 14.0±0.2, 22.1±0.2, 26.3±0.2, 26.8±0.2, 27.3±0.2, 28.2±0.2, 29.3±0.2, 30.6±0.2, 31.4±0.2, 33.1±0.2, 35.5±0.2, 40.8±0.2, 45.1±0.2, 54.0±0.2, and 64.0±0.2 and at least one broad peak chosen from 13.9±0.2, 28.2±0.2, 38.5±0.2, 49.1±0.2, 55.7±0.2, and 65.0±0.2, wherein the XRD is obtained using CuKα radiation.

In some embodiments, the catalyst material is characterized by having at least fifteen XRD diffraction peaks (2θ degrees) chosen from 6.6±0.2, 7.8±0.2, 9.0±0.2, 10.8±0.2, 13.0±0.2, 14.0±0.2, 22.1±0.2, 26.3±0.2, 26.8±0.2, 27.3±0.2, 28.2±0.2, 29.3±0.2, 30.6±0.2, 31.4±0.2, 33.1±0.2, 35.5±0.2, 40.8±0.2, 45.1±0.2, 54.0±0.2, and 64.0±0.2 and at least one broad peak chosen from 13.9±0.2, 28.2±0.2, 38.5±0.2, 49.1±0.2, 55.7±0.2, and 65.0±0.2, wherein the XRD is obtained using CuKα radiation.

In some embodiments, the catalyst material is characterized by having XRD diffraction peaks (2θ degrees) at 6.6±0.2, 7.8±0.2, 9.0±0.2, 10.8±0.2, 13.0±0.2, 14.0±0.2, 22.1±0.2, 26.3±0.2, 26.8±0.2, 27.3±0.2, 28.2±0.2, 29.3±0.2, 30.6±0.2, 31.4±0.2, 33.1±0.2, 35.5±0.2, 40.8±0.2, 45.1±0.2, 54.0±0.2, and 64.0±0.2 and at least one broad peak chosen from 13.9±0.2, 28.2±0.2, 38.5±0.2, 49.1±0.2, 55.7±0.2, and 65.0±0.2, wherein the XRD is obtained using CuKα radiation.

In some embodiments, the catalyst material has a BET surface area from 50 $m^2/g$ to 250 $m^2/g$. For example, the catalyst material can have a BET surface area from 75 $m^2/g$ to 225 $m^2/g$, 90 $m^2/g$ to 175 $m^2/g$ or from 90 $m^2/g$ to 175 $m^2/g$. In some embodiments, the catalyst material has a BET surface area from 90 $m^2/g$ to 130 $m^2/g$ or from 130 $m^2/g$ to 170 $m^2/g$.

In some embodiments, the catalyst material has a pore volume from 0.10 $cm^3/g$ to 1.00 $cm^3/g$. For example, the catalyst material can have a pore volume from 0.10 $cm^3/g$ to 0.50 $cm^3/g$ or from 0.10 $cm^3/g$ to 0.40 $cm^3/g$. In some embodiments, the catalyst material has a pore volume from 0.15 $cm^3/g$ to 0.25 $cm^3/g$ or from 0.25 $cm^3/g$ to 0.40 $cm^3/g$.

In some embodiments, the catalyst material has a 35% conversion temperature from about 300° C. to about 400° C. For example, the catalyst material can have a 35% conversion temperature from about 300° C. to about 350° C. In some embodiments, the catalyst material has a 35% conversion temperature from about 315° C. to about 335° C.

In some embodiments, the catalyst material has a selectivity to ethylene from about 65% to 99%. For example, the catalyst material can have a selectivity to ethylene from about 75% to 95%. In some embodiments, the catalyst material has a selectivity to ethylene from about 77% to about 85%.

In some embodiments, the catalyst material has a selectivity to acetic acid of less than 15 wt. % in a process for the oxidative dehydrogenation of ethane. For example, the catalyst material can have a selectivity to acetic acid of about 1 wt. % to about 15 wt. %, about 3 wt. % to about 12 wt. %, or about 7 wt. % to about 12 wt. % in a process for the oxidative dehydrogenation of ethane. In some embodiments, the catalyst material has a selectivity to acetic acid of about 7 wt. %, 8 wt. %, 9 wt. %, 10 wt. %, 11 wt. %, 12 wt. % or about 13 wt. % in a process for the oxidative dehydrogenation of ethane. Selectivity to acetic acid can be determined as described in the Example section.

In some embodiments, at least a portion of the iron present in the catalyst material can be present as iron(III) (i.e., $Fe^{3+}$). In some embodiments, at least a portion of the iron in the catalyst material can be present as amorphous iron. In some embodiments, at least a portion of the iron present in the catalyst material is present as an iron oxide, an iron oxide hydroxide, or a combination thereof.

When at least a portion of the iron in the catalyst material is present as an iron oxide, the iron oxide can include an iron oxide selected from hematite, maghemite, magnetite, or a combination thereof. In some embodiments, at least a portion of the iron in the catalyst material is present as hematite.

In some embodiments, at least a portion of the iron in the catalyst material is present as a hematite-like iron.

When at least a portion of the iron in the catalyst material is present as an iron oxide hydroxide, the iron oxide hydroxide can include an iron oxide hydroxide selected from goethite, an akaganeite, a lepidocrocite, or a combination thereof. In some embodiments, at least a portion of the iron in the catalyst material is present as goethite.

In some embodiments, at least a portion of the iron in the catalyst material is present as goethite and at least a portion of the iron in the catalyst material is present as hematite.

In some embodiments, at least a portion of the aluminum in the catalyst material is present as an aluminum oxide. In some embodiments, the aluminum oxide is an aluminum oxide hydroxide. The aluminum oxide hydroxide can include a gibbsite, a bayerite, a boehmite, or a combination thereof. In some embodiments, at least a portion of the aluminum in the catalyst material is present as a boehmite. In some embodiments, at least a portion of the aluminum in the catalyst material is present as gamma alumina.

In some embodiments, at least a portion of the iron in the catalyst material is present as goethite and at least a portion of the aluminum in the catalyst material is present as a boehmite. In some embodiments, at least a portion of the iron in the catalyst material is present as goethite, at least a portion of the iron in the catalyst material is present as hematite, and at least a portion of the aluminum in the catalyst material is present as a boehmite.

The catalyst materials provided herein that include molybdenum, vanadium, oxygen, iron, and aluminum can prepared by a method that includes preparing an aqueous mixture including (i) a catalyst that includes molybdenum, vanadium, and oxygen; (ii) an aluminum compound; (iii) an iron compound; and (iv) a water. The method further includes removing a substantial amount of the water from the mixture to provide a precatalyst material. The method also includes heating the precatalyst material to provide the catalyst material.

In some embodiments, the method further includes preparing the catalyst including molybdenum, vanadium, and oxygen.

In some embodiments, the molar ratio of molybdenum to vanadium in the provided catalyst is from 1:0.25 to 1:0.6. For example, the molar ratio of molybdenum to vanadium in the catalyst can be from 1:30 to 1:35 or from 1:0.35 to 1:0.55. In some embodiments, the molar ratio of molybdenum to vanadium in the provided catalyst is from 1:0.35 to 1:0.42. In some embodiments, the molar ratio of molybdenum to vanadium in the provided catalyst is from 1:0.40 to 1:0.49.

In some embodiments, the provided catalyst includes a mixed metal oxide having the empirical formula:

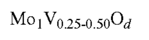

wherein d is a number to satisfy the valence of the oxide.

In some embodiments, the iron compound in the aqueous mixture including the catalyst, the iron compound, the aluminum compound, and the water includes an iron(III) compound. In some embodiments, the iron compound in the aqueous mixture includes an iron oxide, an iron oxide hydroxide, or a combination thereof. The iron oxide can include hematite, maghemite, magnetite, or a combination thereof. In some embodiments, the iron compound in the aqueous mixture of the catalyst, the iron compound, the aluminum compound, and the water includes goethite. In some embodiments, the iron compound in the aqueous mixture of the catalyst, the iron compound, the aluminum compound, and the water includes goethite and hematite.

In some embodiments, the aluminum compound in the mixture including the catalyst, the iron compound, the aluminum compound, and the water includes an aluminum oxide. In some embodiments, the aluminum oxide includes an aluminum oxide hydroxide. The aluminum oxide hydroxide can include a gibbsite, a bayerite, a boehmite, or a combination thereof. In some embodiments, the aluminum compound used in the aqueous mixture includes a boehmite. In some embodiments, the boehmite includes a pseudoboehmite such as VERSAL™ 250. In some embodiments, the boehmite includes CATAPAL® B. In some embodiments, the boehmite includes PB 250 alumina.

In some embodiments, the iron compound in the aqueous mixture includes goethite and the aluminum compound includes a boehmite (e.g., VERSAL™ 250, CATAPAL® B, or both). In some embodiments, the iron compound in the aqueous mixture includes goethite, hematite, or both, and the aluminum compound includes a boehmite (e.g., VERSAL™ 250, CATAPAL® B, or both).

Removing a substantial amount of water from the aqueous mixture including the catalyst, the iron compound, the aluminum compound, and the water to provide a precatalyst material can include removing from about 50 wt. % to about 99 wt. % of the water. For example, about 50 wt. % to about 75 wt. % or about 75 wt. % to about 99 wt. % of the water can be removed to provide the precatalyst material. For example, enough water can be removed from the aqueous mixture such that the provided catalyst material has a paste-like consistency.

In some embodiments, removing a substantial amount of the water from the aqueous mixture of the catalyst, the iron compound, the aluminum compound, and the water to provide a precatalyst material includes heating the aqueous mixture at a temperature from about 50° C. to about 280° C., about 50° C. to about 250° C., or about 50° C. to about 100° C. For example, the aqueous mixture can be heated at a temperature of about 80° C.

In some embodiments, heating the precatalyst material to provide the catalyst material includes heating the precatalyst material at a temperature from about 300° C. to about 500° C. For example, heating the precatalyst material to provide the catalyst material can include heating the precatalyst material at a temperature from about 350° C. to about 450° C. In some embodiments, heating the precatalyst material to provide the catalyst material includes heating the precatalyst material at a temperature of about 350° C. to about 375° C., about 375° C. to about 400° C., about 400° C. to about 425° C., or about 425° C. to about 450° C.

Further, heating the precatalyst material to provide the catalyst material can include heating the precatalyst material in the presence of air, an oxidizing atmosphere, an inert atmosphere, or a combination thereof. In some embodiments, heating the precatalyst material to provide the catalyst material includes heating the precatalyst material the presence of air.

In some embodiments, after the catalyst material is prepared, the catalyst material can be treated with a gas that includes ethane, oxygen, ethylene, or a combination thereof. For example, the catalyst material can be treated with a gas that includes ethane, oxygen, ethylene, or a combination thereof in an oxidative dehydrogenation reactor.

In some embodiments, the catalyst material is treated with the gas including ethane, oxygen, ethylene, or a combination thereof at an elevated temperature. For example, the catalyst material can be treated with the gas at a temperature from about 100° C. to about 500° C., about 200° C. to about 450° C., or about 300° C. to about 400° C. In some embodiments, the catalyst material is treated with the gas for about 6 hours about 144 hours or about 18 hours to about 72 hours. In some embodiments, the catalyst material is treated with the gas including ethane, oxygen, ethylene, or combination thereof in an oxidative dehydrogenation reactor.

Also provided herein is a catalyst material that includes molybdenum, vanadium, oxygen, iron, and aluminum. The molar ratio of molybdenum to vanadium in the catalyst material is from 1:0.30 to 1:0.45. The molar ratio of molybdenum to iron is from 0.25 to 0.75. The molar ratio of molybdenum to aluminum is from 1:3.75 to 1:5.25.

The catalyst material is prepared by a method that includes preparing an aqueous mixture that includes (i) a catalyst including molybdenum, vanadium, and oxygen; (ii) goethite; (iii) a boehmite; and (iv) a water. The weight ratio of the catalyst to goethite in the aqueous mixture can be from 3:0.5 to 3:1.5. For example, the weight ratio of the catalyst to goethite can be about 3:1. The weight ratio of catalyst to boehmite in the aqueous mixture can be from 3:5 to 3:7. For example, the weight ratio of the catalyst to boehmite can be about 3:6. The boehmite can be CATAPAL® B, VERSAL™ 250, or PB 250 alumina. The molar ratio of molybdenum to vanadium in the catalyst used to prepare the aqueous mixture can be from 1:0.30 to 1:0.55. The method can further include removing a substantial amount of the water (e.g., from about 50 wt. % to about 99 wt. %) from the aqueous mixture to provide a precatalyst material. Removing a substantial amount of water from the aqueous mixture to provide a precatalyst material can include heating the aqueous mixture at a temperature from about 50° C. to about 100° C. Additionally, the method can include heating the precatalyst material to provide the catalyst material. Heating the precatalyst material to provide the catalyst material can include heating the precatalyst material at a temperature from about 350° C. to about 450° C.

In some embodiments, the catalyst material is characterized by having at least five XRD diffraction peaks (2θ degrees) chosen from 6.6±0.2, 7.8±0.2, 9.0±0.2, 10.8±0.2, 13.0±0.2, 14.0±0.2, 22.1±0.2, 26.3±0.2, 26.8±0.2, 27.3±0.2, 28.2±0.2, 29.3±0.2, 30.6±0.2, 31.4±0.2, 33.1±0.2, 35.5±0.2, 40.8±0.2, 45.1±0.2, 54.0±0.2, and 64.0±0.2 wherein the XRD is obtained using CuKα radiation.

In some embodiments, the catalyst material is treated with a gas that includes ethane, oxygen, ethylene, or a combination thereof at a temperature from about 300° C. to about 400° C. In some embodiments, the catalyst material is treated with a gas that includes ethane, oxygen, ethylene, or a combination thereof for a time of about 18 hours to about 72 hours. The gas treatment can convert at least a portion of the goethite to hematite.

Also provided herein is a catalyst material that includes molybdenum, vanadium, oxygen, iron, and aluminum. The molar ratio of molybdenum to vanadium in the catalyst material is from 1:0.30 to 1:0.40. The molar ratio of molybdenum to iron is from 0.35 to 0.50. The molar ratio of molybdenum to aluminum is from 1:3.8 to 1:4.3.

The catalyst material is prepared by a method that includes preparing an aqueous mixture that includes (i) a catalyst including molybdenum, vanadium, and oxygen; (ii) goethite; (iii) a boehmite; and (iv) a water. The weight ratio of the catalyst to goethite in the aqueous mixture can be about 3:0.08. The weight ratio of catalyst to boehmite in the aqueous mixture can about 3:6. The boehmite can be CATAPAL® B, VERSAL™ 250, or PB 250 alumina. The molar ratio of molybdenum to vanadium in the catalyst used to prepare the aqueous mixture can be from 1:0.30 to 1:0.55. The method can further include removing a substantial amount of the water (e.g., from about 50 wt. % to about 99 wt. %) from the aqueous mixture to provide a precatalyst material. Removing a substantial amount of water from the aqueous mixture to provide a precatalyst material can include heating the aqueous mixture at a temperature from about 50° C. to about 100° C. Additionally, the method can include heating the precatalyst material to provide the catalyst material. Heating the precatalyst material to provide the catalyst material can include heating the precatalyst material at a temperature from about 350° C. to about 450° C.

In some embodiments, the catalyst material is characterized by having at least five XRD diffraction peaks (2θ degrees) chosen from 6.6±0.2, 7.8±0.2, 9.0±0.2, 10.8±0.2, 13.0±0.2, 14.0±0.2, 22.1±0.2, 26.3±0.2, 26.8±0.2, 27.3±0.2, 28.2±0.2, 29.3±0.2, 30.6±0.2, 31.4±0.2, 33.1±0.2, 35.5±0.2, 40.8±0.2, 45.1±0.2, 54.0±0.2, and 64.0±0.2 wherein the XRD is obtained using CuKα radiation.

In some embodiments, the catalyst material is treated with a gas that includes ethane, oxygen, ethylene, or a combination thereof at a temperature from about 300° C. to about 400° C. In some embodiments, the catalyst material is treated with a gas that includes ethane, oxygen, ethylene, or a combination thereof for a time of about 18 hours to about 72 hours. The gas treatment can convert at least a portion of the goethite to hematite.

Also provided herein is a catalyst material that includes molybdenum, vanadium, oxygen, iron, and aluminum. The molar ratio of molybdenum to vanadium in the catalyst material is from 1:0.35 to 1:0.45. The molar ratio of molybdenum to iron is from 1:0.55 to 1:0.65. The molar ratio of molybdenum to aluminum is from 1:4.95 to 1:5.05.

The catalyst material is prepared by a method that includes preparing an aqueous mixture that includes (i) a catalyst including molybdenum, vanadium, and oxygen; (ii) goethite; (iii) a boehmite; and (iv) a water. The weight ratio of the catalyst to goethite in the aqueous mixture can be from 3:0.8 to 3:1.2. For example, the weight ratio of the catalyst to goethite can be about 3:1. The weight ratio of catalyst to boehmite in the aqueous mixture can be from 3:5.5 to 3:6.5. For example, the weight ratio of the catalyst to boehmite can be about 3:6. The boehmite can be CATAPAL® B, VERSAL™ 250, or PB 250 alumina. The molar ratio of molybdenum to vanadium in the catalyst used to prepare the aqueous mixture can be from 1:0.30 to 1:0.55. For example, the molar ratio of molybdenum to vanadium in the catalyst used to prepare the aqueous mixture can be from about 1:0.42 to about 1:0.47. The method can further include removing a substantial amount of the water (e.g., from about 50 wt. % to about 99 wt. % of the water) from the aqueous mixture to provide a precatalyst material. Removing a substantial amount of water from the aqueous mixture to provide a precatalyst material can include heating the aqueous mixture at a temperature from about 50° C. to about 100° C. Additionally, the method can include heating the precatalyst material to provide the catalyst material. Heating the precatalyst material to provide the catalyst material can include heating the precatalyst material at a temperature from about 350° C. to about 450° C.

In some embodiments, the catalyst material is treated with a gas that includes ethane, oxygen, ethylene, or a combination thereof at a temperature from about 300° C. to about 400° C. In some embodiments, the catalyst material is treated with a gas that includes ethane, oxygen, ethylene, or a combination thereof for a time of about 18 hours to about 72 hours. The gas treatment can convert at least a portion of the goethite to hematite.

In some embodiments, the catalyst material is characterized by having at least five XRD diffraction peaks (2θ degrees) chosen from 6.6±0.2, 7.8±0.2, 9.0±0.2, 10.8±0.2, 13.0±0.2, 14.0±0.2, 22.1±0.2, 26.3±0.2, 26.8±0.2, 27.3±0.2, 28.2±0.2, 29.3±0.2, 30.6±0.2, 31.4±0.2, 33.1±0.2, 35.5±0.2, 40.8±0.2, 45.1±0.2, 54.0±0.2, and 64.0±0.2 wherein the XRD is obtained using CuKα radiation.

Also provided herein is a catalyst material that includes molybdenum, vanadium, oxygen, iron, and aluminum. The molar ratio of molybdenum to vanadium in the catalyst material is from 1:0.35 to 1:0.45. The molar ratio of molybdenum to iron is from 1:1.6 to 1:2.0. The molar ratio of molybdenum to aluminum is from 1:2.5 to 1:3.5.

The catalyst material is prepared by a method that includes preparing an aqueous mixture that includes (i) a catalyst including molybdenum, vanadium, and oxygen; (ii) goethite; (iii) a boehmite; and (iv) a water. The weight ratio of the catalyst to goethite in the aqueous mixture can be from 3:2.5 to 3:3.5. For example, the weight ratio of the catalyst to goethite can be about 3:3. The weight ratio of catalyst to boehmite in the aqueous mixture can be from 3:35 to 3:4.5. For example, the weight ratio of the catalyst to boehmite can be about 3:4. The boehmite can be CATAPAL® B, VERSAL™ 250, or PB 250 alumina. The molar ratio of molybdenum to vanadium in the catalyst used to prepare the aqueous mixture can be from 1:0.30 to 1:0.55. For example, the molar ratio of molybdenum to vanadium in the catalyst used to prepare the aqueous mixture can be from about 1:0.42 to about 1:0.47. The method can further include removing a substantial amount of the water (e.g., from about 50 wt. % to about 99 wt. % of the water) from the aqueous mixture to provide a precatalyst material. Removing a substantial amount of water from the aqueous mixture to provide a precatalyst material can include heating the aqueous mixture at a temperature from about 50° C. to about 100° C. Additionally, the method can include heating the precatalyst material to provide the catalyst material. Heating the precatalyst material to provide the catalyst material can include heating the precatalyst material at a temperature from about 350° C. to about 450° C.

In some embodiments, the catalyst material is treated with a gas that includes ethane, oxygen, ethylene, or a combination thereof at a temperature from about 300° C. to about 400° C. In some embodiments, the catalyst material is treated with a gas that includes ethane, oxygen, ethylene, or a combination thereof for a time of about 18 hours to about 72 hours. The gas treatment can convert at least a portion of the goethite to hematite.

In some embodiments, the catalyst material is characterized by having at least five XRD diffraction peaks (2θ degrees) chosen from 6.6±0.2, 7.8±0.2, 9.0±0.2, 10.8±0.2, 13.0±0.2, 14.0±0.2, 22.1±0.2, 26.3±0.2, 26.8±0.2, 27.3±0.2, 28.2±0.2, 29.3±0.2, 30.6±0.2, 31.4±0.2, 33.1±0.2, 35.5±0.2, 40.8±0.2, 45.1±0.2, 54.0±0.2, and 64.0±0.2 wherein the XRD is obtained using CuKα radiation.

Also provided herein is a catalyst material that includes molybdenum, vanadium, oxygen, iron, and aluminum. The molar ratio of molybdenum to vanadium in the catalyst material is from 1:0.30 to 1:0.45. The molar ratio of molybdenum to iron is from 1:2.2 to 1:2.8. The molar ratio of molybdenum to aluminum is from 1:1.4 to 1:2.4.

The catalyst material is prepared by a method that includes preparing an aqueous mixture that includes (i) a catalyst including molybdenum, vanadium, and oxygen; (ii) goethite; (iii) a boehmite; and (iv) a water. The weight ratio of the catalyst to goethite in the aqueous mixture can be from 3:3.5 to 3:4.5. For example, the weight ratio of the catalyst to goethite can be about 3:4. The weight ratio of catalyst to boehmite in the aqueous mixture can be from 3:25 to 3:3.5. For example, the weight ratio of the catalyst to boehmite can be about 3:3. The boehmite can be CATAPAL® B, VERSAL™ 250, or PB 250 alumina. The molar ratio of molybdenum to vanadium in the catalyst used to prepare the aqueous mixture can be from 1:0.30 to 1:0.55. For example, the molar ratio of molybdenum to vanadium in the catalyst used to prepare the aqueous mixture can be from about 1:0.40 to about 1:0.49. The method can further include removing a substantial amount of the water (e.g., from about 50 wt. % to about 99 wt. % of the water) from the aqueous mixture to provide a precatalyst material. Removing a substantial amount of water from the aqueous mixture to provide a precatalyst material can include heating the aqueous mixture at a temperature from about 50° C. to about 100° C. Additionally, the method can include heating the precatalyst material to provide the catalyst material. Heating the precatalyst material to provide the catalyst material can include heating the precatalyst material at a temperature from about 350° C. to about 450° C.

In some embodiments, the catalyst material is treated with a gas that includes ethane, oxygen, ethylene, or a combination thereof at a temperature from about 300° C. to about 400° C. In some embodiments, the catalyst material is treated with a gas that includes ethane, oxygen, ethylene, or a combination thereof for a time of about 18 hours to about 72 hours. The gas treatment can convert at least a portion of the goethite to hematite.

In some embodiments, the catalyst material is characterized by having at least five XRD diffraction peaks (2θ degrees) chosen from 6.6±0.2, 7.8±0.2, 9.0±0.2, 10.8±0.2, 13.0±0.2, 14.0±0.2, 22.1±0.2, 26.3±0.2, 26.8±0.2, 27.3±0.2, 28.2±0.2, 29.3±0.2, 30.6±0.2, 31.4±0.2, 33.1±0.2, 35.5±0.2, 40.8±0.2, 45.1±0.2, 54.0±0.2, and 64.0±0.2 wherein the XRD is obtained using CuKα radiation.

Catalysts Including Molybdenum and Vanadium.

The catalyst materials disclosed herein can be prepared by a method that includes providing a catalyst that includes molybdenum, vanadium, and oxygen. The molar ratio of molybdenum to vanadium in the provided catalyst can be from 1:0.25 to 1:0.55. For example, the molar ratio of molybdenum to vanadium in the catalyst can be from 1:0.35 to 1:0.55. In some embodiments, the molar ratio of molybdenum to vanadium in the provided catalyst is from 1:0.40 to 1:0.49.

The molar ratio of molybdenum to vanadium can be determined by ICP-MS.

In some embodiments, the provided catalyst is a mixed metal oxide having the empirical formula:

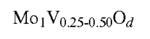

wherein d is a number to satisfy the valence of the oxide. For example, the provided catalyst can be a mixed metal oxide having the empirical formula:

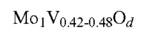

wherein d is a number to satisfy the valence of the oxide.

In some embodiments, providing the catalyst can include preparing an aqueous mixture including molybdenum and vanadium; hydrothermally reacting the aqueous mixture to form a precalcined catalyst; and calcining the precalcined catalyst to provide the catalyst. The pH of the hydrothermal reaction can be from 2.5 to 3.5. For example, the pH of the hydrothermal reaction can be about 2.85.

The aqueous mixture of molybdenum and vanadium can be prepared by combining an aqueous mixture that includes molybdenum and an aqueous mixture that includes vanadium. The aqueous mixture including molybdenum can prepared from at least $(NH_4)_6Mo_7O_{24}\cdot 4H_2O$ and a first water. The aqueous mixture including vanadium can be prepared from at least $VOSO_4\cdot XH_2O$ and a second water. In some embodiments, the molar the molar ratio of $(NH_4)_6Mo_7O_{24}\cdot 4H_2O$ to $VOSO_4\cdot XH_2O$ used to prepare the aqueous mixture including molybdenum and the aqueous mixture including vanadium is from 1:1.5 to 1:2. For example, the molar ratio of $(NH_4)_6Mo_7O_{24}\cdot 4H_2O$ to $VOSO_4\cdot XH_2O$ can be about 1:1.75.

In some embodiments, the concentration of molybdenum in the aqueous mixture of molybdenum and vanadium is less than $6.3\times10^{-1}$ mol/L. For example, the concentration of molybdenum in the aqueous mixture can be from $2.09\times10^{-1}$ mol/L to $3.13\times10^{-1}$ mol/L. In some embodiments, the concentration of vanadium in the aqueous mixture of molybdenum and vanadium is less than $15.60\times10^{-2}$ mol/L. For example, the concentration of vanadium in the aqueous mixture can be from $5.20\times10^{-2}$ mol/L to $7.80\times10^{-2}$ mol/L.

In some embodiments, providing the catalyst further includes contacting the aqueous mixture of molybdenum and vanadium with a templating agent. For example, a templating agent such as a surfactant, a catalyst seed, or a combination thereof can be added to the aqueous mixture of molybdenum and vanadium. In some embodiments, the templating agent is added to the aqueous mixture of molybdenum before it is combined with the aqueous mixture of vanadium to provide the aqueous mixture of molybdenum and vanadium. In some embodiments, the templating agent is added to the aqueous mixture of vanadium before it is combined with the aqueous mixture of molybdenum to provide the aqueous mixture of molybdenum and vanadium.

In some embodiments, the catalyst seed can be a catalyst seed including molybdenum and vanadium; a catalyst seed including molybdenum, vanadium, tellurium, and niobium, or a combination thereof. The catalyst seed including molybdenum and vanadium can be a previously synthesized catalyst including molybdenum and vanadium. For example, catalyst seed including molybdenum and vanadium can be a mixed metal oxide having the empirical formula:

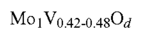

$$Mo_1V_{0.42\text{-}0.48}O_d$$

wherein d is a number to satisfy the valence of the oxide. The catalyst seed including molybdenum and vanadium can also be an orthorhombic, trigonal, tetragonal, or amorphous solid that includes molybdenum and vanadium. In some embodiments, the catalyst seed including molybdenum, vanadium, tellurium, and niobium is an orthorhombic, trigonal, tetragonal, or amorphous solid that includes molybdenum, vanadium, tellurium, and niobium.

In some embodiments, the weight ratio of the catalyst seed to the $(NH_4)_6Mo_7O_{24}\cdot 4H_2O$ used to prepare the aqueous mixture is about 0.5:100 to about 4.0:100.

In some embodiments, the templating agent includes a surfactant. For example, the templating agent can include sodium dodecyl sulfate (SDS). In some embodiments, the surfactant molar loading is from about 0.005 to about 0.2 or about 0.015 to 0.2. As used herein, the term "surfactant molar loading" refers to the moles of surfactant per moles of molybdenum and moles of vanadium in the aqueous mixture including molybdenum and vanadium.

In some embodiments, the first and the second water of the aqueous mixture including molybdenum—prepared from at least $(NH_4)_6Mo_7O_{24}\cdot 4H_2O$—and the aqueous mixture including vanadium—prepared from at least $VOSO_4\cdot XH_2O$—are selected independently from a distilled water, a deionized water, a demineralized water, a mineral water, or a combination thereof. In some embodiments, the first and second water include a distilled water.

In some embodiments, hydrothermally reacting the solution to form a precalcined catalyst includes heating the aqueous mixture of molybdenum and vanadium at a temperature of about 150° C. to about 300° C. For example, hydrothermally reacting the solution to form a precalcined catalyst can include heating the aqueous mixture of molybdenum and vanadium at a temperature of about 200° C. to about 250° C. In some embodiments, hydrothermally reacting the solution to form a precalcined catalyst includes heating the aqueous mixture of molybdenum and vanadium at a temperature of about 220° C. to about 230° C.

In some embodiments, hydrothermally reacting the solution to form a precalcined catalyst includes heating the aqueous mixture of molybdenum and vanadium at a temperature of about 150° C. to about 300° C., while maintaining a pressure above the saturated vapor pressure of the water at the corresponding temperature.

In some embodiments, hydrothermally reacting the solution to form a precalcined catalyst includes contacting the solution with a glass liner, a steel liner, or a Teflon liner. For example, hydrothermally reacting the aqueous mixture to form a precalcined catalyst can include contacting the aqueous mixture with a glass liner. In some embodiments, hydrothermally reacting the aqueous mixture to form a precalcined catalyst includes contacting the aqueous mixture with a Teflon liner. In some embodiments, hydrothermally reacting the aqueous mixture to form a precalcined catalyst includes contacting the aqueous mixture with a steel liner. In some embodiments, the steel liner is a HASTELLOY® steel liner, an INCONEL® steel liner, or a stainless liner.

In some embodiments, the method of preparing the catalyst further includes treating the precalcined catalyst in air at a temperature from about from 250° C. to 300° C. For example, the precalcined catalyst can be treated in air at a temperature of about 280° C. Treating the precalcined catalyst at an elevated temperature can serve to remove any residual volatile compounds in the precalcined catalyst such as surfactant, if used. In some embodiments, the method of preparing the catalyst further includes treating the precalcined catalyst in air at a temperature from about from 250° C. to 300° C. for about 0.5 hours to about 120 hours or for about 2 to about 76 hours.

In some embodiments, the precalcined catalyst is calcined at about 300° C. to about 500° C. to provide the catalyst. For example, the precalcined catalyst can be calcined at about 375° C. to about 425° C. In some embodiments, the precalcined catalyst is calcined at about 300° C. to about 500° C. for about 1 hour to about 24 hours. In some embodiments, precalcined catalyst is calcined at about 375° C. to about 425° C. for about 1 hour to about 4 hours.

In some embodiments, the precalcined catalyst is calcined in air, an inert atmosphere, or a combination thereof. In some embodiments, the precalcined catalyst is calcined in an inert atmosphere. For example, the precalcined catalyst can calcined in an inert atmosphere including $N_2$.

Also provided herein is a method for the oxidative dehydrogenation of ethane to ethylene in an oxidative dehydrogenation reactor with any of the oxidative dehydrogenation catalyst materials described herein.

Ethylene can subsequently be converted into a variety of products. For example, ethylene can be converted into many various compounds including low density polyethylene, high density polyethylene, ethylene dichloride, ethylene oxide, ethylbenzene, linear alcohols, vinyl acetate, alkanes, alpha olefins (e.g., 1-hexene and 1-octene), various hydrocarbon-based fuels, ethanol and the like. These compounds can then be further processed using methods well known to one of ordinary skill in the art to obtain other valuable chemicals and consumer products.

Non-limiting embodiments disclosed herein include:

Embodiment A: An oxidative dehydrogenation catalyst material that includes molybdenum, vanadium, oxygen, and iron, wherein the molar ratio of molybdenum to vanadium is from 1:0.25 to 1:0.50, the molar ratio of molybdenum to iron is from 1:0.25 to 1:5.5, and oxygen is present at least in an amount to satisfy the valency of any present metal oxides.

Embodiment A may have one or more of the following additional elements in any combination:

Element A1: Wherein the molar ratio of molybdenum to vanadium is from 1:0.30 to 1:0.45.

Element A2: Wherein the molar ratio of molybdenum to vanadium is from 1:0.30 to 1:0.35.

Element A3: Wherein the molar ratio of molybdenum to vanadium is from 1:0.35 to 1:0.45.

Element A4: Wherein the molar ratio of molybdenum to iron is from 1:3 to 1:5.5.

Element A5: Wherein the molar ratio of molybdenum to iron is from 1:4.25 to 1:4.75.

Element A6: Wherein the molar ratio of molybdenum to iron is from 1:4.45 to 1:4.55.

Element A7: Wherein the molar ratio of molybdenum to iron is from 1:0.1 to 1:1.

Element A8: Wherein the molar ratio of molybdenum to iron is from 1:0.25 to 1:0.75.

Element A9: Wherein the molar ratio of molybdenum to iron is from 1:0.4 to about 1:0.6.

Element A10: Wherein the molar ratio of molybdenum to iron is about 1:0.4.

Element A11: Wherein the molar ratio of molybdenum to iron is about 1:0.6.

Element A12: Wherein the molar ratio of molybdenum to iron is from 1:1.3 to 1:2.2.

Element A13: Wherein the molar ratio of molybdenum to iron is from 1:1.6 to 1:2.0.

Element A14: Wherein the molar ratio of molybdenum to iron is from 1:1.80 to 1:1.90.

Element A15: Wherein the catalyst material has a 35% conversion temperature from about 300° C. to about 400° C.

Element A16: Wherein the catalyst material has a 35% conversion temperature from about 300° C. to about 350° C.

Element A17: Wherein the catalyst material has a 35% conversion temperature from about 315° C. to about 335° C.

Element A18: Wherein the catalyst material has a selectivity to ethylene from about 65% to 99%.

Element A19: Wherein the catalyst material has a selectivity to ethylene from about 75% to 95%.

Element A20: Wherein at least a portion of the iron in the catalyst material is present as Fe(III).

Element A21: Wherein at least a portion of the iron in the catalyst material is present as amorphous iron.

Element A22: Wherein at least a portion of the iron in the catalyst material is present as an iron oxide, an iron oxide hydroxide, or a combination thereof.

Element A23: Wherein at least a portion of the iron in the catalyst material is present as an iron oxide, an iron oxide hydroxide, or a combination thereof; and wherein the iron oxide includes an iron oxide selected from hematite ($\alpha$-$Fe_2O_3$), maghemite ($\gamma$-$Fe_2O_3$), magnetite ($Fe_3O_4$), or a combination thereof.

Element A24: Wherein at least a portion of the iron in the catalyst material is present as a hematite.

Element A25: Wherein at least a portion of the iron in the catalyst material is present as an iron oxide, an iron oxide hydroxide, or a combination thereof; and wherein the iron oxide hydroxide includes an iron oxide hydroxide selected from a goethite, an akageneite, a lepidocrocite, or a combination thereof.

Element A26: Wherein at least a portion of the iron in the catalyst material is present as an iron oxide, an iron oxide hydroxide, or a combination thereof; and wherein the iron oxide hydroxide includes a goethite.

Element A27: Wherein at least a portion of the iron in the catalyst material is present as a goethite and at least a portion of the iron in the catalyst material is present a hematite.

Element A28: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material.

Element A29: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein the molar ratio of molybdenum to vanadium in the catalyst is from 1:0.25 to 1:0.5.

Element A30: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein the molar ratio of molybdenum to vanadium in the catalyst is from 1:0.3 to 1:0.49.

Element A31: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein the catalyst includes a mixed metal oxide having the empirical formula:

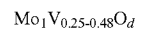

wherein d is a number to satisfy the valence of the oxide.

Element A32: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen.

Element A33: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the aqueous mixture of molybdenum and vanadium is prepared by combining an aqueous mixture including molybdenum and an aqueous mixture including vanadium and wherein the aqueous mixture including molybdenum is prepared from at least $(NH_4)_6Mo_7O_{24}\cdot 4H_2O$ and a first water, and the aqueous mixture including vanadium is prepared from at least $VOSO_4\cdot XH_2O$ and a second water.

Element A34: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the aqueous mixture of molybdenum and vanadium is prepared by combining an aqueous mixture including molybdenum and an aqueous mixture including vanadium and wherein the aqueous mixture including molybdenum is prepared from at least $(NH_4)_6Mo_7O_{24}\cdot 4H_2O$ and a first water, and the aqueous mixture including vanadium is prepared from at least $VOSO_4\cdot XH_2O$ and a second water; and wherein the molar ratio of $(NH_4)_6Mo_7O_{24}\cdot 4H_2O$ to $VOSO_4\cdot XH_2O$ is from 1:1.5 to 1:2.

Element A35: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the aqueous mixture of molybdenum and vanadium is prepared by combining an aqueous mixture including molybdenum and an aqueous mixture including vanadium and wherein the aqueous mixture including molybdenum is prepared from at least $(NH_4)_6Mo_7O_{24}\cdot 4H_2O$ and a first water, and the aqueous mixture including vanadium is prepared from at least $VOSO_4\cdot XH_2O$ and a second water; and wherein the molar ratio of $(NH_4)_6Mo_7O_{24}\cdot 4H_2O$ to $VOSO_4\cdot XH_2O$ is about 1:1.75.

Element A36: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the concentration of molybdenum in the aqueous mixture of molybdenum and vanadium is less than $6.3\times10^{-1}$ mol/L.

Element A37: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the concentration of molybdenum in the aqueous mixture of molybdenum and vanadium is from $2.09\times10^{-1}$ mol/L to $3.13\times10^{-1}$ mol/L.

Element A38: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the concentration of vanadium in the aqueous mixture of molybdenum and vanadium is less than $15.60\times10^{-2}$ mol/L.

Element A39: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the concentration of vanadium in the aqueous mixture of molybdenum and vanadium is from $5.20\times10^{-2}$ mol/L to $7.80\times10^{-2}$ mol/L.

Element A40: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein providing the catalyst further includes contacting the aqueous mixture of molybdenum and vanadium with a templating agent.

Element A41: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein providing the catalyst further includes contacting the aqueous mixture of molybdenum and vanadium with a templating agent; and wherein the templating agent includes a surfactant, a catalyst seed, or a combination thereof.

Element A42: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein providing the catalyst further includes contacting the aqueous mixture of molybdenum and vanadium with a templating agent; and wherein the templating agent includes a catalyst seed; and wherein the catalyst seed includes a catalyst seed selected from a catalyst seed including molybdenum and vanadium, a catalyst seed including molybdenum, vanadium, tellurium, and niobium, or a combination thereof.

Element A43: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein providing the catalyst further includes contacting the aqueous mixture of molybdenum and vanadium with a templating agent; and wherein the templating agent includes a catalyst seed; and wherein the weight ratio of the catalyst seed to the $(NH_4)_6Mo_7O_{24}\cdot4H_2O$ used to prepare the aqueous mixture is about 0.5:100 to about 4.0:100.

Element A44: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein providing the catalyst further includes contacting the aqueous mixture of molybdenum and vanadium with a templating agent; and wherein the templating agent includes a surfactant.

Element A45: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein providing the catalyst further includes contacting the aqueous mixture of molybdenum and vanadium with a templating agent; and wherein the templating agent includes a surfactant; and wherein the surfactant molar loading is from about 0.005 to about 0.2.

Element A46: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the aqueous mixture of molybdenum and vanadium is prepared by combining an aqueous mixture including molybdenum and an aqueous mixture including vanadium and wherein the aqueous mixture including molybdenum is prepared from at least $(NH_4)_6Mo_7O_{24}\cdot4H_2O$ and a first water, and the aqueous mixture including vanadium is prepared from at least $VOSO_4\cdot XH_2O$ and a second water; and wherein the first and the second water are selected from a distilled water, a deionized water, a demineralized water, a mineral water, or a combination thereof.

Element A47: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the aqueous mixture of molybdenum and vanadium is prepared by combining an aqueous mixture including molybdenum and an aqueous mixture including vanadium and wherein the aqueous mixture including molybdenum is prepared from at least $(NH_4)_6Mo_7O_{24}\cdot 4H_2O$ and a first water, and the aqueous mixture including vanadium is prepared from at least $VOSO_4\cdot XH_2O$ and a second water; and wherein the first and second water include a distilled water.

Element A48: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein hydrothermally reacting the aqueous mixture to form a precalcined catalyst includes heating the aqueous mixture of molybdenum and vanadium at a temperature of about 150° C. to about 300° C.

Element A49: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein hydrothermally reacting the aqueous mixture to form a precalcined catalyst includes heating the aqueous mixture of molybdenum and vanadium at a temperature of about 200° C. to about 250° C.

Element A50: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein hydrothermally reacting the aqueous mixture to form a precalcined catalyst includes heating the aqueous mixture of molybdenum and vanadium at a temperature of about 220° C. to about 230° C.

Element A51: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein hydrothermally reacting the aqueous mixture to form a precalcined catalyst includes contacting the aqueous mixture with a glass liner, a steel liner, or a Teflon liner.

Element A52: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein hydrothermally reacting the aqueous mixture to form a precalcined catalyst includes contacting the aqueous mixture with a glass liner.

Element A53: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein hydrothermally reacting the aqueous mixture to form a precalcined catalyst includes contacting the aqueous mixture with a Teflon liner.

Element A54: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein providing the catalyst further includes treating the precalcined catalyst in air from 250° C. to 300° C.

Element A55: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein providing the catalyst further includes treating the precalcined catalyst in air at about 280° C.

Element A56: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the precalcined catalyst is calcined at about 300° C. to about 500° C.

Element A57: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the precalcined catalyst is calcined at about 375° C. to about 425° C.

Element A58: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the precalcined catalyst is calcined at about 300° C. to about 500° C. for about 1 hour to about 24 hours.

Element A59: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the precalcined catalyst is calcined at about 375° C. to about 425° C. for about 1 hour to about 4 hours.

Element A60: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the precalcined catalyst is calcined in air, an inert atmosphere, or a combination thereof.

Element A61: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the precalcined catalyst is calcined in an inert atmosphere.

Element A62: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the inert atmosphere includes nitrogen.

Element A63: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein the iron compound in the mixture including the catalyst, the iron compound, and the water includes an Fe(III) compound.

Element A64: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein the iron compound in the mixture including the catalyst, the iron compound, and the water includes an iron compound selected from an iron oxide, an iron oxide hydroxide, or a combination thereof.

Element A65: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein the iron compound in the mixture includes an iron oxide selected from hematite (($\alpha$-$Fe_2O_3$), maghemite ($\gamma$-$Fe_2O_3$), magnetite ($Fe_3O_4$), or a combination thereof.

Element A66: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein the iron compound in the mixture includes hematite.

Element A67: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein the iron compound in the mixture includes an iron oxide hydroxide selected from a goethite, an akageneite, a lepidocrocite, or a combination thereof.

Element A68: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein the iron compound in the mixture includes a goethite.

Element A69: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein removing a substantial amount of water from the mixture including the catalyst, the iron compound, and the water to provide a precatalyst material includes heating the aqueous mixture at a temperature from about 50° C. to about 100° C.

Element A70: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein removing a substantial amount of water from the aqueous mixture including the catalyst, the iron compound, and the water to provide a precatalyst material includes heating the aqueous mixture at a temperature of about 80° C.

Element A71: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein removing a substantial amount of water from the aqueous mixture including the catalyst, the iron compound, and the water to provide a precatalyst material includes removing from about 50 wt. % to about 99 wt. % of the added water.

Element A72: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein heating the precatalyst material to provide the catalyst material includes heating the precatalyst material at a temperature from about 300° C. to about 500° C.

Element A73: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein heating the precatalyst material to provide the catalyst material includes heating the precatalyst material at a temperature from about 350° C. to about 450° C.

Element A74: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein heating the precatalyst material to provide the catalyst material includes heating the precatalyst material in the presence of air, an oxidizing atmosphere, an inert atmosphere, or a combination thereof.

Element A75: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein heating the precatalyst material to provide the catalyst material includes heating the precatalyst material the presence of air.

Element A76: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein the catalyst material is treated with a gas including ethane.

Element A77: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein the catalyst material is treated with a gas including ethane; and wherein the gas further includes oxygen.

Element A78: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein the catalyst material is treated with a gas including ethane; and wherein the gas further includes ethylene.

Element A89: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein the catalyst material is treated with a gas including ethane; and wherein the catalyst material is treated with the gas including ethane at a temperature from about 100° C. to about 500° C.

Element A80: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein the catalyst material is treated with a gas including ethane.

Element A81: Wherein the catalyst material is prepared by a method that includes providing a catalyst including molybdenum, vanadium, and oxygen, preparing an aqueous mixture including the catalyst, an iron compound, and a water, removing a substantial amount of the water from the mixture to provide a precatalyst material, and heating the precatalyst material to provide the catalyst material; and wherein the catalyst material is treated with a gas including ethane; and wherein the catalyst material is treated with the gas including ethane for about 18 hours to about 72 hours.

By way of non-limiting example, exemplary element combinations applicable to Embodiment A include: A1 and A4; A1 and A7; A1 and A12; A1, A4 and A24; A1, A7, and A24; A1, A12, and A24; A1, A4, and A27; A1, A7, and A27; A1, A12, and A27; A1, A4, and A28; A1, A7, and A28; A1, A12, and A28; A1, A4, and A66; A1, A7, and A66; and A1, A12, and A66.

Embodiment B: An oxidative dehydrogenation catalyst material that includes molybdenum, vanadium, oxygen, and aluminum, wherein the molar ratio of molybdenum to vanadium is from 1:0.1 to 1:0.50, the molar ratio of molybdenum to aluminum is from 1:1.5 to 1:6.5, and oxygen is present at least in an amount to satisfy the valency of any present metal oxides.

Embodiment B may have one or more of the following additional elements in any combination:

Element B1: Wherein the molar ratio of molybdenum to vanadium is from 1:0.30 to 1:0.45.

Element B2: Wherein the molar ratio of molybdenum to vanadium is from 1:0.30 to 1:0.35.

Element B3: Wherein the molar ratio of molybdenum to vanadium is from 1:0.35 to 1:0.45.

Element B4: Wherein the molar ratio of molybdenum to aluminum is from 1:3.0 to 1:6.5.

Element B5: Wherein the molar ratio of molybdenum to aluminum is from 1:3.25 to 1:5.5.5.

Element B6: Wherein the molar ratio of molybdenum to aluminum is from 1:3.5 to 1:4.1.

Element B7: Wherein the molar ratio of molybdenum to aluminum is from 1:4.95 to 1:5.05.

Element B8: Wherein the molar ratio of molybdenum to aluminum is from 1:4.55 to 1:4.65.

Element B9: Wherein the molar ratio of molybdenum to aluminum is from 1:1.5 to 1:3.5.

Element B10: Wherein the molar ratio of molybdenum to aluminum is from 1:2.0 to 1:2.2.

Element B11: Wherein the molar ratio of molybdenum to aluminum is from 1:2.9 to 1:3.1.

Element B12: Wherein the catalyst material has a 35% conversion temperature from about 300° C. to about 400° C.

Element B13: Wherein the catalyst material has a 35% conversion temperature from about 300° C. to about 350° C.

Element B14: Wherein the catalyst material has a 35% conversion temperature from about 315° C. to about 335° C.

Element B15: Wherein the catalyst material has a selectivity to ethylene from about 65% to 99%.

Element B16: Wherein the catalyst material has a selectivity to ethylene from about 75% to 95%.

Element B17: Wherein at least a portion of the aluminum in the catalyst material is present as an aluminum oxide.

Element B18: Wherein at least a portion of the aluminum in the catalyst material is present as an aluminum oxide hydroxide.

Element B19: Wherein at least a portion of the aluminum in the catalyst material is present as a gibbsite, a bayerite, a boehmite, or a combination thereof.

Element B20: Wherein at least a portion of the aluminum in the catalyst material is present as a boehmite.

Element B21: Wherein at least a portion of the aluminum in the catalyst material is present as gamma alumina.

Element B22: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material.

Element B23: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein the molar ratio of molybdenum to vanadium in the catalyst is from 1:0.25 to 1:0.5.

Element B24: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein the molar ratio of molybdenum to vanadium in the catalyst is from 1:0.3 to 1:0.49.

Element B25: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein the catalyst includes a mixed metal oxide having the empirical formula:

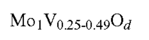

wherein d is a number to satisfy the valence of the oxide.

Element B26: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen.

Element B27: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the aqueous mixture of molybdenum and vanadium is prepared by combining an aqueous mixture including molybdenum and an aqueous mixture including vanadium and wherein the aqueous mixture including molybdenum is prepared from at least $(NH_4)_6Mo_7O_{24}\cdot 4H_2O$ and a first water and wherein the aqueous mixture including vanadium is prepared from at least $VOSO_4\cdot XH_2O$ and a second water.

Element B28: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the aqueous mixture of molybdenum and vanadium is prepared by combining an aqueous mixture including molybdenum and an aqueous mixture including vanadium and wherein the aqueous mixture including molybdenum is prepared from at least $(NH_4)_6Mo_7O_{24}\cdot 4H_2O$ and a first water and wherein the aqueous mixture including vanadium is prepared from at least $VOSO_4\cdot XH_2O$ and a second water; and wherein the molar ratio of $(NH_4)_6Mo_7O_{24}\cdot 4H_2O$ to $VOSO_4\cdot XH_2O$ is from 1:1.5 to 1:2.

Element B29: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the aqueous mixture of molybdenum and vanadium is prepared by combining an aqueous mixture including molybdenum and an aqueous mixture including vanadium and wherein the aqueous mixture including molybdenum is prepared from at least $(NH_4)_6Mo_7O_{24}\cdot 4H_2O$ and a first water and wherein the aqueous mixture including vanadium is prepared from at least $VOSO_4\cdot XH_2O$ and a second water; and wherein the molar ratio of $(NH_4)_6Mo_7O_{24}\cdot 4H_2O$ to $VOSO_4\cdot XH_2O$ is about 1:1.75.

Element B30: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the aqueous mixture of molybdenum and vanadium is prepared by combining an aqueous mixture including molybdenum and an aqueous mixture including vanadium and wherein the aqueous mixture including molybdenum is prepared from at least $(NH_4)_6Mo_7O_{24}\cdot 4H_2O$ and a first water and wherein the aqueous mixture including vanadium is prepared from at least $VOSO_4\cdot XH_2O$ and a second water; and wherein the concentration of molybdenum in the aqueous mixture of molybdenum and vanadium is less than $6.3\times10^{-1}$ mol/L.

Element B31: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the aqueous mixture of molybdenum and vanadium is prepared by combining an aqueous mixture including molybdenum and an aqueous mixture including vanadium and wherein the aqueous mixture including molybdenum is prepared from at least $(NH_4)_6Mo_7O_{24}\cdot 4H_2O$ and a first water and wherein the aqueous mixture including vanadium is prepared from at least $VOSO_4\cdot XH_2O$ and a second water; and wherein the concentration of molybdenum in the aqueous mixture of molybdenum and vanadium is from $2.09\times10^{-1}$ mol/L to $3.13\times10^{-1}$ mol/L.

Element B32: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the aqueous mixture of molybdenum and vanadium is prepared by combining an aqueous mixture including molybdenum and an aqueous mixture including vanadium and wherein the aqueous mixture including molybdenum is prepared from at least $(NH_4)_6Mo_7O_{24}\cdot4H_2O$ and a first water and wherein the aqueous mixture including vanadium is prepared from at least $VOSO_4\cdot XH_2O$ and a second water; and wherein the concentration of vanadium in the aqueous mixture of molybdenum and vanadium is less than $15.60\times10^{-2}$ mol/L.

Element B33: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the aqueous mixture of molybdenum and vanadium is prepared by combining an aqueous mixture including molybdenum and an aqueous mixture including vanadium and wherein the aqueous mixture including molybdenum is prepared from at least $(NH_4)_6Mo_7O_{24}\cdot4H_2O$ and a first water and wherein the aqueous mixture including vanadium is prepared from at least $VOSO_4\cdot XH_2O$ and a second water; and wherein the concentration of vanadium in the aqueous mixture of molybdenum and vanadium is from $5.20\times10^{-2}$ mol/L to $7.80\times10^{-2}$ mol/L.

Element B34: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein providing the catalyst further includes contacting the aqueous mixture of molybdenum and vanadium with a templating agent.

Element B35: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein providing the catalyst further includes contacting the aqueous mixture of molybdenum and vanadium with a templating agent; and wherein the templating agent includes a surfactant, a catalyst seed, or a combination thereof.

Element B36: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein providing the catalyst further includes contacting the aqueous mixture of molybdenum and vanadium with a templating agent that includes a catalyst seed; and wherein the catalyst seed includes a catalyst seed selected from a catalyst seed including molybdenum and vanadium; a catalyst seed including molybdenum, vanadium, tellurium, and niobium, or a combination thereof.

Element B37: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein providing the catalyst further includes contacting the aqueous mixture of molybdenum and vanadium with a templating agent that includes a catalyst seed; and wherein the catalyst seed includes a catalyst seed selected from a catalyst seed including molybdenum and vanadium; a catalyst seed including molybdenum, vanadium, tellurium, and niobium, or a combination thereof; and wherein the weight ratio of the catalyst seed to the $(NH_4)_6Mo_7O_{24}\cdot4H_2O$ used to prepare the aqueous mixture is about 0.5:100 to about 4.0:100.

Element B38: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein providing the catalyst further includes contacting the aqueous mixture of molybdenum and vanadium with a templating agent that include a surfactant.

Element B39: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein providing the catalyst further includes contacting the aqueous mixture of molybdenum and vanadium with a templating agent that include a surfactant; and wherein the surfactant molar loading is from about 0.005 to about 0.2.

Element B40: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the aqueous mixture of molybdenum and vanadium is prepared by combining an aqueous mixture including molybdenum and an aqueous mixture including vanadium and wherein the aqueous mixture including molybdenum is prepared from at least $(NH_4)_6Mo_7O_{24}\cdot4H_2O$ and a first water, and the aqueous mixture including vanadium is prepared from at least $VOSO_4\cdot XH_2O$ and a second water; and wherein the first and the second water are selected from a distilled water, a deionized water, a demineralized water, a mineral water, or a combination thereof.

Element B41: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the aqueous mixture of molybdenum and vanadium is prepared by combining an aqueous mixture including molybdenum and an aqueous mixture including vanadium and wherein the aqueous mixture including molybdenum is prepared from at least $(NH_4)_6Mo_7O_{24}\cdot4H_2O$ and a first water, and the aqueous mixture including vanadium is prepared from at least $VOSO_4\cdot XH_2O$ and a second water; and wherein the first and second water include a distilled water.

Element B42: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein hydrothermally reacting the aqueous mixture to form a precalcined catalyst includes heating the aqueous mixture of molybdenum and vanadium at a temperature of about 150° C. to about 300° C.

Element B43: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein hydrothermally reacting the aqueous mixture to form a precalcined catalyst includes heating the aqueous mixture of molybdenum and vanadium at a temperature of about 200° C. to about 250° C.

Element B44: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein hydrothermally reacting the aqueous mixture to form a precalcined catalyst includes heating the aqueous mixture of molybdenum and vanadium at a temperature of about 220° C. to about 230° C.

Element B45: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein hydrothermally reacting the aqueous mixture to form a precalcined catalyst includes contacting the aqueous mixture with a glass liner, a steel liner, or a Teflon liner.

Element B46: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein hydrothermally reacting the aqueous mixture to form a precalcined catalyst includes contacting the aqueous mixture with a glass liner.

Element B47: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein hydrothermally reacting the aqueous mixture to form a precalcined catalyst includes contacting the aqueous mixture with a Teflon liner.

Element B48: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein providing the catalyst further includes treating the precalcined catalyst in air from 250° C. to 300° C.

Element B49: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein providing the catalyst further includes treating the precalcined catalyst in air at about 280° C.

Element B50: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the precalcined catalyst is calcined at about 300° C. to about 500° C.

Element B51: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the precalcined catalyst is calcined at about 375° C. to about 425° C.

Element B52: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the precalcined catalyst is calcined at about 300° C. to about 500° C. for about 1 hour to about 24 hours.

Element B53: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the precalcined catalyst is calcined at about 375° C. to about 425° C. for about 1 hour to about 4 hours.

Element B54: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the precalcined catalyst is calcined in air, an inert atmosphere, or a combination thereof.

Element B55: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the precalcined catalyst is calcined in an inert atmosphere.

Element B56: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the inert atmosphere includes nitrogen.

Element B57: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein the aluminum compound in the aqueous mixture including the catalyst, the aluminum compound, and the water includes an aluminum oxide.

Element B58: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein the aluminum compound in the aqueous mixture including the catalyst, the aluminum compound, and the water includes an aluminum oxide hydroxide.

Element B59: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein the aluminum compound in the aqueous mixture including the catalyst, the aluminum compound, and the water includes an aluminum oxide hydroxide selected from a gibbsite, a bayerite, a boehmite, or a combination thereof.

Element B60: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein the aluminum compound in the aqueous mixture including the catalyst, the aluminum compound, and the water includes a boehmite.

Element B61: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein removing a substantial amount of water from the mixture including the catalyst, the aluminum compound, and the water to provide a precatalyst material includes heating the aqueous mixture at a temperature from about 50° C. to about 100° C.

Element B62: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein removing a substantial amount of water from the mixture including the catalyst, the aluminum compound, and the water to provide a precatalyst material includes heating the aqueous mixture at a temperature of about 80° C.

Element B63: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein removing a substantial amount of water from the aqueous mixture including the catalyst, the aluminum compound, and the water to provide a precatalyst material includes removing from about 50 wt. % to about 99 wt. % of the water.

Element B64: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein heating the precatalyst material to provide the catalyst material includes heating the precatalyst material at a temperature from about 300° C. to about 500° C.

Element B65: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein heating the precatalyst material to provide the catalyst material includes heating the precatalyst material at a temperature from about 350° C. to about 450° C.

Element B66: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein heating the precatalyst material to provide the catalyst material includes heating the precatalyst material in air.

Element B67: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein the catalyst material is treated with a gas including ethane.

Element B68: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein the catalyst material is treated with a gas including ethane; and wherein the gas further includes oxygen.

Element B69: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein the catalyst material is further treated with a gas including ethane; and wherein the gas further includes ethylene.

Element B70: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein the catalyst material is further treated with a gas including ethane; and wherein the catalyst material is further treated with the gas including ethane at a temperature from about 100° C. to about 500° C.

Element B71: Wherein the catalyst material is prepared by a method that includes providing a catalyst including molybdenum, vanadium, and oxygen, preparing an aqueous mixture including the catalyst, an aluminum compound, and a water, removing a substantial amount of the water from the mixture to provide a precatalyst material, and heating the precatalyst material to provide the catalyst material; and wherein the catalyst material is treated with a gas including ethane; and wherein the catalyst material is treated with the gas including ethane for about 18 hours to about 72 hours.

By way of non-limiting example, exemplary element combinations applicable to Embodiment B include: B1 and B4; B1 and B9; B1, B4, and B20; B1, B9, and B20; B1, B4, and B22; B1, B9, and B22; B1, B4, and B60; and B1, B9, and B60.

Embodiment C: An oxidative dehydrogenation catalyst material that includes molybdenum, vanadium, oxygen, aluminum, and iron, wherein the molar ratio of molybdenum to vanadium is from 1:0.1 to 1:0.5, the molar ratio of molybdenum to aluminum is from 1:1.5 to 1:6.0, the molar ratio of molybdenum to iron is from 1:0.25 to 5:5, and oxygen is present at least in an amount to satisfy the valency of any present metal oxides.

Embodiment C may have one or more of the following additional elements in any combination:

Element C1: Wherein the molar ratio of molybdenum to vanadium is from 1:0.30 to 1:0.45.

Element C2: Wherein the molar ratio of molybdenum to vanadium is from 1:0.30 to 1:0.35.

Element C3: Wherein the molar ratio of molybdenum to vanadium is from 1:0.35 to 1:0.45.

Element C4: Wherein the molar ratio of molybdenum to iron is from 1:0.1 to 1:1, and the molar ratio of molybdenum to aluminum is from 1:3.5 to 1:5.5.

Element C5: Wherein the molar ratio of molybdenum to iron is from 1:0.25 to 1:0.75, and the molar ratio of molybdenum to aluminum is from 1:3.75 to 1:5.25.

Element C6: Wherein the molar ratio of molybdenum to iron is from 1:0.35 to 1:0.65, and the molar ratio of molybdenum to aluminum is from 1:3.75 to 1:5.25.

Element C7: Wherein the molar ratio of molybdenum to iron is from about 1:0.35 to about 1:0.45, and the molar ratio of molybdenum to aluminum is from 1:3.9 to 1:4.0.

Element C8: Wherein the molar ratio of molybdenum to iron is about 1:0.55 to about 0:65, and the molar ratio of molybdenum to aluminum is from 1:4.95 to 1:5.05.

Element C9: Wherein the molar ratio of molybdenum to iron is from 1:1.3 to 1:2.2, and the molar ratio of molybdenum to aluminum is from 1:2.0 to 1:4.0.

Element C10: Wherein the molar ratio of molybdenum to iron is from 1:1.6 to 1:2.0, and the molar ratio of molybdenum to aluminum is from 1:2.5 to 1:3.5.

Element C11: Wherein the molar ratio of molybdenum to iron is from about 1:1.80 to about 1:1.90, and the molar ratio of molybdenum to aluminum is from 1:2.9 to 1:3.1.

Element C12: Wherein the catalyst material has a 35% conversion temperature from about 300° C. to about 400° C.

Element C13: Wherein the catalyst material has a 35% conversion temperature from about 300° C. to about 350° C.

Element C14: Wherein the catalyst material has a 35% conversion temperature from about 315° C. to about 335° C.

Element C15: Wherein the catalyst material has a selectivity to ethylene from about 65% to 99%.

Element C16: Wherein the catalyst material has a selectivity to ethylene from about 75% to 95%.

Element C17: Wherein at least a portion of the iron in the catalyst material is present as Fe(III).

Element C18: Wherein at least a portion of the iron in the catalyst material is present as amorphous iron.

Element C19: Wherein at least a portion of the iron in the catalyst material is present as an iron oxide, an iron oxide hydroxide, or a combination thereof.

Element C20: Wherein at least a portion of the iron in the catalyst material is present as hematite ((t-$Fe_2O_3$), maghemite (γ-$Fe_2O_3$), magnetite ($Fe_3O_4$), or a combination thereof.

Element C21: Wherein at least a portion of the iron in the catalyst material is present as a hematite.

Element C22: Wherein at least a portion of the iron in the catalyst material is present as an iron oxide hydroxide selected from a goethite, an akageneite, a lepidocrocite, or a combination thereof.

Element C23: Wherein at least a portion of the iron in the catalyst material is present as a goethite.

Element C24: Wherein at least a portion of the iron in the catalyst material is present as a goethite and at least a portion of the iron in the catalyst material is present a hematite.

Element C25: Wherein at least a portion of the aluminum in the catalyst material is present as an aluminum oxide.

Element C26: Wherein at least a portion of the aluminum in the catalyst material is present as an aluminum oxide hydroxide.

Element C27: Wherein at least a portion of the aluminum in the catalyst material is present as a gibbsite, a bayerite, a boehmite, or a combination thereof.

Element C28: Wherein at least a portion of the aluminum in the catalyst material is present as a boehmite.

Element C29: Wherein at least a portion of the aluminum in the catalyst material is present as a gamma alumina.

Element C30: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material.

Element C31: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein the molar ratio of molybdenum to vanadium in the catalyst is from 1:0.25 to 1:0.5.

Element C32: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein the molar ratio of molybdenum to vanadium in the catalyst is from 1:0.3 to 1:0.49.

Element C33: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein the catalyst includes a mixed metal oxide having the empirical formula:

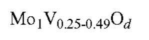

$$Mo_1V_{0.25-0.49}O_d$$

wherein d is a number to satisfy the valence of the oxide.

Element C34: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen.

Element C35: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the aqueous mixture of molybdenum and vanadium is prepared by combining an aqueous mixture including molybdenum and an aqueous mixture including vanadium and wherein the aqueous mixture including molybdenum is prepared from at least $(NH_4)_6Mo_7O_{24}\cdot4H_2O$ and a first water and wherein the aqueous mixture including vanadium is prepared from at least $VOSO_4\cdot XH_2O$ and a second water.

Element C36: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the aqueous mixture of molybdenum and vanadium is prepared by combining an aqueous mixture including molybdenum and an aqueous mixture including vanadium and wherein the aqueous mixture including molybdenum is prepared from at least $(NH_4)_6Mo_7O_{24}\cdot4H_2O$ and a first water and wherein the aqueous mixture including vanadium is prepared from at least $VOSO_4\cdot XH_2O$ and a second water; and wherein the molar ratio of $(NH_4)_6Mo_7O_{24}\cdot4H_2O$ to $VOSO_4\cdot XH_2O$ is from 1:1.5 to 1:2.

Element C37: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the aqueous mixture of molybdenum and vanadium is prepared by combining an aqueous mixture including molybdenum and an aqueous mixture including vanadium and wherein the aqueous mixture including molybdenum is prepared from at least $(NH_4)_6Mo_7O_{24}\cdot4H_2O$ and a first water and wherein the aqueous mixture including vanadium is prepared from at least $VOSO_4\cdot XH_2O$ and a second water; and wherein the molar ratio of $(NH_4)_6Mo_7O_{24}\cdot4H_2O$ to $VOSO_4\cdot XH_2O$ is about 1:1.75.

Element C38: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the aqueous mixture of molybdenum and vanadium is prepared by combining an aqueous mixture including molybdenum and an aqueous mixture including vanadium and wherein the aqueous mixture including molybdenum is prepared from at least $(NH_4)_6Mo_7O_{24}\cdot 4H_2O$ and a first water and wherein the aqueous mixture including vanadium is prepared from at least $VOSO_4\cdot XH_2O$ and a second water; and wherein the concentration of molybdenum in the aqueous mixture of molybdenum and vanadium is less than $6.3\times10^{-1}$ mol/L.

Element C39: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the aqueous mixture of molybdenum and vanadium is prepared by combining an aqueous mixture including molybdenum and an aqueous mixture including vanadium and wherein the aqueous mixture including molybdenum is prepared from at least $(NH_4)_6Mo_7O_{24}\cdot 4H_2O$ and a first water and wherein the aqueous mixture including vanadium is prepared from at least $VOSO_4\cdot XH_2O$ and a second water; and wherein the concentration of molybdenum in the aqueous mixture of molybdenum and vanadium is from $2.09\times10^{-1}$ mol/L to $3.13\times10^{-1}$ mol/L.

Element C40: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the aqueous mixture of molybdenum and vanadium is prepared by combining an aqueous mixture including molybdenum and an aqueous mixture including vanadium and wherein the aqueous mixture including molybdenum is prepared from at least $(NH_4)_6Mo_7O_{24}\cdot 4H_2O$ and a first water and wherein the aqueous mixture including vanadium is prepared from at least $VOSO_4\cdot XH_2O$ and a second water; and wherein the concentration of vanadium in the aqueous mixture of molybdenum and vanadium is less than $15.60\times10^{-2}$ mol/L.

Element C41: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the aqueous mixture of molybdenum and vanadium is prepared by combining an aqueous mixture including molybdenum and an aqueous mixture including vanadium and wherein the aqueous mixture including molybdenum is prepared from at least $(NH_4)_6Mo_7O_{24}\cdot 4H_2O$ and a first water and wherein the aqueous mixture including vanadium is prepared from at least $VOSO_4\cdot XH_2O$ and a second water; and wherein the concentration of vanadium in the aqueous mixture of molybdenum and vanadium is from $5.20\times10^{-2}$ mol/L to $7.80\times10^{-2}$ mol/L.

Element C42: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein providing the catalyst further includes contacting the aqueous mixture of molybdenum and vanadium with a templating agent.

Element C43: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein providing the catalyst further includes contacting the aqueous mixture of molybdenum and vanadium with a templating agent; and wherein the templating agent includes a surfactant, a catalyst seed, or a combination thereof.

Element C44: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein providing the catalyst further includes contacting the aqueous mixture of molybdenum and vanadium with a templating agent that includes a catalyst seed; and wherein the catalyst seed includes a catalyst seed selected from a catalyst seed including molybdenum and vanadium; a catalyst seed including molybdenum, vanadium, tellurium, and niobium, or a combination thereof.

Element C45: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein providing the catalyst further includes contacting the aqueous mixture of molybdenum and vanadium with a templating agent that includes a catalyst seed; and wherein the catalyst seed includes a catalyst seed selected from a catalyst seed including molybdenum and vanadium; a catalyst seed including molybdenum, vanadium, tellurium, and niobium, or a combination thereof; and wherein the weight ratio of the catalyst seed to the $(NH_4)_6Mo_7O_{24}\cdot 4H_2O$ used to prepare the aqueous mixture is about 0.5:100 to about 4.0:100.

Element C46: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein providing the catalyst further includes contacting the aqueous mixture of molybdenum and vanadium with a templating agent that include a surfactant.

Element C47: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein providing the catalyst further includes contacting the aqueous mixture of molybdenum and vanadium with a templating agent that include a surfactant; and wherein the surfactant molar loading is from about 0.005 to about 0.2.

Element C48: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the aqueous mixture of molybdenum and vanadium is prepared by combining an aqueous mixture including molybdenum and an aqueous mixture including vanadium and wherein the aqueous mixture including molybdenum is prepared from at least $(NH_4)_6Mo_7O_{24}\cdot 4H_2O$ and a first water, and the aqueous mixture including vanadium is prepared from at least $VOSO_4\cdot XH_2O$ and a second water; and wherein the first and the second water are selected from a distilled water, a deionized water, a demineralized water, a mineral water, or a combination thereof.

Element C49: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the aqueous mixture of molybdenum and vanadium is prepared by combining an aqueous mixture including molybdenum and an aqueous mixture including vanadium and wherein the aqueous mixture including molybdenum is prepared from at least $(NH_4)_6Mo_7O_{24}\cdot 4H_2O$ and a first water, and the aqueous mixture including vanadium is prepared from at least $VOSO_4\cdot XH_2O$ and a second water; and wherein the first and second water include a distilled water.

Element C50: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein hydrothermally reacting the aqueous mixture to form a precalcined catalyst includes heating the aqueous mixture of molybdenum and vanadium at a temperature of about 150° C. to about 300° C.

Element C51: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein hydrothermally reacting the aqueous mixture to form a precalcined catalyst includes heating the aqueous mixture of molybdenum and vanadium at a temperature of about 200° C. to about 250° C.

Element C52: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein hydrothermally reacting the aqueous mixture to form a precalcined catalyst includes heating the aqueous mixture of molybdenum and vanadium at a temperature of about 220° C. to about 230° C.

Element C53: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein hydrothermally reacting the aqueous mixture to form a precalcined catalyst includes contacting the aqueous mixture with a glass liner, a steel liner, or a Teflon liner.

Element C54: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein hydrothermally reacting the aqueous mixture to form a precalcined catalyst includes contacting the aqueous mixture with a glass liner.

Element C55: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein hydrothermally reacting the aqueous mixture to form a precalcined catalyst includes contacting the aqueous mixture with a Teflon liner.

Element C56: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein providing the catalyst further includes treating the precalcined catalyst in air from 250° C. to 300° C.

Element C57: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein providing the catalyst further includes treating the precalcined catalyst in air at about 280° C.

Element C58: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the precalcined catalyst is calcined at about 300° C. to about 500° C.

Element C59: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the precalcined catalyst is calcined at about 375° C. to about 425° C.

Element C60: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the precalcined catalyst is calcined at about 300° C. to about 500° C. for about 1 hour to about 24 hours.

Element C61: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the precalcined catalyst is calcined at about 375° C. to about 425° C. for about 1 hour to about 4 hours.

Element C62: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the precalcined catalyst is calcined in air, an inert atmosphere, or a combination thereof.

Element C63: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the precalcined catalyst is calcined in an inert atmosphere.

Element C64: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein providing the catalyst including molybdenum, vanadium, and oxygen includes preparing an aqueous mixture of molybdenum and vanadium, hydrothermally reacting the aqueous mixture to form a precalcined catalyst, and calcining the precalcined catalyst to provide the catalyst including molybdenum, vanadium, and oxygen; and wherein the inert atmosphere includes nitrogen.

Element C65: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein the iron compound in the aqueous mixture including the catalyst, the iron compound, the alumina compound, and the water includes an Fe(III) compound.

Element C66: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein the iron compound in the aqueous mixture including the catalyst, the iron compound, the alumina compound, and the water includes an iron compound selected from an iron oxide, an iron oxide hydroxide, or a combination thereof.

Element C67: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein the iron compound in the aqueous mixture including the catalyst, the iron compound, the alumina compound, and the water includes an iron oxide selected from α hematite ($\alpha$-$Fe_2O_3$), maghemite ($\gamma$-$Fe_2O_3$), magnetite ($Fe_3O_4$), or a combination thereof.

Element C68: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein the iron compound in the aqueous mixture including the catalyst, the iron compound, the alumina compound, and the water includes a hematite.

Element C69: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein the iron compound in the aqueous mixture including the catalyst, the iron compound, the alumina compound, and the water includes an iron oxide hydroxide selected from a goethite, an akageneite, a lepidocrocite, or a combination thereof.

Element C70: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein the iron compound in the aqueous mixture including the catalyst, the iron compound, the alumina compound, and the water includes an includes a goethite.

Element C71: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein the aluminum compound in the aqueous mixture including the catalyst, the aluminum compound, and the water includes an aluminum oxide.

Element C72: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein the aluminum compound in the aqueous mixture including the catalyst, the aluminum compound, and the water includes an aluminum oxide hydroxide.

Element C73: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein the aluminum compound in the aqueous mixture including the catalyst, the aluminum compound, and the water includes an aluminum oxide hydroxide selected from a gibbsite, a bayerite, a boehmite, or a combination thereof.

Element C74: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein the aluminum compound in the aqueous mixture including the catalyst, the aluminum compound, and the water includes a boehmite.

Element C75: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein removing a substantial amount of water from the aqueous mixture including the catalyst, the iron compound, the aluminum compound, and the water to provide a precatalyst material includes heating the aqueous mixture at a temperature from about 50° C. to about 100° C.

Element C76: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein removing a substantial amount of water from the aqueous mixture including the catalyst, the iron compound, the aluminum compound, and the water to provide a precatalyst material includes heating the aqueous mixture at a temperature of about 80° C.

Element C77: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein removing a substantial amount of water from the aqueous mixture including the catalyst, the iron compound, the aluminum compound, and the water to provide a precatalyst material includes removing from about 50 wt. % to about 99 wt. % of the water.

Element C78: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein heating the precatalyst material to provide the catalyst material includes heating the precatalyst material at a temperature from about 300° C. to about 500° C.

Element C79: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein heating the precatalyst material to provide the catalyst material includes heating the precatalyst material at a temperature from about 350° C. to about 450° C.

Element C80: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein heating the precatalyst material to provide the catalyst material includes heating the precatalyst material in the presence of air, an oxidizing atmosphere, an inert atmosphere, or a combination thereof.

Element C81: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein heating the precatalyst material to provide the catalyst material includes heating the precatalyst material the presence of air.

Element C82: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein the catalyst material is further treated with a gas including ethane.

Element C83: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein the catalyst material is further treated with a gas including ethane; and wherein the gas further includes oxygen.

Element C84: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein the catalyst material is further treated with a gas including ethane; wherein the gas further includes ethylene.

Element C85: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein the catalyst material is further treated with a gas including ethane; and wherein the catalyst material is further treated with the gas including ethane at a temperature from about 100° C. to about 500° C.

Element C86: Wherein the catalyst material is prepared by a method that includes providing a catalyst including molybdenum, vanadium, and oxygen, preparing an aqueous mixture including the catalyst, an iron compound, an aluminum compound, and a water, removing a substantial amount of the water from the aqueous mixture to provide a precatalyst material, and heating the precatalyst material to provide the catalyst material; and wherein the catalyst material is further treated with a gas including ethane; and wherein the catalyst material is treated with the gas including ethane for about 18 hours to about 72 hours.

By way of non-limiting example, exemplary element combinations applicable to Embodiment C include: C1 and C4; C1 and C9; C1, C4, and C21; C1, C9, and C21; C1, C4, and C24; C1, C9, and C24; C1, C4, and C28; C1, C9, and C28; C1, C4, C21, and C28; C1, C9, C21, and C28; C1, C4, and C30; C1, C9, and C30; C1, C4, and C70; C1, C9, and C70; C1, C4, and C74; C1, C9, and C74; and C1, C4, C70, and C74; C1, C9, C70, and C74.

EXAMPLES

General Procedures

Reagents

Reagents purchased from manufacturers were used as received without further purification, unless noted otherwise. All reagents, with the exception of alumina, were purchased from SIGMA ALDRICH®. The supplied certificates of analysis for ammonium molybdate ($(NH_4)_6Mo_7O_{24}\cdot4H_2O$) and vanadium (IV) oxide sulfate hydrate ($VOSO_4\cdot3.46H_2O$ and $VOSO_4\cdot3.36H_2O$) were used to establish the hydrate content for different batches. $VOSO_4\cdot3.46H_2O$ and $VOSO_4\cdot3.36H_2O$ (97% purity) were confirmed by ICP-MS analysis. Vanadium and sulfur components were confirmed by $KMnO_4$ titration. $(NH_4)_6Mo_7O_{24}\cdot4H_2O$ (81-83% purity) was confirmed for nitrate, aresenate, phosphate, silicate and sulfate specifications by ICP-MS. Heavy metal, magnesium, potassium and sodium specifications were determined by ICP-OES. Three different grades of sodium dodecyl sulfate (SDS, SIGMA-ALDRICH®) surfactant were used, but the type of grade had no effect on the synthetic results. The purity of the various grades were 92.5-100.5%, ≥95%, and ≥99.0% purity. The purity range of the first grade was established by SIGMA-ALDRICH® using various methods including: titration (based on total alkyl sulfate content), purity based via GC (total lauryl sulfate, sodium salt), total water content determined by Karl Fisher titration, and total sodium content. More specifically, the ranges listed above were determined by titration based on the total alkyl sulfate content in the sample.

Three different types of alumina were investigated. VERSAL™ Alumina V-250 was manufactured from UOP, ALUMAX® PB250 was manufactured from PIDC and CATAPAL® B Alumina was manufactured from Sasol.

Distilled water was prepared inhouse using a Corning Mega Pure 12A System ACS as distillation apparatus.

MRU

The ability of catalysts and catalyst materials described herein to participate in the oxidative dehydrogenation of ethane was tested in a microreactor unit (MRU).

Figure 17:
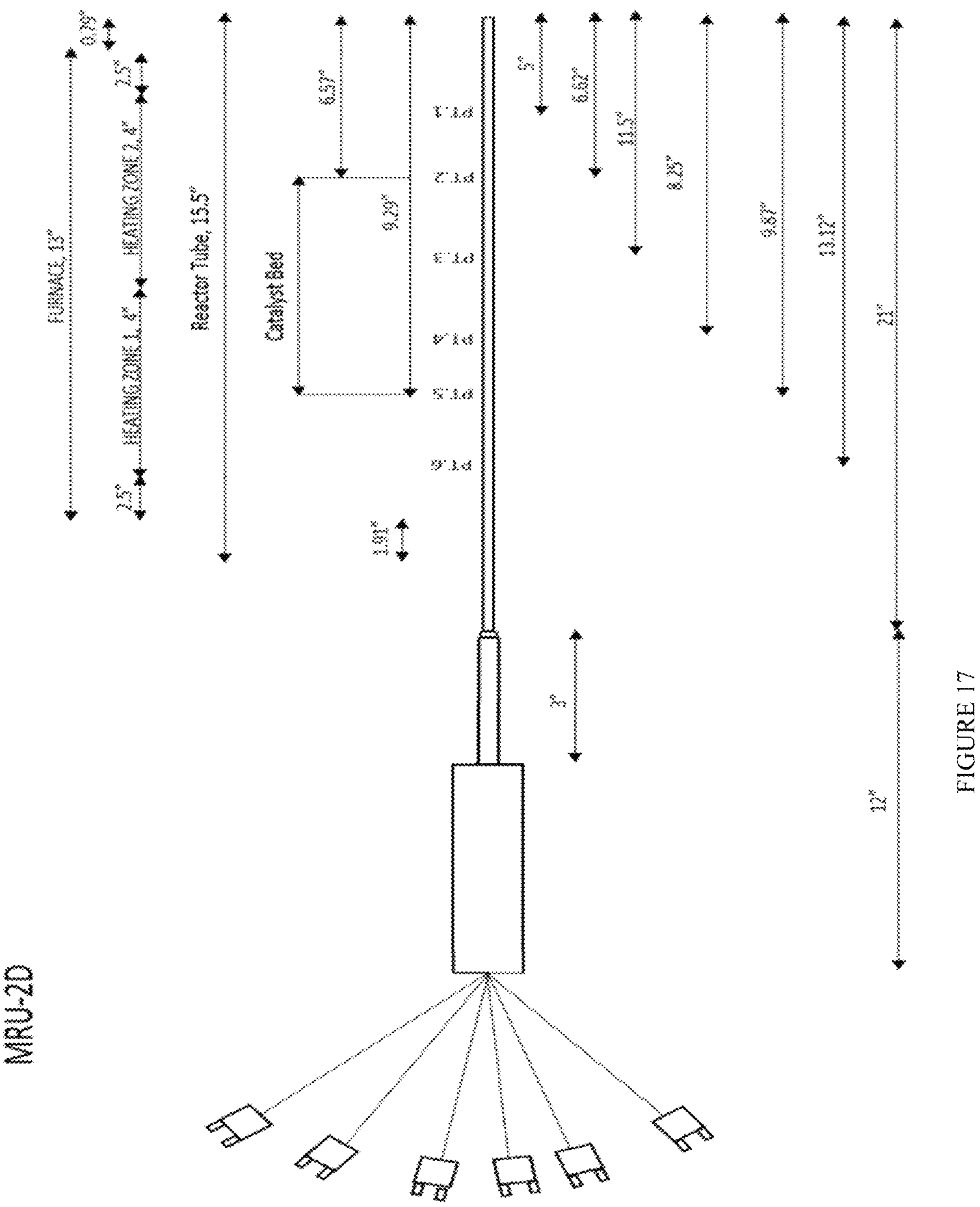
FIG. 17 shows MRU Reactor 2 thermocouple drawing with catalyst/heating zone location.

The MRU included a reactor tube made from SS316L stainless-steel SWAGELOK® Tubing, which had an outer diameter of 0.5 inches, an internal diameter of about 0.4 inches, and a length of about 15 inches. A 6-point WIKA Instruments Ltd. K-type thermocouple (as shown in FIGS. 17 and 18) having an outer diameter of 0.125 inches was inserted axially through the center of the reactor, which was used to measure and control the temperature within the catalyst bed. A room temperature glass tight sealed condenser was located after the reactor to collect water/acidic acid condensates. The gas product flow was allowed to either vent or was directed to a gas chromatography (Agilent 6890N Gas Chromatograph, using CHROMPERFECT®-Analysis, Version 6.1.10 for data evaluation) via a sampling loop.

To prepare catalyst and catalyst materials for testing in the MRU, the catalyst or catalyst material was loaded into a 1-inch round die and pressed with 8 tons of compression force for 10 to 15 seconds of dwelling time. The pressed catalyst or catalyst material was then crushed into small pieces using a mortar and pestle. The crushed catalyst or catalyst material was sieved and a particle sizes between 425 μm and 1 mm were collected to be loaded for testing on the MRU.

For MRU experiments, the catalyst bed was prepared by Method 1 or Method 2. Method 1 was employed to test catalysts and catalyst materials. Method 2 was employed to test catalyst materials.

Method 1. 1.96-3.00 g of catalyst or catalyst material was physically mixed with quartz sand such that the catalyst bed had a total volume of about 3-6 mL.

Method 2. Under this method, the catalyst bed consisted only of catalyst material. Further, the amount of catalyst material was determined based on the amount of catalyst used to prepare the catalyst material. Specifically, the catalyst material was loaded in an amount such that the theoretical amount of (i) catalyst or (ii) catalyst and iron in the catalyst bed was 1.96-3.00 g. For example, if a catalyst material was prepared from 40 wt. % catalyst and 60 wt. % alumina, then 4.91 g of catalyst material would be used to prepare the catalyst bed. Likewise, if a catalyst material was prepared from 30 wt. % catalyst, 10 wt. % goethite, and 60 wt. % alumina then 4.91 g of catalyst material would be used to prepare the catalyst bed. The catalyst or catalyst material can be diluted with filler up to 8 mL.

Figure 15:
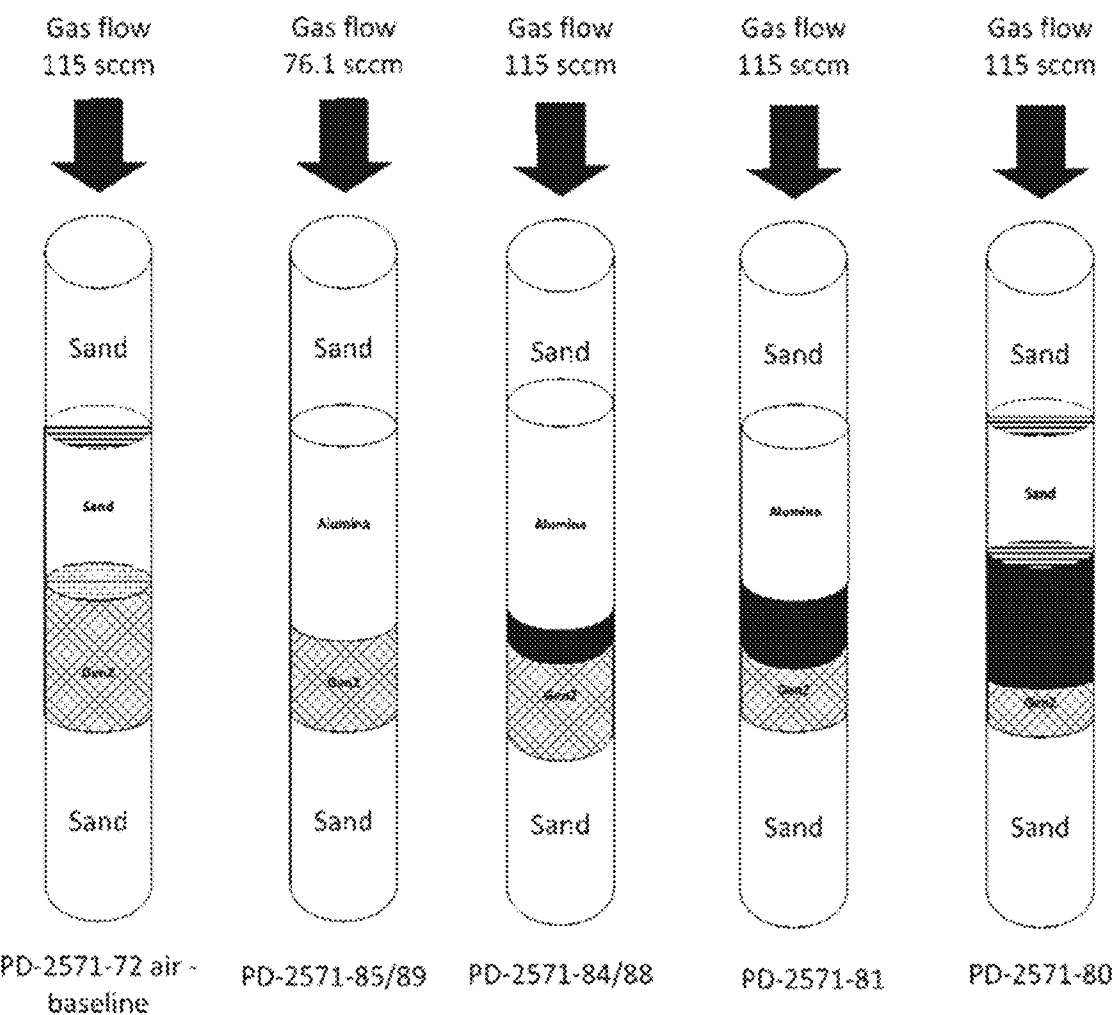
FIG. 15 shows the Micro Reactor Unit loading for Catalyst 1.1 and Catalyst Materials 2.1-2.4.
Figure 16:
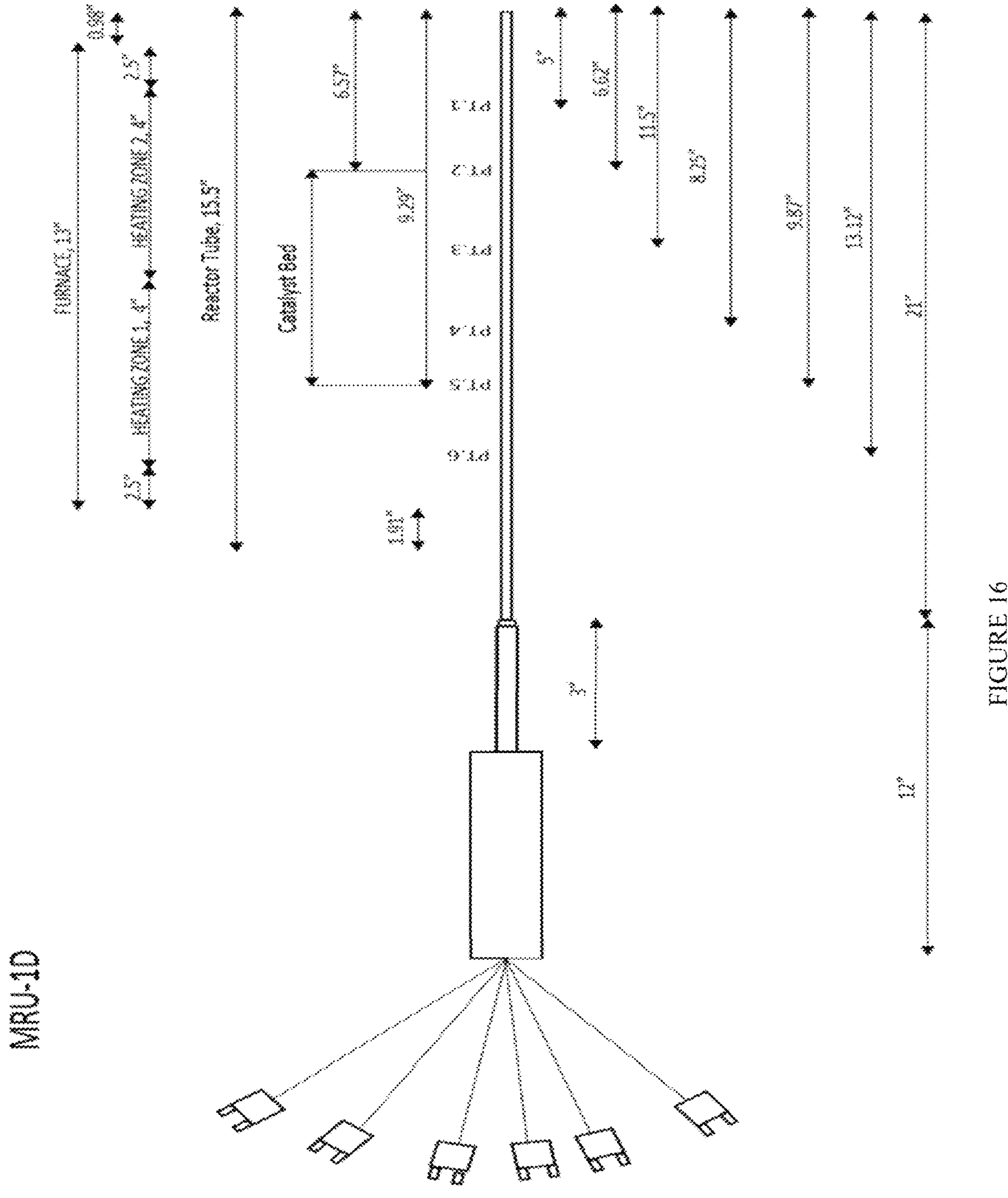
FIG. 16 shows MRU Reactor 1 thermocouple drawing with catalyst/heating zone location.

For both Methods 1 and 2, the catalyst bed was loaded in the middle zone of the reactor—located between points 2 and 5 of the thermocouple—and the remaining volume of the reactor was packed with quartz sand (see FIGS. 15 and 16). The load was then secured with glass wool on the top and the bottom of reactor.

For the MRU testing, a pre-mixed feed gas was fed through the reactor. The pre-mixed feed gas entering the reactor was 36 mol. % ethane, 18 mol. % oxygen, and 46 mol. % nitrogen. Further, the pre-mixed feed gas flow was adjusted by a calibrated mass flow controller to obtain a gas hourly space velocity (GHSV) of about 3,000 $h^{-1}$, based on the catalyst or catalyst material volume in the catalyst bed as defined by Method 1 or Method 2.

The flow rate of the feed gas was about 70 standard cubic centimeters per minute (sccm) to about 80 sccm (e.g., about 76.1 sccm). The catalyst bed placed in the reactor tube can include the catalyst or catalyst material and a filler. With reference to the MRU's catalyst bed, a filler refers to a material that does not participate in the oxidative dehydrogenation of ethane or have other catalytic activity, such as non-selective oxidation under the MRU test conditions. The filler employed was quartz sand. The catalyst or catalyst material can be diluted with filler up to 8 mL.

The 35% conversion temperature is determined at a weight hourly space velocity (WHSV) of 2.90 $h^{-1}$, with the WHSV based on the amount of catalyst or the amount of catalyst used to prepare the catalyst material, and a gas hourly space velocity (GHSV) of about 3,000 $h^{-1}$. Whereby WHSV is defined as mass flow of feed gas to the reactor divided by the weight of the catalyst in the catalyst bed, GHSV is defined as volumetric flow of the reactor feed gas divided by the volume of the catalyst bed.

Typically, the inlet pressure was in the range of about 1 pound per square inch gauge (psig) to about 2.5 psig and the outlet pressure is in the range of about 0 psig to about 0.5 psig.

The gas exiting the reactor was analyzed by gas chromatography (Agilent 6890N Gas Chromatograph, using CHROMPERFECT®-Analysis, Version 6.1.10 for data evaluation) to determine the percent of various hydrocarbons (e.g., ethane and ethylene) and, optionally, other gases such as $O_2$, $CO_2$, and CO and acetylene.

A catalyst or catalyst material's 35% conversion temperature was determined as follows. Conversion of the feed gas was calculated as a mass flow rate change of ethane in the product compared to feed ethane mass flow rate using the following formula:

$$C = \left(\frac{2 * X_{Ethylene} + X_{CO2} + X_{CO}}{2 * X_{Ethylene} + 2 * X_{Ethane} + X_{CO2} + X_{CO}}\right) * 100\%$$

In the above equation, C is the percent of feed gas that has been converted from ethane to another product (i.e., ethane conversion) and X is the molar concentration of the corresponding compound in the gaseous effluent exiting the reactor at corresponding temperature. The ethane conversion was then plotted as a function of temperature to acquire a linear algebraic equation. The linear equation for ethane conversion was solved to determine the temperature in which the ethane conversion was 35% (i.e., the 35% conversion temperature).

Further, the gas exiting the reactor was analyzed by gas chromatography to determine catalyst or catalyst material selectivity to ethylene (i.e., the percentage on a molar basis of ethane that forms ethylene). Selectivity to ethylene was determined using the following equation:

$$S_{Ethylene} = \left(\frac{2 * X_{Ethylene}}{2 * X_{Ethylene} + X_{CO2} + X_{CO}}\right) * 100\%$$

In the above equation, $S_{Ethylene}$ is the selectivity to ethylene and X is the molar concentration of the corresponding compound in the gaseous effluent exiting the reactor at corresponding temperature. The selectivity to ethylene was determined at the 35% conversion temperature, unless otherwise indicated. As such, after the 35% conversion temperature was determined, the above equation for selectivity was solved using the corresponding values for $X_{Ethylene}$, $X_{CO2}$, and $X_{CO}$ at the 35% conversion temperature.

When reported, acetic acid production was determined by running MRU testing long enough to collect an aqueous condensate in the condenser (e.g., 1-3 days). After collecting a sample of the condensate, the sample was submitted for liquid GC analysis (Agilent 6890N Gas Chromatograph, using CHROMPERFECT®-Analysis, Version 6.1.10 for data evaluation). To perform the liquid GC analysis, 300-450 mg of liquid sample was transferred to a scintillation vial. Next, 25 mg of isopropanol (IPA) was added as an internal standard. Further, 18-20 mL of distilled $H_2O$ was added to dilute the sample. Prepared samples were then transferred to GC vials and set in sequence to tested using an auto sampler. The GC analysis was a split injection method with a temperature program and flame ionization detector (FID). Further, a set of 3 calibration standards were run in duplicate for the relative response factor used for calculating acetic acid content in sample.

ICP-MS

Inductively Coupled Plasma Mass Spectrometry (ICP-MS), sensitive enough to detect elements in ppb concentration ranges, was one of the analytical techniques used for measuring the elemental composition of catalyst or catalyst materials. ICP-MS analysis was performed on an Agilent 7700X ICP-MS system. Quantitative determination of atoms' concentration in the samples were determined with the use of an external standard calibration. The calibration curves were constructed after subtracting the reagent blank. Concentrations were given in ng/mg (wt-ppm) or μg/g (wt-ppm) units in this analysis.

General ICP-MS Procedure for Catalysts Containing Molybdenum and Vanadium.

Samples were prepared by placing 10 milligram (mg) of catalyst or catalyst material in either 3 milliliters (mL) of 10-15 wt. % NaOCl solution or 3 mL of a 6.25-35.0 molar (M) NaOH solution. The solution was then heated in an oil bath at 90° C. with rigorous mixing.

ICP Digestion Method 1:

NaOCl solutions produced a clear, yellow solution within 5-10 minutes upon heating at 90° C. with vigorous mixing. After mixing the NaOCl solution at 90° C. for an additional 12 hours, a small amount of fine yellow precipitate formed. The precipitate was allowed to settle to the bottom of the mixing vial, and the mother liquor was used for the ICP-MS sample work up and injection. The diluted solution was then further diluted 10-100× using 5% nitric acid and analyzed by ICP-MS.

ICP Digestion Method 2:

NaOH solutions produced homogenous samples for ICP-MS experiments after 12-24 hours of heating and mixing and resulted in a clear, brown solution. After dissolution was complete, the resulting solution was diluted to a final volume of 60-80 mL with distilled water.

The diluted solution was then further diluted 10-100× using 5% nitric acid and analyzed by ICP-MS.

The multi-element scan optimized the instrument parameters to scan for trace (ppb) levels of 50+ elements. The 50+ elements included in the multi-element scan included Fe and Al. When scanning for Mo, V, Al, and Fe, higher concentrations of calibration standards were used and the instrument sensitivity was reduced as the elements of interest were found in percent levels. This was done by preparing calibration standards for each of the four elements. These calibration standards were prepared in percentage levels in high concentrations. Normally, calibration standards were prepared in ppm level concentrations. The ICP-MS program was developed such that the four elements Mo, V, Al, and Fe were detected with a high degree of accuracy. The elements that were normally calibrated to ppm level concentrations were excluded as the detector was calibrated for only the four elements at high percentages.

General ICP-MS Procedure for Catalyst Materials Containing Molybdenum and Vanadium.

ICP Digestion Method 3:

Catalyst materials including (i) molybdenum, vanadium, oxygen, and iron, and (ii) molybdenum, vanadium, oxygen, aluminum, and iron were digested in an oxalic acid or an NaOCl solution to produce a suitable homogenous sample for ICP-MS.

Approximately 10 mg of catalyst material and 2-3 g of oxalic acid were added to a vial. Then, 2-3 mL of distilled water was added to create a suspension. The suspension was heated in an oil bath at 90° C. with rigorous mixing. Dissolution of the catalyst generally took 24-72 hours to produce a homogenous, blue solution. After dissolution was complete, the resulting solution was diluted to a final volume of 60-80 mL. The diluted solution was then further diluted 10-100× using 5% nitric acid and analyzed by ICP-MS.

CHN Analysis

Carbon, hydrogen, and nitrogen (CHN) analysis was performed on select samples using a LECO® CHN628 Series Determinator, using a combustion technique. A pre-weighed and encapsulated sample was placed in the instrument's loader where the sample was transferred to the instrument's purge chamber directly above the furnace, eliminating atmospheric gases from the transfer process. The sample was then introduced to the primary combustion furnace, which contained only pure oxygen. This results in a rapid and complete oxidation. Carbon, hydrogen, and nitrogen present in the sample are oxidized to form $CO_2$, $H_2O$, and $NO_x$ gases, respectively, and are swept by the oxygen carrier through a secondary furnace for further oxidation and particulate removal.

The combination gases are then collected in a vessel known as a ballast for equilibration. The homogenized gases from the ballast are swept through a 10 $cm^2$ aliquot loop and, using an ultra-high purity helium carrier gas, on to the detectors. Separate, optimized non-dispersive infrared (NDIR) cells are utilized for the detection of $CO_2$ and $H_2O$. The $NO_x$ gases are passed through a reduction tube filled with copper to reduce the $NO_x$ gases to $N_2$ and remove any excess oxygen present from the combustion process. The aliquot gas then passes through scrubbers to remove $CO_2$ and $H_2O$ and onto a thermal conductivity cell (TC) utilized to detect the $N_2$. Prior to every set of samples, the instrument is calibrated using certified standards.

XRD

Instrument

Powder X-Ray Diffractometry (PXRD) data was collected using a PANalytical Aeris X-ray diffractometer by SEMx Incorporated. This diffractometer instrument consisted of three basic elements: X-ray tube, sample holder, and X-ray detector. X-rays were generated in a cathode ray tube (Cu source with Kα radiation=1.5418 Å) with the resulting X-rays being directed onto the sample. As the sample and detector are rotated, the intensity of the reflected X-rays is recorded to produce characteristic X-ray spectra. When the incident X-rays reflecting off the sample satisfies the Bragg Equation ($n\lambda=2d \sin \theta$), constructive interference occurs and a peak in intensity occurs (y-axis). X-ray diffractometers were setup such that the sample rotates in the path of the X-ray beams at an angle θ, while the X-ray detector is mounted on an arm to collect the diffracted X-rays and rotates at an angle of 2θ from ~5° to 70° (x-axis).

Qualitative XRD analysis and Rietveld Refinement was performed using HighScore Plus XRD analysis software. The samples were finely ground to reduce particle size and to obtain a uniform mixture. They were then loaded onto the XRD sample holder and the XRD spectrum was acquired. The Rietveld Refinement results were combined with Highscore Plus and EDS results to perform qualitative and quantitative analysis.

Amorphous Content Determination

The weight percentage of amorphous content was determined by external standard. With an external standard phase, the instrument intensity constant, K-factor, is determined. Corundum was used as the external standard and was measured with the same instrument configuration shortly after the unknown sample was measured. The K-factor approach is described by O'Connor and Raven: 1988, Powder Diffraction, 3 (1), 2-6. For each sample, the weight percentage of the crystalline $MoVO_x$ orthorhombic phase had to be determined in order to assign weight percentages to the amorphous content. The Degree of Crystallinity (DOC) Method, based on the estimation that the total intensity of area contributed to the overall diffraction pattern by each component in the analysis, was used to determine the amount of amorphous phase. The degree of crystallinity was calculated from the total areas under the defined crystalline and amorphous components from:

$$DOC = \text{Crystalline Area Crystalline Area} + \text{Amorphous Area}$$

Where the weight fraction of the amorphous material was calculated from:

$$W_{amorphous} = 1 - DOC$$

The Ortho-$MoVO_x$ phase contributed to the crystalline area and therefore needed to be quantified in order to determine the amorphous area. To compensate for the fact that different materials and backgrounds would have different effects, a sample of $MoVTeNbO_x$ was used to calibrate some constants needed for the DOC method. Samples containing $MoVO_x$ phases had the ortho-$MoVO_x$ phase weight percentages qualitatively determined using only two elements (Mo and V) based on the $MoVTeNbO_x$ calibration.

M1 Phase Content Determination

The $MoVO_x$ orthorhombic phase (also referred to in literature as the M1 phase) was fitted using literature crystal structure data for a different yet crystallographically analogous compound because the orthorhombic Pba2 crystalline phase was a match. $MoVSbO_x$ XRD simulation: W. Ueda, D. Vitry, T. Kato, N. Watanabe, Y. Endo, 2006, Res. Chem. Intermed. 32(3-4), 217-233. Lattice parameters: a=21.124 Å, b=26.598 Å, c=4.0076 Å

Comparative Raw Data Analysis

The PXRD raw data was also analyzed using a Python code through the program Spyder. The code generated overlaid plots. It also analyzed the data by comparing the peak prominence of all the local maxima and generated a plot with peaks meeting an established threshold. Relevant catalyst peaks are highlighted in the plot with vertical lines and the range of the relative peak intensities were provided by the code. The relative peak intensities were calculated as a percentage of the 22.2° 2θ reflection and a maximum and minimum value was created based on the selection of catalysts to be processed by the python code

SEM

Scanning electron microscope (SEM) images were collected using a JSM-IT300LV INTOUCHSCOPE™. Samples were prepared on an aluminum stud with double sided carbon tape.

SEM-EDS

Energy-dispersive X-ray spectroscopy (EDS) was conducted using a JEOL JED-2300 DRY SDD EDS detector. Samples were sent to SEMx Incorporated for EDS analysis. The samples were finely ground to reduce particle size and obtain the uniform mixture. They were then loaded onto EDS stub for analysis by SEM. EDS was used for elemental analysis and surface examination. EDS is a micro-analytical technique that provides a semi-quantitative elemental analysis of the surface of a sample (e.g., the top 1 to 3 microns). The SEM was used to examine the surface morphology at magnifications ranging from 20 to 100,000 times. The EDS instrument detects elements with an atomic number equal or greater than sodium, but also has light element capability, which means that it can also detect carbon, nitrogen, oxygen, and fluorine. The estimated lower detectable limit for any given element generally is between about 0.2 and 0.5 wt. %.

PSD by SEM

Samples were sent to SEMx Incorporated for particle size analysis using scanning electron microscopy (SEM), model JEOL-JSM300 LV. SEM was used to observe and count the particles in the sample to obtain the Particle Size Distribution (PSD). For the PSD measurements, the SEM instrument took pictures at different magnifications. Measurements were done for 400-800 particles at different magnifications to cover the size range (statistical population). Size was measured by length in micrometers and was measured on the longest dimension of the particles. SEM based PSD is a method for analyzing samples where particles are agglomerated (stuck together) because the analyst can visually see this through the microscope and make the judicious decision to measure the distinct particles rather than the agglomerates. Statistics and analysis were based on total counts measured by SEM.

Pore Volume, BET Surface Area Analysis, and BJH Pore Size Distribution Analysis

Gas adsorption manometry was used for the determination of adsorption isotherms of nitrogen at the temperature of liquid nitrogen (approximately 77 K). The amount of gas adsorbed was evaluated by measuring the change in gas pressures. Isothermal nitrogen adsorption processes were measured, and surface areas and volumes were calculated.

Total pore volume was calculated by nitrogen gas uptake at the relative pressure $P/P_0=0.99$.

Brunauer-Emmett-Teller (BET) analysis was applied to quantify the specific surface area ($m^2/g$) of the solid samples. BET valuations were performed by multilayer adsorption of nitrogen and measured as a function of relative pressure. Applying BET analysis allows for a quantitative comparison of solids' surface areas by determining the monolayer capacity from nitrogen multilayer adsorption experiment. Monolayer capacity is a representation of total specific surface area and encompasses both the external area and pore area of porous solid.

The Barrett-Joyner-Halenda (BJH) method was used for calculating pore size (A) distributions from experimentally collected adsorption isotherms using the Kelvin model of pore filling ($cm^3/g \cdot A$). This technique characterizes pore size distribution independently of external area due to particle size of the sample and can be applied to mesopore and small macropores.

Nitrogen physisorption experiments were performed on a TriStar (MICROMERITICS® Instruments) by the University of Calgary. Samples were analyzed by nitrogen adsorption at 77 K. The as-received samples were loaded into physisorption cells. The samples were degassed at 200° C. for 1 hour prior to the adsorption experiments.

Yield Calculations

Theoretical Yield calculations were based on the weight of each reagent used.

The weight of each reagent used in grams was divided by the molecular weight of the compound in grams per mol. For example:

Weight $(NH_4)_6Mo_7O_{24}\cdot 4H_2O$ (g)/Molecular weight $$(NH_4)_6Mo_7O_{24}\cdot 4H_2O\ (g/mol) = (NH_4)_6Mo_7O_{24}\cdot 4H_2O\ \text{mol}$$

This calculation was performed for the vanadium as well.

The theoretical moles of the final product was predicted by assuming that both the molybdenum and the vanadium have attained the highest oxidation states in the final product. Thus, molybdenum and vanadium formed $MoO_3$ and $V_2O_5$ respectively.

The moles of the starting material was used and multiplied by the respective molar equivalents of each of the total oxidized species. The moles were then multiplied by the predicted theoretical weight of the fully oxidized final product in order to get the final theoretical weight of the catalyst. For example:

Theoretical Weight of Molybdenum in the Fully Oxidized State:

$$(NH_4)_6Mo_7O_{24}\cdot 4H_2O\ \text{mol}\times 7 = 7\ (MoO_3\ \text{mol})$$

$$((MoO_3\text{mol}))\times MoO_3\ g/mol) =$$

$$\text{Theoretical weight of fully oxidized molybdenum in grams}$$

Theoretical Weight of Vanadium in the Fully Oxidized State:

$$(VOSO_4\cdot 3.46H_2O\ \text{mol}\times 1/2 = 1/2\ V_2O_2\ \text{mol})$$

$$(V_2O_5\ \text{mol}\times V_2O_5\ g/mol) =$$

$$\text{Theoretical weight of fully oxidized vanadium in grams}$$

$$\text{Total theoretical weight in g} =$$

$$(\text{Theoretical weight of fully oxidized molybdenum in grams}) +$$

$$(\text{Theoretical weight of fully oxidized vanadium in grams})$$

$$\text{Percent yield} = (\text{Actual measured yield (g)/Theoretical yield (g)})\times 100$$

The percent yield was determined by diving the actual measured yield by the theoretical yield and multiplying by 100.

Synthesis of Catalysts Including Mo, V, and O

Catalysts containing molybdenum and vanadium were synthesized on a small scale (i.e., in a 600 mL reactor) and on a large scale (i.e., in a 2,000 mL reactor) from ammonium molybdate ($(NH_4)_6Mo_7O_{24}\cdot 4H_2O$) (SIGMA-ALDRICH) and vanadium (IV) oxide sulfate hydrate ($VOSO_4\cdot 3\cdot xH_2O$) (SIGMA-ALDRICH).

General small-scale procedure. $(NH_4)_6Mo_7O_{24}\cdot 4H_2O$ (SIGMA-ALDRICH®) (13.26 g) was weighed into a round bottomed flask. The white solid was dissolved in 180 mL ($2.98\times 10^{-2}$ mol/L) of distilled water with aid of a 60° C. warm water bath and stirring to provide a clear, colorless solution. $VOSO_4\cdot 3\cdot xH_2O$ (4.22 g) was weighed into a glass beaker. The blue solid was dissolved in 180 mL ($5.20\times 10^{-2}$ mol/L) of distilled water with aid of a 60° C. warm water bath and stirring to provide a clear, blue solution. The blue $VOSO_4$ (aq.) solution was added either all-at-once or drop-wise to the colorless $(NH_4)_6Mo_7O_{24}$ (aq.) solution to produce a dark purple opaque solution. The resulting solution was stirred for 30 minutes at 60° C. The pH of the solution was measured with a pH probe to be 2.70 before addition of surfactant.

After 0-30 minutes, 4.05 g of sodium dodecyl sulfate surfactant (SDS) (SIGMA-ALDRICH®) was added as a white powder to the dark molybdenum and vanadium solution to produce an emulsified slurry. The purple-emulsified slurry was stirred for 30 minutes at 60° C. The pH of the SDS containing slurry was measured to be 2.70.

After the 30 minutes, the purple slurry was added to a glass or Teflon liner and the liner was added to a stainless-steel high-pressure PARR reactor. The reactor was sealed and purged ten times by alternating with 15 psig (pounds per square inch gauge) nitrogen gas and vacuum, then left under 15 psig nitrogen and sealed. The reactor was then placed into an oven or heating jacket and heated to 220-230° C. The temperature was estimated through a thermowell filled with Dow Corning 510 silicon oil in the cases were a heating jacket was employed, or it was the temperature the oven was set to. The reaction was allowed to proceed at 220-230° C. either being stirred at 150 rpm or at a stand-still for 20-48 hours before being allowed to cool to room temperature.

Once cooled, the reactor was vented, opened, and the resulting spongy-slurry was filtered. The solids were washed with water (0.5-3.0 L) until the filtrate ran clear. The solids were optionally washed with one or any combination of ethanol, ethyl acetate, and aqueous oxalic acid. Alternatively, the solids were optionally air treated. The washing step was able to remove the oil-like products produced by the decomposition of SDS during the hydrothermal reaction. The effectiveness of the washing step was, optionally, monitored by CHN elemental analysis—and was typically performed until the wt. % carbon was less than 1 wt. %. The washing step was not required when an air calcination was employed—which is discussed below. Further, the washed solids were purple or grey in color. Subsequently, the solids were dried at 90° C. overnight and the next morning the dry solids were weighed producing a yield of 35-55%. The spongy solids were optionally ground into powder prior to calcination.

For air calcination, the following general procedure was employed. The pre-calcined catalyst was loaded into a ceramic bowl and placed into a muffle furnace. The muffle furnace was programmed for the following calcination program: ramp to 280° C. over 30 minutes, dwell for 30 minutes at 280° C., ramp to 400° C. over 30 minutes, dwell for 6 hours at 400° C., and then cool to ambient temperature naturally. Typically, the calcined catalyst produced a weight yield of 93-96%.

For nitrogen calcination, the following general procedure was employed. The pre-calcined catalyst (catalyst obtained directly after filtration and drying at 90° C. from the hydrothermal reaction) was optionally treated in convective flow air at 280° C. for 3-26 hours to removal any organic residue before calcination. A quartz boat containing the precalcined catalyst was loaded into a quartz tube, which was placed into a split tube furnace. The quartz tube was purged with bulk nitrogen for 8 hours—with the nitrogen feed being passed through an oxygen scrubbing bed to further purify the nitrogen to less than 4 ppm oxygen prior to purging. Subsequently, the pre-calcined catalyst was calcined at 400° C. The heating program for the furnace was: 4 hours ramp from room temperature to 400° C., dwell at 400° C. for 2 hours and then cool to ambient temperature naturally. Calcined catalyst weight produced a weight yield of 93-96%.

Synthesis of Catalysts 1.1-1.6

Example 1: Synthesis of Catalyst 1.1 and 1.2

$(NH_4)_6Mo_7O_{24}\cdot 4H_2O$ (44.20 g) was added to a 2 L round bottom flask with a magnetic stir bar. Subsequently, approximately 600 mL of distilled water was added, and the $(NH_4)_6Mo_7O_{24}\cdot 4H_2O$ was dissolved with the aid of a 60° C. water bath. Next, $VOSO_4\cdot 3.46H_2O$ (SIGMA-ALDRICH®) (14.07 g) was placed into a 1 L beaker with a magnetic stir bar. Subsequently, approximately 600 mL of distilled water was added and the $VOSO_4$. $3.46H_2O$ was dissolved with the aid of a 60° C. water bath. Then, the vanadium solution was added to the round bottom flask containing the molybdenum solution while stirring at 60° C. Sodium dodecyl sulfate (SDS, SIGMA-ALDRICH®, 13.57 g) was added to the round bottom flask while stirring at 60° C., and the mixture was stirred for approximately 30 minutes at 60° C.

The round bottom flask was then removed from the water bath and allowed to cool before transferring the solution to a 2 L glass liner. The round bottom flask was rinsed with distilled water and the rinse was transferred to the glass liner. The glass liner containing the purple solution was inserted into a 2 L PARR reactor. The PARR reactor unit was sealed and subsequently, the PARR reactor headspace was pumped and purged ten times with nitrogen. The headspace was left under approximately 15 psig nitrogen and the top valve on the PARR reactor was closed. Subsequently, the PARR reactor was stirred at approximately 150 rpm using an overhead stirrer at a surface temperature from 230° C. to 247° C. for approximately 26 hours. The reaction mixture was then allowed to cool to room temperature (approximately 21° C.) and stirred at approximately 150 rpm for about 3.5 days.

The reaction mixture was filtered using a Buchner funnel, 4 qualitative filter papers, and an aspirator. The collected solid precalcined catalyst was rinsed with about 1 L of distilled water. Precaution was taken to prevent the filter cake from cracking. The pre-calcined catalyst was then washed with about 1 L of ethanol. The precalcined catalyst material was then dried overnight in an oven at approximately 90° C. The weight of the precalcined catalyst was 22.15 g.

Subsequently, a portion of the precalcined catalyst was ground manually using a mortar and pestle. The precalcined catalyst (5.94 g) was placed in a 100 mL beaker and calcined in a muffle furnace under the following conditions: ramp to 280° C. over 30 minutes, hold for 30 minutes at 280° C., ramp to 400° C. over 30 minutes, hold for 6 hours at 400° C., off. The catalyst was calcined and cooled to room temperature, yielding about 5.59 g of Catalyst 1.1.

Separately, the remaining 16.2 g of precalcined catalyst was transferred to a 400 mL beaker. The precalcined catalyst was placed in a muffle furnace and calcined using the same program: ramp to 280° C. over 30 minutes, hold for 30 minutes at 280° C., ramp to 400° C. over 30 minutes, hold for 6 hours at 400° C., off. The calcined catalyst (Catalyst 1.2) was greenish grey with a brownish layer on top.

For the purposes of catalyst performance testing and characterization, catalysts 1.1 and 1.2 were considered to be the same. Catalysts 1.1 and 1.2 were generated using the same calcination procedure except for weight of catalyst calcined in the last step.

Powder XRD data was collected on Catalyst 1.1 as per the general XRD procedure discussed above. The plot for Catalyst 1.1 is presented in FIGS. 1 and 2. The raw data PXRD plot was used in establishing the range of the peak intensities presented in Table 3 and Table 10.

Catalyst 1.1 was submitted for MRU testing. The results of the MRU testing are presented in Table 7.

Catalyst 1.2 was analyzed by EDS as per the general procedure SEM-EDS. Results are presented in Table 2 and Table 9.

Figure 7:
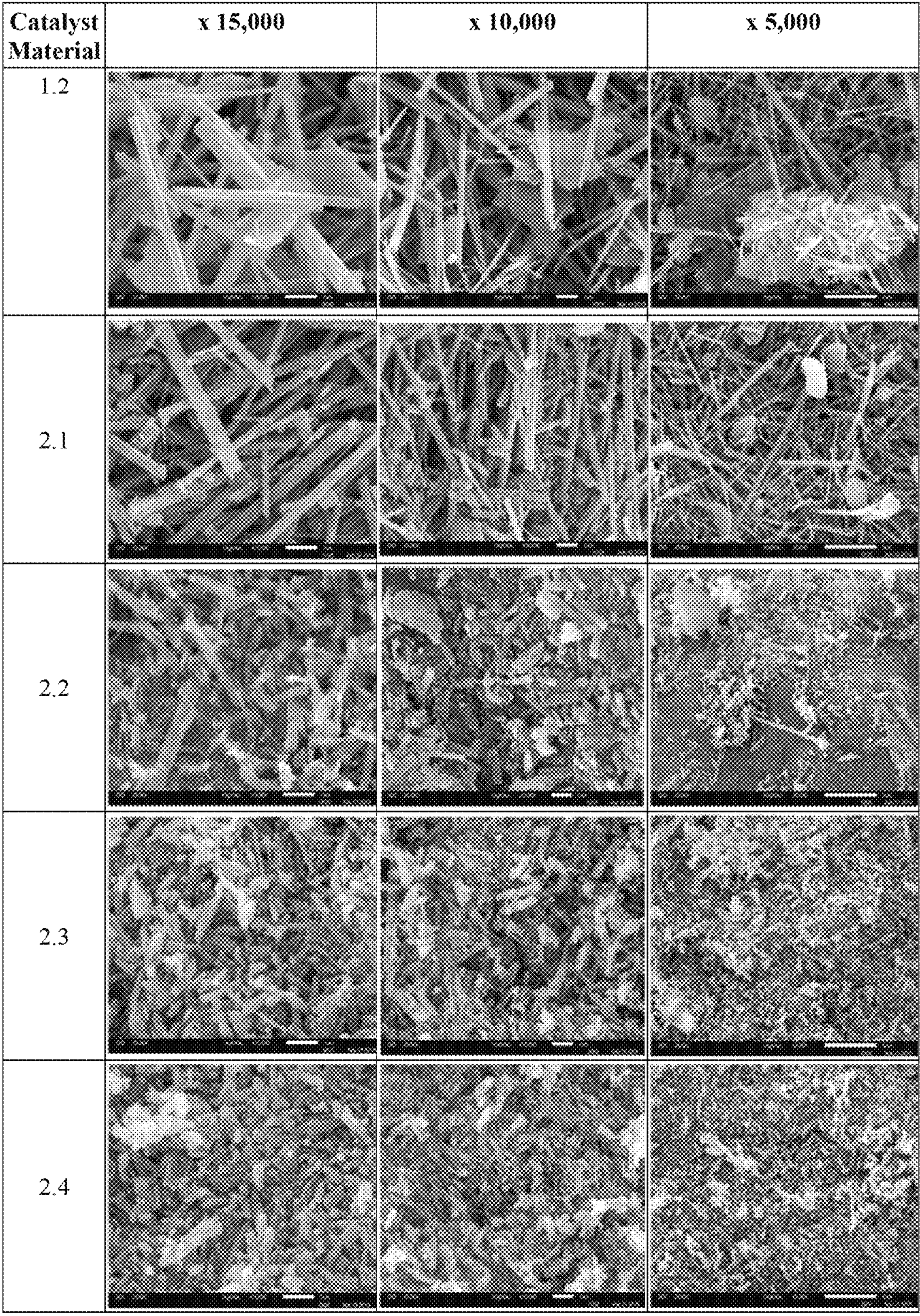
FIG. 7 shows the SEM images of Catalysts/Catalyst Materials 1.2 and 2.1-2.4.

Catalyst 1.2 was submitted for SEM imaging. The results are presented in FIG. 7.

Bulk density for Catalyst 1.2 measurements are presented in Table 6.

Example 2: Synthesis of Precalcined Catalyst 1.3

$(NH_4)_6Mo_7O_{24}\cdot 4H_2O$ (SIGMA-ALDRICH®) (44.30 g) was weighed in a 2 L round bottom flask. The white solid was dissolved in 600 mL of distilled water with the aid of a 60° C. warm water bath and stirring to create a clear, colorless solution. $VOSO_4\cdot 3.46H_2O$ (SIGMA-ALDRICH®) (13.99 g) was weighed into a 1 L beaker. The blue solid was dissolved in 600 mL of distilled water with the aid of a 60° C. warm water bath and stirring to create a clear, blue solution. The blue vanadium solution was added drop-wise via a dropper funnel to the colorless molybdenum solution to produce a black solution. The resulting black solution was stirred for 30 minutes at 60° C. Immediately after the completion of the addition of vanadium solution, 13.57 g of sodium dodecyl sulfate (SIGMA-ALDRICH®) surfactant was added as a powder to the black molybdenum-vanadium solution to produce a purple slurry with some emulsion present. The purple-emulsified slurry was stirred for 30 minutes at 60° C.

After 30 minutes, the purple slurry was added to a glass liner and the glass liner was added to a 2 L PARR high pressure reactor. The PARR reactor had a magnetic stir bar added inside the vessel. The PARR reactor was sealed and purged with 15 psig nitrogen gas and vacuum sequence ten times, then left under 15 psig nitrogen. The PARR reactor was setup in a heating mantle and heated via thermocouples and a temperature control box to 230° C. internal process temperature (temperature controller was set to 242° C.; the internal temperature was about 230° C. after running overnight). The reaction proceeded at 230° C. for 24 hours, with the slurry stirred via magnetic stirring, before being turned off and allowed to cool to room temperature.

Once cooled, the reactor was vented, opened, and the resulting slurry was filtered using a Buchner funnel and 4 layers of qualitative filter paper. The mother liquor was blue. The solids were washed with water (1.8 L) until the filtrate ran clear. The washed solids were dark purple in color with some brown oil present. The solids were washed with denatured ethanol (0.5 L) producing a yellow filtrate. The solids were then additionally washed with water (0.5 L). The resulting grey solids were dried at 90° C. overnight to produce precalcined Catalyst 1.3. Precalcined Catalyst 1.3 was manually ground and weighed to be 17.82 g.

Example 3: Synthesis of Catalyst 7.4

A 5.29 g portion of precalcined Catalyst 1.3 was loaded into beaker air calcination via a muffle furnace. The muffled furnace calcination proceeded using the following heating program: heat ramp 10 minutes to 280° C., dwell for 30 minutes, 20 minutes ramp to 400° C., dwell 6 hours then cooled. After the air calcination, the solid product was brown and yielded 5.06 g of Catalyst 1.4.

Catalyst 1.4 was then submitted for ICP-MS analysis using the general ICP-MS procedure described herein using digestion method 2. The results are presented in Table 1.

Catalyst 1.4 was analyzed by EDS as per the general procedure SEM-EDS. Results are presented in Table 2.

Powder XRD data was collected as per General Procedure XRD above. The plot for this Catalyst 1.4 is presented in FIG. 1. The raw data PXRD plot was used in establishing the range of the peak intensities presented in Table 3.

Figure 11:
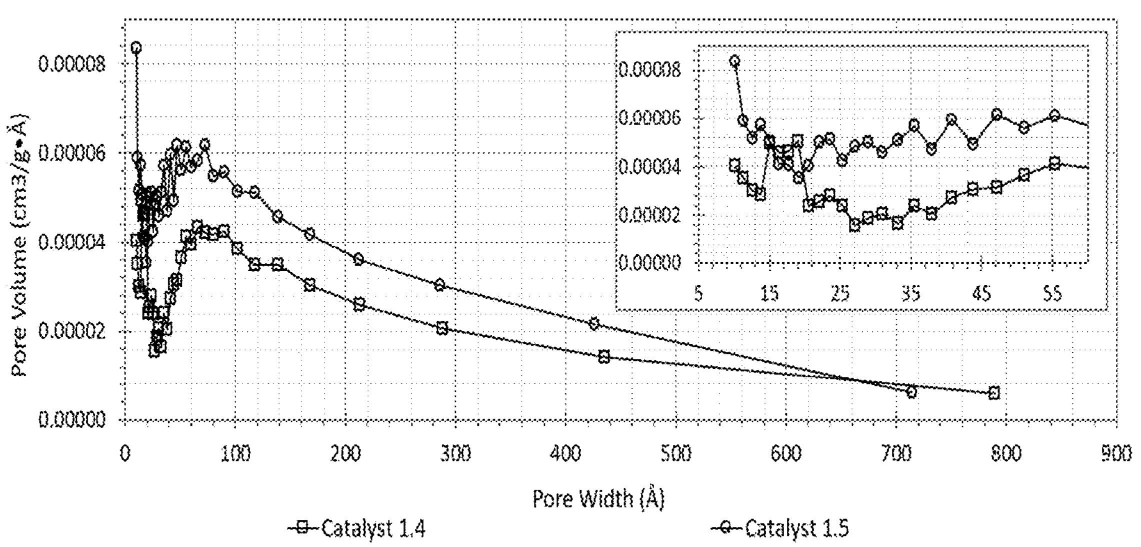
FIG. 11 shows the BJH plot for Catalysts 1.4 and 1.5.

Catalyst 1.4 was analyzed by nitrogen gas adsorption analysis for pore volume, BET surface area, and BJH pore size distributions analysis. Pore volume and BET surface area analysis results are presented in Table 5. BJH analysis results are presented in FIG. 11.

Catalyst 1.4 was submitted for MRU testing. The results of the MRU testing are presented in Table 7 and Table 30.

Example 4: Synthesis of Catalyst 1.5

$(NH_4)_6Mo_7O_{24}\cdot4H_2O$ (SIGMA-ALDRICH®) (13.26 g) was weighed in a 500 mL round bottomed flask. The white solid was dissolved in 120 mL of distilled water with the aid of a 60° C. warm water bath and stirring to create a clear, colorless solution. $VOSO_4\cdot3.46H_2O$ (SIGMA-ALDRICH®) (4.22 g) was weighed into a 500 mL round bottom flask. The blue solid was dissolved in 180 mL of distilled water with the aid of a 60° C. warm water bath and stirring to create a clear, blue solution. The blue vanadium solution was added dropwise to the colorless molybdenum solution to produce a black solution. To the black solution, sodium dodecyl sulfate (SIGMA-ALDRICH®) surfactant was added as a powder to produce a purple slurry with some emulsion present. The purple-emulsified slurry was stirred for 30 minutes at 60° C.

After 30 minutes, the purple slurry was added to a glass liner and the glass liner was added to a 600 mL PARR high pressure reactor. The PARR reactor was sealed and purged with 15 psig nitrogen gas and vacuum sequence ten times, then left under 15 psig nitrogen. The PARR reactor was setup with an external heating mantle, thermocouples, and a heat control box for conducting high temperature hydrothermal reaction. The hydrothermal reaction proceeded at 221-224° C. for 25 hours before being turned off and allowed to cool to room temperature.

Once cooled, the reactor was vented, opened, and the resulting slurry was filtered. The filtering was done using a Buchner funnel and 4 layers of qualitative filter paper. The mother liquor was blue. The solids were washed with 0.6 L of water, followed by 0.25 L of denatured ethanol. The solids were dried at 90° C. overnight to yield 6.23 g of precalcined catalyst.

A 3.19 g portion of the precalcined catalyst was loaded into a beaker for air calcination via a muffle furnace. The muffled furnace calcination proceeded using the following heating program: heat ramp 30 minutes to 280° C., dwell for 30 minutes, 30 minutes ramp to 400° C., dwell 6 hours then cooled. After the air calcination, the solid product was brown and yielded 3.06 g of green Catalyst 1.5.

Catalyst 1.5 was then submitted for ICP-MS analysis using the general ICP-MS procedure described herein using digestion method 3. The results are presented in Table 1.

Catalyst 1.5 was analyzed by EDS as per the general procedure SEM-EDS. Results are presented in Table 2.

Powder XRD data was collected as per the general XRD procedure discussed herein. The plot for this catalyst is available in FIG. 1. The raw data PXRD plot was used in establishing the range of the peak intensities presented in Table 3.

Catalyst 1.5 was analyzed by nitrogen gas adsorption analysis for pore volume, BET surface area, and BJH pore size distributions analysis. Pore volume and BET surface area analysis results are presented in Table 5. BJH analysis results are presented in FIG. 11.

Catalyst 1.5 was then submitted for MRU testing. The results are presented in Table 7.

Example 5: Synthesis of Catalyst 1.6

$(NH_4)_6Mo_7O_{24}\cdot4H_2O$ (SIGMA-ALDRICH®) (44.20 g) was added to a 2 L round bottom flask with a magnetic stir bar. Subsequently, approximately 600 mL of distilled water was added and the $(NH_4)_6Mo_7O_{24}\cdot4H_2O$ was dissolved with the aid of a 60° C. water bath. Next, $VOSO_4\cdot3.46H_2O$ (SIGMA-ALDRICH®) (14.07 g) was placed into a 1 L beaker with a magnetic stir bar. Subsequently, approximately 600 mL of distilled water was added and the $VOSO_4\cdot3.46H_2O$ was dissolved with the aid of a 60° C. water bath. Then, the vanadium solution was added to the round bottom flask containing the molybdenum solution while stirring at 60° C. Sodium dodecyl sulfate (SIGMA-ALDRICH®) (13.57 g) was added to the round bottom flask while stirring at 60° C., and the mixture was stirred for approximately 30 minutes at 60° C.

The round bottom flask was then removed from the water bath and allowed to cool before transferring the solution to a 2 L glass liner. The round bottom flask was rinsed with distilled water and the rinse was transferred to the glass liner. The glass liner containing the purple solution was inserted into a 2 L PARR reactor. The PARR reactor unit was sealed and subsequently, the PARR reactor headspace was pumped and purged ten times with nitrogen. The headspace was left under approximately 15 psig nitrogen and the top valve on the PARR reactor was closed. Subsequently, the PARR reactor was stirred at approximately 150 rpm using an overhead stirrer at a temperature from 230° C. to 232° C. for approximately 24 hours. The reaction mixture was then allowed to cool to approximately 28° C. and stirred at approximately 150 rpm for overnight.

The reaction mixture was filtered using a Buchner funnel, 4 qualitative filter papers, and an aspirator. The collected solid precalcined catalyst was rinsed with about 1 L of distilled water. Precautions were taken to prevent the filter cake from cracking. The pre-calcined catalyst was then washed with about 1 L of ethanol. The precalcined catalyst material was then dried overnight in an oven at approximately 90° C. The weight precalcined catalyst was 20.07 g.

Subsequently, the 20.07 g of precalcined catalyst was ground manually using a mortar and pestle. The whole sample of precalcined catalyst was placed in a 400 mL beaker and calcined in a muffle furnace under the following conditions: ramp to 280° C. over 30 minutes, hold for 30 minutes at 280° C., ramp to 400° C. over 30 minutes, hold for 6 hours at 400° C., off. The catalyst was calcined and cooled to room temperature, yielding about 19.02 g of Catalyst 1.6.

Catalyst 1.6 was analyzed by EDS as per the general procedure SEM-EDS. Results are presented in Table 2.

Figure 6:
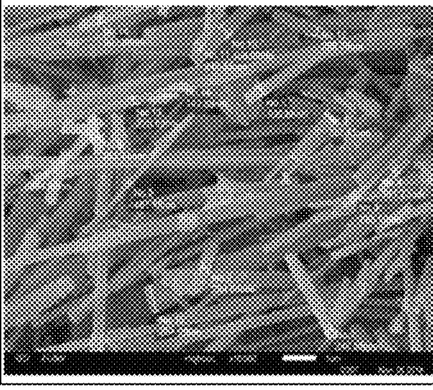
FIG. 6 shows the SEM images of Catalysts/Catalyst Materials 1.6.
Figure 6:
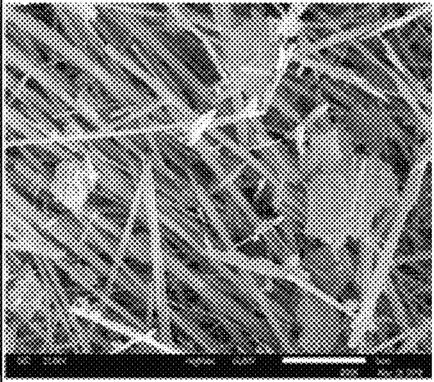

Catalyst 1.6 was submitted for SEM imaging. The results are presented in FIG. 6.

Powder XRD data was collected as per General Procedure XRD above. The plot for this catalyst is available in FIG. 1. The raw data PXRD plot was used in establishing the range of the peak intensities presented in Table 3.

PSD analysis results are presented in Table 4.

Bulk density measurements for Catalyst 1.6 are presented in Table 6.

Catalyst 1.6 was submitted for MRU testing. The results are presented in Table 7

ICP-MS Analysis of Catalysts 1.4 and 1.5.

The ICP-MS results for Catalysts 1.2, 1.4 and 1.5 are presented in Table 1.

TABLE 1

| | Measured Concentration (ppm) | | |
|---|---|---|---|
| Sample | Mo | V | Metal Molar Ratios |
| Catalyst 1.4 | 514700 | 109500 | $Mo_1V_{0.40}$ |
| Catalyst 1.5 | 657800 | 113000 | $Mo_1V_{0.32}$ |

EDS Analysis of Catalysts 1.2 and 1.4-1.6

The results for the EDS analysis of Catalyst 1.2 and 1.4-1.6 are presented in Table 2.

TABLE 2

| | Elemental Mass % | | |
|---|---|---|---|
| Sample | Mo | V | Metal Molar Ratios |
| Catalyst 1.2 | 52.01 | 12.06 | $Mo_1V_{0.44}$ |
| Catalyst 1.6 | 50.34 | 12.70 | $Mo_1V_{0.48}$ |
| Catalyst 1.4 | 52.13 | 11.37 | $Mo_1V_{0.41}$ |
| Catalyst 1.5 | 51.35 | 11.49 | $Mo_1V_{0.42}$ |

PXRD Analysis of Catalyst 1.4

Figure 2:
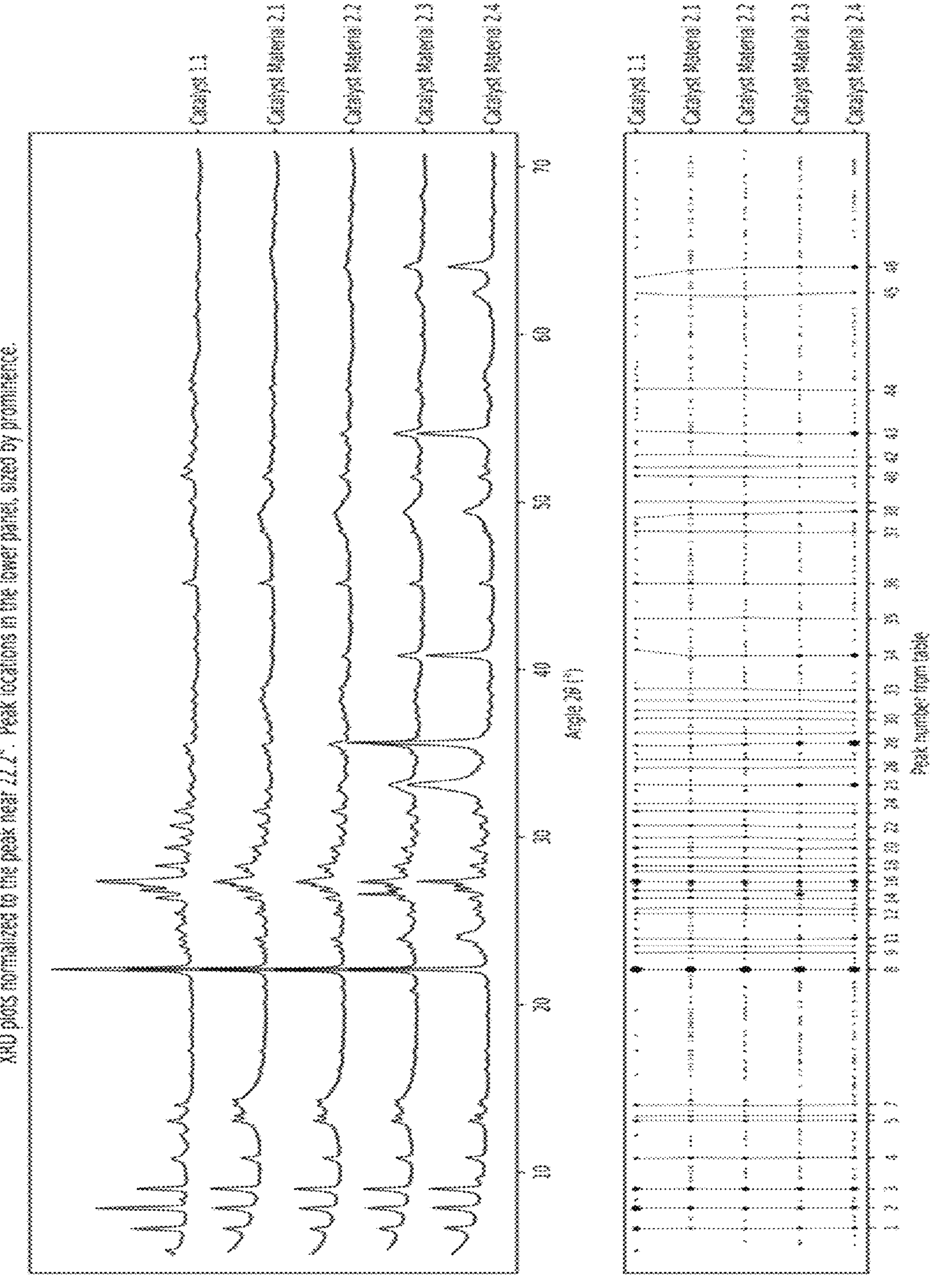
FIG. 2 shows the overlaid XRD plots of Catalyst 1.1 and Catalyst Materials 2.1-2.4.

Reflection angles and corresponding maximum and minimum relative peak intensity (relative to 22.2° 2θ) for Catalysts 1.1, and 1.4-1.6 are presented in Table 3. FIG. 1 presents the plot correlating to peak numbers for Catalysts 1.1, and 1.4-1.6.

TABLE 3

| Peak Number | Min Angle | Max Angle | Min Intensity | Max Intensity |
|---|---|---|---|---|
| 1 | 6.648 | 6.692 | 39.4% | 98.6% |
| 2 | 7.858 | 7.902 | 52.2% | 133.1% |
| 3 | 9.024 | 9.068 | 47.9% | 73.4% |
| 4 | 10.828 | 10.894 | 26.3% | 42.1% |
| 5 | 13.072 | 13.094 | 32.6% | 43.1% |
| 6 | 13.358 | 13.402 | 27.5% | 33.7% |
| 7 | 14.018 | 14.062 | 23.9% | 45.0% |
| 8 | 22.114 | 22.158 | 100.0% | 100.0% |
| 9 | 23.104 | 23.170 | 19.9% | 29.5% |
| 10 | 23.522 | 23.544 | 22.2% | 33.5% |
| 11 | 23.940 | 23.962 | 24.1% | 36.8% |
| 12 | 25.040 | 25.128 | 19.4% | 34.2% |
| 13 | 25.436 | 25.458 | 26.0% | 42.6% |
| 14 | 25.744 | 25.832 | 21.8% | 31.7% |
| 15 | 26.360 | 26.382 | 31.9% | 54.2% |
| 16 | 26.822 | 26.866 | 36.7% | 85.1% |
| 17 | 27.350 | 27.372 | 52.3% | 136.1% |
| 18 | 27.966 | 27.988 | 23.3% | 33.3% |
| 19 | 28.296 | 28.340 | 30.3% | 65.6% |
| 20 | 28.780 | 28.802 | 20.9% | 31.1% |
| 21 | 29.374 | 29.396 | 26.9% | 52.1% |
| 22 | 29.968 | 30.034 | 21.1% | 35.3% |
| 23 | 30.694 | 30.760 | 24.3% | 47.9% |
| 24 | 31.508 | 31.574 | 28.1% | 40.1% |
| 25 | 31.992 | 32.036 | 20.7% | 34.0% |
| 26 | 32.762 | 32.784 | 20.6% | 29.4% |
| 27 | 34.170 | 34.214 | 19.3% | 32.1% |
| 28 | 34.676 | 34.698 | 18.6% | 27.6% |
| 29 | 35.468 | 35.512 | 22.7% | 32.2% |
| 30 | 36.238 | 36.282 | 18.7% | 27.1% |
| 31 | 37.096 | 37.118 | 18.5% | 27.4% |
| 32 | 37.558 | 37.580 | 17.4% | 26.3% |
| 33 | 38.174 | 38.240 | 17.9% | 27.1% |
| 34 | 38.834 | 38.878 | 19.1% | 29.6% |
| 35 | 40.858 | 40.946 | 16.1% | 25.2% |
| 36 | 41.914 | 41.936 | 16.4% | 26.7% |
| 37 | 43.058 | 43.102 | 17.1% | 28.1% |
| 38 | 45.148 | 45.170 | 23.6% | 31.2% |
| 39 | 47.986 | 48.030 | 17.5% | 28.4% |

TABLE 3-continued

| Peak Number | Min Angle | Max Angle | Min Intensity | Max Intensity |
|---|---|---|---|---|
| 40 | 49.064 | 49.086 | 18.7% | 27.8% |
| 41 | 50.032 | 50.076 | 18.5% | 32.0% |
| 42 | 51.088 | 51.132 | 17.0% | 25.9% |
| 43 | 51.550 | 51.572 | 22.8% | 39.5% |
| 44 | 52.078 | 52.144 | 19.5% | 37.6% |
| 45 | 52.738 | 52.804 | 18.7% | 30.9% |

PSD Analysis of Catalysts 1.2 and Catalyst 1.6

Statistical data from the PSD of Catalysts 1.2 and 1.6 is presented in Table 4.

TABLE 4

| Sample | Catalyst 1.2 | Catalyst 1.6 |
|---|---|---|
| Maximum | 66.21 | 50.58 |
| Minimum | 0.47 | 0.19 |
| Mean | 8.54 | 9.68 |
| Median | 6.79 | 6.22 |
| Mode | 5.38-6.86 | 8.75-11.16 |
| Range | 65.74 | 50.39 |
| Skewness | 2.70 | 1.52 |
| Kurtosis | 12.12 | 2.19 |
| Standard Deviation | 6.90 | 9.46 |
| D10 | 2.55 | 1.33 |
| D25 (Quartile 1) | 4.18 | 2.64 |
| D50 | 6.79 | 6.22 |
| D75 (Quartile 3) | 10.33 | 13.58 |
| D90 | 15.92 | 23.62 |

BET Analysis of Catalysts 1.4 and 1.5

The results of nitrogen gas adsorption analysis for pore volume and BET surface area analysis for Catalyst 1.4 and Catalyst 1.5 are presented in Table 5.

TABLE 5

| Sample | BET Surface Area ($m^2/g$) | Pore Volume ($cm^3/g$) |
|---|---|---|
| Catalyst 1.4 | 8.3 | 0.02 |
| Catalyst 1.5 | 13.0 | 0.04 |

Bulk Density Measurements of Catalysts 1.2 and 1.6

Bulk density measurements of Catalysts 1.2 and 1.6 are presented in Table 6.

TABLE 6

| Sample | Measurements (g/mL) | Average (g/mL) |
|---|---|---|
| Catalyst 1.2 | 0.1099 | 0.1128 |
| | 0.1134 | |
| | 0.1152 | |
| Catalyst 1.6 | 0.1960 | 0.1944 |
| | 0.1949 | |
| | 0.1922 | |

Activity and Selectivity for Catalysts 1.1 and 1.4-1.6.

The MRU results for Catalysts 1.1 and 1.4-1.6 are presented in Table 7.

TABLE 7

| Sample | 35 mol. % Ethane Conversion Temperature (° C.) | Selectivity to Ethylene (mol. %) | MRU Loading Method |
|---|---|---|---|
| Catalyst 1.1 | 339 | 79 | Method 1 |
| Catalyst 1.4 | 348 | 80 | Method 1 |

TABLE 7-continued

| Sample | 35 mol. % Ethane Conversion Temperature (° C.) | Selectivity to Ethylene (mol. %) | MRU Loading Method |
|---|---|---|---|
| Catalyst 1.5 | 332 | 82 | Method 1 |
| Catalyst 1.6 | 338 | 81 | Method 1 |

Synthesis of Catalyst Materials 2.1-2.4

Example 6: Synthesis of Catalyst Material 2.1

Catalyst 1.2 (2.1 g) was placed in a 100 mL beaker. CATAPAL® B (Sasol) (4.9 g) and distilled water (approx. 25 mL) were then added to the beaker. The reaction mixture was then stirred using an electronic overhead stirrer equipped with Teflon blade agitator. The beaker was then placed in a 100° C. oil bath and the reaction mixture was stirred at approximately 80 rpm for 1 hour. The beaker was then placed in an oven (approx. 90° C.) and allowed to dry for about 2 days. Subsequently, the material was taken out of the oven and broken up with a spatula and placed in a muffle furnace. The material was then calcined to yield Catalyst Material 2.1a (6.32 g) using the program: ramp to 350° C. over 1 hour, hold for 2.5 hours at 350° C., off.

Catalyst 1.2 (3.0 g) was placed in a 100 mL beaker. CATAPAL® B (Sasol) (7.0 g) and distilled water (approx. 35 mL) were then added to the beaker. The reaction mixture was then stirred using an electronic overhead stirrer equipped with Teflon blade agitator. The beaker was then placed in a 100° C. oil bath and the reaction mixture was stirred at approximately 80 rpm for 1.5 hours during which it took on a paste-like consistency. The beaker was then placed in an oven (approx. 90° C.) and allowed to dry overnight. Subsequently, the material was taken out of the oven and broken up with a spatula and placed in a muffle furnace at 350° C. for 3 hours yielding Catalyst Material 2.1b (9.08 g).

Catalyst Materials 2.1a and 2.1b were combined to yield Catalyst Material 2.1 (15.40 g).

Catalyst Material 2.1 was analyzed by EDS as per the general procedure SEM-EDS. Results are presented in Table 9.

Catalyst Material 2.1 was submitted for SEM imaging. The results are presented in FIG. 7.

Powder XRD data was collected as per General Procedure XRD above. The plot for this catalyst is available in FIG. 2. The raw data PXRD plot was used in establishing the range of the peak intensities presented in Table 10.

PSD analysis results are presented in Table 11.

Catalyst Material 2.1 was submitted for MRU testing. The results are presented in Table 12 and Table 13.

Example 7: Synthesis of Catalyst Material 2.2

Catalyst 1.2 (2.1 g) was placed in a 100 mL beaker. CATAPAL® B (Sasol) (4.2 g), goethite (SIGMA-ALDRICH®) (0.7 g), and distilled water (approx. 25 mL) were then added to the beaker. The reaction mixture was then stirred using an electric overhead stirrer equipped with Teflon blade agitator. The beaker was then placed in a 100° C. oil bath and the reaction mixture was stirred at approximately 80 rpm for 1 hour during which it took on a paste-like consistency. The beaker was then placed in an oven (approx. 90° C.) and allowed to dry for about 2 days. Subsequently, the material was taken out of the oven and broken up with a spatula and placed in a muffle furnace. The material was then calcined to yield Catalyst Material 2.2a (6.32 g) using the program: ramp to 350° C. over 1 hour, hold for 2.5 hours at 350° C., off.

Catalyst 1.2 (3.0 g) was placed in a 100 mL beaker. CATAPAL® B (Sasol) (6.0 g), goethite (SIGMA-ALDRICH®) (1.0 g), and distilled water (approx. 35 mL) were then added to the beaker. The reaction mixture was then stirred using an electric overhead stirrer equipped with Teflon blade agitator. The beaker was then placed in a 100° C. oil bath and the reaction mixture was stirred at approximately 80 rpm for 1.5 hours during which it took on a paste-like consistency. The beaker was then placed in an oven (approx. 90° C.) and allowed to dry overnight. Subsequently, the material was taken out of the oven and broken up with a spatula and placed in a muffle furnace at 350° C. for 3 hours. To yield Catalyst Material 2.2b.

Catalyst Materials 2.2a and 2.2b were combined to yield Catalyst Material 2.2 (9.08 g).

Catalyst Material 2.2 was analyzed using the general ICP-MS procedure described herein using ICP digestion method 3. The ICP-MS results for Catalyst material 2.2 are presented in Table 8.

Catalyst Material 2.2 was analyzed by EDS as per the general procedure SEM-EDS. Results are presented in Table 9.

Catalyst Material 2.2 was submitted for SEM imaging. The results are presented in FIG. 7.

Powder XRD data was collected as per General Procedure XRD above. The plot for this catalyst is available in FIG. 2. The raw data PXRD plot was used in establishing the range of the peak intensities presented in Table 10.

PSD analysis results are presented in Table 11.

Catalyst Material 2.2 was submitted for MRU testing. The results are presented in Table 12 and Table 13.

Example 7: Synthesis of Catalyst Material 2.3

Catalyst 1.2 (2.1 g) was placed in a 100 mL beaker. CATAPAL® B (Sasol) (2.8 g), goethite (2.1 g), and distilled water (approx. 25 mL) were then added to the beaker. The reaction mixture was then stirred manually. The beaker was then placed in a 100° C. oil bath and the reaction mixture was stirred at approximately 80 rpm for 1 hour during which it took on a paste-like consistency. The beaker was then placed in an oven (approx. 90° C.) and allowed to dry overnight. Subsequently, the material was taken out of the oven and broken up with a spatula and placed in a muffle furnace. The material was then calcined to yield Catalyst Material 2.3 (6.52 g) using the program: ramp to 350° C. over 1 hour, hold for 2.5 hours at 350° C., off.

Catalyst Material 2.3 was analyzed by ICP-MS using the general ICP-MS procedure described herein using ICP digestion method 3. The ICP-MS results for Catalyst Material 2.3 are presented in Table 8.

Catalyst Material 2.3 was analyzed by EDS as per the general procedure SEM-EDS. Results are presented in Table 9.

Catalyst Material 2.3 was submitted for SEM imaging. The results are presented in FIG. 7.

Powder XRD data was collected as per General Procedure XRD above. The plot for this catalyst is available in FIG. 2. The raw data PXRD plot was used in establishing the range of the peak intensities presented in Table 10.

PSD analysis results are presented in Table 11.

Catalyst Material 2.3 was then submitted for MRU testing. The results are presented in Table 12 and Table 13.

Example 8: Synthesis of Catalyst Material 2.4

Catalyst 1.2 (2.1 g) was placed in a 100 mL beaker. Goethite (SIGMA-ALDRICH®) (4.9 g), and distilled water (approx. 25 mL) were then added to the beaker. The reaction mixture was then stirred manually. The beaker was then placed in a 100° C. oil bath and the reaction mixture was stirred at approximately 80 rpm for 0.75 hours during which it took on a paste-like consistency. The beaker was then placed in an oven (approx. 90° C.) and allowed to dry overnight. Subsequently, the material was taken out of the oven and broken up with a spatula and placed in a muffle furnace. The material was then calcined to yield Catalyst Material 2.4 (6.52 g) using the program: ramp to 350° C. over 1 hour, hold for 2.5 hours at 350° C., off.

Catalyst Material 2.4 was analyzed by ICP-MS using the general ICP-MS procedure described herein using ICP digestion method 3. The ICP-MS results for Catalyst material 2.4 are presented in Table 8.

Catalyst Material 2.4 was analyzed by EDS as per the general procedure SEM-EDS. Results are presented in Table 9.

Catalyst Material 2.4 was submitted for SEM imaging. The results are presented in FIG. 7.

Powder XRD data was collected as per General Procedure XRD above. The plot for this catalyst is available in FIG. 2. The raw data PXRD plot was used in establishing the range of the peak intensities presented in Table 10.

PSD analysis results are presented in Table 11.

Catalyst Material 2.4 was then submitted for MRU testing. The results are presented in Table 12 and Table 13.

ICP-MS Analysis of Catalyst Materials 2.2-2.4

The ICP-MS results for Catalyst Materials 2.2-2.4 are presented in Table 8.

TABLE 8

| | Starting Material Ratios (wt. %) | | | Measured Concentration (ppm) | | | | |
|---|---|---|---|---|---|---|---|---|
| | Catalyst | α- | γ- | | | | | |
| Sample | 1.2 | FeOOH | AlO(OH) | Mo | V | Fe | Al | Metal Molar Ratio |
| Catalyst Material 2.2 | 30 | 10 | 60 | 134200 | 27850 | 47240 | 188100 | $Mo_1V_{0.39}Fe_{0.6}Al_{4.98}$ |
| Catalyst Material 2.3 | 30 | 30 | 40 | 179100 | 37050 | 191200 | 152700 | $Mo_1V_{0.39}Fe_{1.83}Al_{3.03}$ |
| Catalyst Material 2.4 | 30 | 70 | 0 | 216100 | 44360 | 564600 | — | $Mo_1V_{0.39}Fe_{4.49}$ |

EDS Analysis of Catalysts 1.2 and Catalyst Materials 2.1-2.4.

The EDS analysis of Catalyst 1.2 and Catalyst Materials 2.1-2.4 are presented in Table 9.

TABLE 9

| | Starting Material Ratios (wt. %) | | | Elemental Mass % | | | | |
|---|---|---|---|---|---|---|---|---|
| | Catalyst | α- | γ- | | | | | |
| Sample | 1.2 | FeOOH | AlO(OH) | Mo | V | Fe | Al | Metal Molar Ratio |
| Catalyst 1.2 | 100 | 0 | 0 | 52.01 | 12.06 | 0.13 | — | $Mo_1V_{0.44}$ |
| Catalyst Material 2.1 | 30 | 0 | 70 | 23.60 | 5.35 | — | 21.56 | $Mo_1V_{0.43}Al_{3.25}$ |
| Catalyst Material 2.2 | 30 | 10 | 60 | 23.91 | 5.32 | 9.97 | 17.15 | $Mo_1V_{0.42}Fe_{0.72}Al_{2.55}$ |
| Catalyst Material 2.3 | 30 | 30 | 40 | 20.00 | 4.32 | 24.60 | 9.46 | $Mo_1V_{0.41}Fe_{2.11}Al_{1.68}$ |
| Catalyst Material 2.4 | 30 | 70 | 0 | 15.10 | 3.30 | 46.36 | — | $Mo_1V_{0.41}Fe_{5.27}$ |

PXRD Analysis of Catalysts 1.1 and Catalyst Materials 2.1-2.4.

Reflection angles and corresponding maximum and minimum relative peak intensity (relative to 22.2° 2θ) for Catalysts 1.1 and Catalyst Materials 2.1-2.4 are presented in Table 10. See FIG. 2 for plot correlating to peak numbers.

TABLE 10

| Peak Number | Min Angle | Max Angle | Min Intensity | Max Intensity |
|---|---|---|---|---|
| 1 | 6.648 | 6.692 | 41.1% | 56.7% |
| 2 | 7.858 | 7.902 | 46.7% | 75.9% |
| 3 | 9.024 | 9.046 | 49.7% | 56.1% |
| 4 | 10.828 | 10.894 | 33.3% | 37.6% |
| 5 | 13.072 | 13.094 | 35.0% | 42.6% |
| 6 | 13.358 | 13.424 | 30.3% | 41.0% |
| 7 | 13.996 | 14.062 | 29.5% | 41.6% |
| 8 | 22.114 | 22.114 | 100.0% | 100.0% |
| 9 | 23.104 | 23.148 | 24.8% | 29.0% |
| 10 | 23.5 | 23.522 | 26.9% | 32.2% |
| 11 | 23.918 | 23.962 | 29.8% | 41.7% |
| 12 | 25.392 | 25.458 | 28.2% | 33.6% |
| 13 | 25.722 | 25.788 | 26.0% | 32.2% |
| 14 | 26.316 | 26.382 | 32.8% | 43.5% |
| 15 | 26.822 | 26.822 | 35.7% | 52.0% |
| 16 | 27.328 | 27.372 | 49.0% | 76.0% |
| 17 | 27.922 | 27.966 | 29.5% | 36.3% |
| 18 | 28.274 | 28.318 | 34.3% | 44.0% |
| 19 | 28.736 | 28.78 | 27.9% | 31.3% |
| 20 | 29.308 | 29.396 | 29.8% | 39.2% |
| 21 | 29.88 | 30.012 | 24.7% | 30.2% |
| 22 | 30.584 | 30.694 | 26.1% | 36.1% |
| 23 | 31.442 | 31.552 | 28.9% | 33.4% |
| 24 | 31.992 | 32.014 | 23.7% | 31.6% |
| 25 | 33.07 | 33.158 | 22.4% | 68.5% |
| 26 | 34.148 | 34.214 | 22.3% | 30.7% |
| 27 | 34.632 | 34.676 | 22.2% | 28.5% |
| 28 | 35.468 | 35.644 | 26.5% | 101.4% |
| 29 | 36.194 | 36.238 | 22.4% | 27.7% |
| 30 | 37.03 | 37.118 | 22.9% | 25.4% |
| 31 | 37.47 | 37.58 | 23.5% | 25.6% |
| 32 | 38.064 | 38.196 | 24.1% | 27.7% |
| 33 | 38.768 | 38.856 | 24.0% | 26.6% |
| 34 | 40.836 | 41.21 | 21.4% | 58.0% |
| 35 | 43.036 | 43.124 | 19.9% | 24.5% |
| 36 | 45.104 | 45.148 | 26.5% | 29.7% |
| 37 | 48.206 | 48.272 | 25.1% | 27.2% |
| 38 | 49.064 | 49.46 | 24.8% | 37.9% |
| 39 | 49.988 | 50.054 | 23.4% | 28.7% |
| 40 | 51.462 | 51.572 | 24.3% | 30.7% |
| 41 | 52.078 | 52.144 | 21.4% | 28.4% |
| 42 | 52.672 | 52.848 | 20.8% | 25.8% |
| 43 | 54.058 | 54.234 | 21.3% | 63.5% |
| 44 | 56.676 | 56.808 | 21.2% | 27.3% |
| 45 | 62.308 | 62.506 | 19.7% | 32.8% |
| 46 | 63.386 | 64.024 | 20.8% | 46.6% |

PSD Analysis of Catalysts 1.2, and Catalyst Materials 2.1-2.4

The PSD analysis of Catalyst 1.2, and Catalyst Materials 2.1-2.4 are presented in Table 11.

TABLE 11

| Sample | Catalyst 1.1 & Catalyst 1.2 | Catalyst Material 2.1 | Catalyst Material 2.2 | Catalyst Material 2.3 | Catalyst Material 2.4 |
|---|---|---|---|---|---|
| Maximum | 66.21 | 434.00 | 572.90 | 449.20 | 741.20 |
| Minimum | 0.47 | 0.05 | 0.03 | 0.03 | 0.13 |
| Mean | 8.54 | 31.40 | 11.20 | 22.45 | 47.08 |
| Median | 6.79 | 3.36 | 0.95 | 0.75 | 18.33 |
| Mode | 5.38-6.86 | 2.03-2.59 | 0.60-0.77 | 0.60-0.77 | 0.37-0.47 |
| Range | 65.74 | 433.95 | 572.87 | 449.17 | 741.07 |
| Skewness | 2.70 | 3.04 | 9.82 | 4.17 | 3.21 |
| Kurtosis | 12.12 | 10.34 | 157.39 | 23.96 | 17.91 |
| Standard Deviation | 6.90 | 64.91 | 30.97 | 47.82 | 73.42 |
| D10 | 2.55 | 0.53 | 0.17 | 0.16 | — |
| D25 (Quartile 1) | 4.18 | 1.31 | 0.45 | 0.35 | 0.48 |
| D50 | 6.79 | 3.36 | 0.95 | 0.75 | — |
| D75 (Quartile 3) | 10.33 | 18.24 | 6.83 | 30.01 | 68.13 |
| D90 | 15.92 | 99.10 | 37.30 | 68.67 | — |

Activity and Selectivity for Catalysts 1.1 and Catalyst Materials 2.1-2.4

The MRU results for Catalysts 1.1 and Catalyst Materials 2.1-2.4 are presented in Tables 12 and 13. These catalysts were allowed to run on the MRU for 2-5 days. Table 12 summarizes the catalyst performance based on the MRU loading method and Table 13 summarizes the catalyst composition differences with catalyst performance. The ethane conversion and selectivity to ethylene have been calculated as described above at a specific temperature (348±2° C.).

TABLE 12

| Sample | Ethane Conversion at 348 ± 2° C. (mol. %) | Selectivity to Ethylene (mol. %) | MRU Loading Method | Acetic Acid Concentration in Collected Condensate (range) (wt. %) |
|---|---|---|---|---|
| Catalyst 1.1 | 35.6 | 83.2 | Method 1 | 15.8-15.9 |
| Catalyst Material 2.1 | 30.3-30.4 | 83.3-84.1 | Method 2 | 11.8-13.5 |
| Catalyst Material 2.2 | 28.3 | 82.7-82.9 | Method 2 | 10.6-11.9 |
| Catalyst Material 2.3 | 28.3-30.8 | 79.8-81.9 | Method 2 | 9.2-11.0 |
| Catalyst Material 2.4 | 26.8-28.9 | 80.6-81.8 | Method 2 | 8.3 |

TABLE 13

| Sample | Molar Formula | Starting Material Ratios (wt. %) Catalyst | α-FeOOH | γ-AlO(OH) | Length of Run (day) | Temp of Run (° C.) | Ethane Conversion at End of Run (mol %) | Selectivity to Ethylene at End of Run (mol %) | Acetic Acid Conc. in Collected Condensate (range) (wt. %) |
|---|---|---|---|---|---|---|---|---|---|
| Catalyst 1.1 | $Mo_1V_{0.44}$* | 100 | 0 | 0 | 4 | 348 | 35.6 | 83.2 | 15.8-15.9 |
| Catalyst Material 2.1 | $Mo_1V_{0.43}Fe_{0.01}Al_{3.25}$* | 30 | 0 | 70 | 4 | 347 | 30.3-30.4 | 83.3-84.1 | 11.8-13.5 |
| Catalyst Material 2.2 | $Mo_1V_{0.39}Fe_{0.6}Al_{4.98}$‡ | 30 | 10 | 60 | 2 | 347 | 28.3 | 82.7-82.9 | 10.6-11.9 |
| Catalyst Material 2.3 | $Mo_1V_{0.39}Fe_{1.83}Al_{3.03}$‡ | 30 | 30 | 40 | 5 | 350 | 28.8-30.8 | 79.8-81.9 | 9.2-11.0 |

TABLE 13-continued

| Sample | Molar Formula | Starting Material Ratios (wt. %) Catalyst | α-FeOOH | γ-AlO(OH) | Length of Run (day) | Temp of Run (° C.) | Ethane Conversion at End of Run (mol %) | Selectivity to Ethylene at End of Run (mol %) | Acetic Acid Conc. in Collected Condensate (range) (wt. %) |
|---|---|---|---|---|---|---|---|---|---|
| Catalyst Material 2.4 | $Mo_1V_{0.39}Fe_{4.49}$‡ | 30 | 70 | 0 | 3 | 348 | 26.8-28.9 | 80.6-81.8 | 8.3 |

*molar formula from EDS measurement. Catalyst 1.1 composition is assumed to be the same as catalyst 1.2. The reported molar formula is for catalyst 1.2.
‡molar formula from ICP-MS Synthesis of Catalysts 3.1-3.18

Example 9: Synthesis of Catalyst 3.1

$(NH_4)_6Mo_7O_{24}\cdot4H_2O$ (SIGMA-ALDRICH®) (13.26 g) was weighed in a 500 mL round bottomed flask. The white solid was dissolved in 180 mL of distilled water with the aid of a 60° C. warm water bath and stirring to create a clear, colorless solution. $VOSO_4\cdot3.46H_2O$ (SIGMA-ALDRICH®) (4.22 g) was weighed into a 250 mL beaker. The blue solid was dissolved in 180 mL of distilled water with the aid of a 60° C. warm water bath and stirring to create a clear, blue solution. The blue vanadium solution was added all-at-once to the colorless molybdenum solution to instantly produce a black solution. The resulting black solution was stirred for 30 minutes at 60° C. The pH of the solution was measured with a pH probe to be 2.70 before addition of surfactant.

After 30 minutes, sodium dodecyl sulfate surfactant (SIGMA-ALDRICH®) (SDS; 4.05 g) was added as a powder to the black molybdenum-vanadium solution to produce a purple slurry with some emulsion present. The purple-emulsified slurry was stirred for 30 minutes at 60° C. The pH of the SDS containing slurry was measured to be 2.70.

After 30 minutes, the purple slurry was added to a glass liner and the glass liner was added to a 600 mL PARR high pressure reactor. The PARR reactor was sealed and purged with 15 psig nitrogen gas and vacuum sequence ten times, then left under 15 psig nitrogen. The PARR reactor was placed into an oven and the oven was heated to 230° C. The reaction proceeded at 230° C. for 24 hours before being turned off and allowed to cool to room temperature.

Once cooled, the reactor was vented, opened, and the resulting spongy-slurry was filtered. The filtering was done using a Buchner funnel and 4 layers of qualitative filter paper. The mother liquor was blue. The solids were washed with water (0.5 L) until the filtrate ran clear. The washed solids were dark purple in color with some large dark brown aggregates and brown oil present. The brown aggregates were removed, and the remaining purple spongy solids were washed with denatured ethanol (0.5 L) producing a yellow filtrate. The solids were dried at 90° C. overnight and the next morning the dry solids were weighed: 5.68 g.

The precalcined catalyst was pressed with a spatula into a quartz boat. The quartz boat containing the precalcined catalyst was loaded into a quartz tube, which was placed into a split tube furnace. The quartz tube was purged with bulk nitrogen for 8 hours at 400 sccm, before the nitrogen feed was fed through an oxygen scrubbing bed to further purify the nitrogen to less than 4 ppm oxygen. This ultra-high purity (UHP) nitrogen was purged through the quartz tube overnight at 400 sccm for 18 hours. Next, the furnace was turned on and heated to 400° C. to calcine the catalyst. The heating program for the furnace was: 4 hours ramp from room temperature to 400° C., dwell at 400° C. for 2 hours and then cool to ambient temperature naturally.

The calcined catalyst, Catalyst 3.1, weighed 5.26 g (93% calcination yield). There was no yellow oil observed inside the quartz tube indicating that the SDS oil degradation product was sufficiently removed with ethanol wash for the nitrogen calcination step.

Catalyst 3.1 was then submitted for MRU testing. The results are presented in Table 20.

Example 10: Synthesis of Catalyst 3.2

$(NH_4)_6Mo_7O_{24}$. $4H_2O$ (SIGMA-ALDRICH®) (13.27 g) and distilled water (120 mL) were added to a 500 mL round bottom flask. $VOSO_4\cdot3.46H_2O$ (SIGMA-ALDRICH®) (4.25 g) and distilled water (120 mL) were placed in a 250 mL beaker. The blue vanadium solution was then slowly poured into the clear and colorless molybdenum solution. Subsequently, SDS (SIGMA-ALDRICH®) (4.09 g) was added to the reaction mixture, which was then allowed stir for 30 min at 60° C.

Next, the contents were transferred to a 600 mL glass liner, which was then transferred into a 600 mL PARR reactor and sealed. The PARR reactor was evacuated and backfilled ten times with 15 psi of nitrogen. Subsequently, the PARR reactor was left under 15 psi of nitrogen and heated in an oven at 230° C. for 20 hours after which it was cooled down to room temperature. The contents of the glass liner were filtered through a Buchner funnel using Whatman #4 filter paper. The filtered solid was then rinsed with 500 mL of distilled water and 500 mL of ethanol and then dried in a 90° C. oven for 18 hours.

The precalcined catalyst (4.90 g) was then calcined using the nitrogen calcination described herein to yield Catalyst 3.2 (4.50 g).

Example 11: Synthesis of Catalyst 3.3

$(NH_4)_6Mo_7O_{24}$. $4H_2O$ (SIGMA-ALDRICH®) (13.26 g) and distilled water (180 mL) were added to a 500 mL round bottom flask. The mixture was stirred at 60° C. for 30 minutes using a warm water bath. $VOSO_4\cdot3.46H_2O$ (SIGMA-ALDRICH®) (4.22 g) and distilled water (180 mL) were placed in a 250 mL beaker. The mixture was stirred at 60° C. for 30 minutes using a warm water bath. The blue vanadium solution was then slowly poured into the clear and colorless molybdenum solution forming a dark purple solution. Subsequently, SDS (SIGMA-ALDRICH®) (4.07 g) was added to the reaction mixture, which was then allowed stir for 30 minutes at 60° C.

The contents were then transferred to a 600 mL glass liner, which was then transferred into a 600 mL PARR reactor and sealed. The PARR reactor was evacuated and backfilled ten times with 15 psi of nitrogen. Subsequently, the PARR reactor was left under 15 psi of nitrogen and heated in an oven at 230° C. for 20 hours after which it was cooled down to room temperature. The contents of the glass liner were then filtered through a Buchner funnel using Whatman #4 filter paper. The filtered solid was rinsed with 500 mL of distilled water and 500 mL of ethanol and then dried in a 90° C. oven for 18 hours to yield Catalyst 3.3.

Example 12: Synthesis of Catalyst 3.4

$(NH_4)_6Mo_7O_{24}$. $4H_2O$ (SIGMA-ALDRICH®) (13.26 g) was added to a 500 mL RBF with a magnetic stir bar. Subsequently, 180 mL of distilled water was added and the $(NH_4)_6Mo_7O_{24}{\cdot}4H_2O$ was dissolved using a water bath at approximately 60° C. Next, $VOSO_4{\cdot}3.46H_2O$ (SIGMA-ALDRICH®) (4.22 g) was placed into a 250 mL beaker with a magnetic stir bar. Subsequently, approximately 180 mL distilled water was added and the $VOSO_4{\cdot}3.46H_2O$ was dissolved with the aid of water bath at approximately 60° C. Then, the vanadium solution was added to the round bottom flask containing the molybdenum solution while stirring at 60° C. Sodium dodecyl sulfate (SIGMA-ALDRICH®) (4.07 g) was then added to the round bottom flask containing the vanadium and molybdenum solution while stirring at 60° C. and the mixture was stirred for approximately 30 minutes at 60° C.

The solution was then transferred to a 600 mL glass liner and the round bottom flask was rinsed with distilled water and the rinse was transferred to the glass liner. The glass liner containing the dark purple solution was inserted into a 600 mL PARR reactor. The PARR reactor was sealed. Subsequently, the PARR reactor headspace was pumped and purged ten times with nitrogen. The headspace was left under approximately 15 psig nitrogen. The reactor was placed in an oven at approximately 230° C. for approximately 21 hours and then allowed to cool for approximately 2 hours. Subsequently, the PARR reactor was removed from the oven and allowed to cool for 18 hours.

The reaction mixture was filtered using a Buchner funnel, 4 qualitative filter papers, and an aspirator. The collected precalcined catalyst was washed with distilled water. The filtrate was initially a dark blue, and the precalcined catalyst was washed until the filtrate was clear. The precalcined catalyst was greyish in color. Then, the precalcined catalyst was washed with ethanol—the filtrate was a light blue at first but transitioned to clear in color as additional ethanol was used for rinsing the solids. The precalcined catalyst material was then dried overnight in an oven at approximately 90° C. Subsequently, the precalcined catalyst was ground manually using a mortar and pestle producing a light and fluffy precalcined catalyst.

Next, 4.95 g of the precalcined catalyst was loaded into two quartz boats and placed in a quartz tube. The quartz tube was placed into a split tube furnace. The quartz tube was then purged with bulk nitrogen at approximately 85 sccm (0.085 standard liter per minute (slpm)) for 6 hours and then the flow changed to purified nitrogen and the split tube was purged for 18 hours at a flow of 85 sccm.

Next, the temperature program for the split tube was set to: 4 hour ramp to 400° C., hold for 2 hours at 400° C.; reduced nitrogen flow to approximately to 30 sccm. After calcination, the catalyst was allowed to cool to room temperature and then taken out of the split tube, yielding Catalyst 3.4 (4.65 g).

Example 13: Synthesis of Catalyst 3.5

$(NH_4)_6Mo_7O_{24}{\cdot}4H_2O$ (SIGMA-ALDRICH®) (13.26 g) was added to a 500 mL RBF with a magnetic stir bar. Subsequently, 180 mL of distilled water was added and the $(NH_4)_6Mo_7O_{24}{\cdot}4H_2O$ was dissolved using a water bath at approximately 60° C. Next, $VOSO_4{\cdot}3.46H_2O$ (SIGMA-ALDRICH®) (4.22 g) was placed into a 250 mL beaker with a magnetic stir bar. Subsequently, approximately 180 mL distilled water was added and the $VOSO_4{\cdot}3.46H_2O$ was dissolved with the aid of water bath at 60° C. Then, the vanadium solution was added to the round bottom flask containing the molybdenum solution while stirring at 60° C. Sodium dodecyl sulfate (SIGMA-ALDRICH®) (4.07 g) was then added to the round bottom flask containing the vanadium and molybdenum solution while stirring at 60° C. and the mixture was stirred for approximately 30 minutes at 60° C.

The solution was then transferred to a 600 mL glass liner and the round bottom flask was rinsed with distilled water and the rinse was transferred to the glass liner. The glass liner containing the dark purple solution was inserted into a 600 mL PARR reactor. The PARR reactor was sealed. Subsequently, the PARR reactor headspace was pumped and purged six times with nitrogen. The headspace was left under approximately 15 psig nitrogen. The reactor was placed in an oven at approximately 230° C. for approximately 21.5 hours and then allowed to cool for approximately 2 hours. Subsequently, the PARR reactor was removed from the oven and allowed to cool overnight.

The reaction mixture was filtered using a Buchner funnel, 4 qualitative filter papers, and an aspirator. The collected precalcined catalyst was washed with distilled water. The filtrate was initially a dark blue, and the precalcined catalyst was washed until the filtrate was clear. The precalcined catalyst was greyish in color. Then, the precalcined catalyst was washed with ethanol—the filtrate was a light blue at first and changed to clear and colorless with the washes. The precalcined catalyst material was then dried for 18 hours in an oven at approximately 90° C. Subsequently, the precalcined catalyst was ground manually using a mortar and pestle producing a light and fluffy precalcined catalyst.

Next, 5.47 g of the precalcined catalyst was loaded into two quartz boats and placed in a quart tube. The quartz tube was placed into a split tube furnace. The quartz tube was then purged with bulk nitrogen at approximately 85 sccm for the remainder of the day and then the flow changed to purified nitrogen and the split tube was purged overnight at a flow of 85 sccm.

Next, the temperature program for the split tube was set to: 4 hour ramp to 400° C., hold for 2 hours at 400° C.; reduced nitrogen flow to approximately to 30 sccm. After calcination, the catalyst was allowed to cool to room temperature and then taken out of the split tube, yielding Catalyst 3.5 (4.97 g).

Example 14: Synthesis of Catalyst 3.6

$(NH_4)_6Mo_7O_{24}$. $4H_2O$ (SIGMA-ALDRICH®) (44.20 g) was added to a 2 L RBF with a magnetic stir bar. Subsequently, 600 mL of distilled water was added and the $(NH_4)_6Mo_7O_{24}{\cdot}4H_2O$ was dissolved using a 60° C. water bath. Next, $VOSO_4{\cdot}3.46H_2O$ (SIGMA-ALDRICH®) (14.07 g) was placed into a 1 L beaker with a magnetic stir bar. Subsequently, approximately 600 mL distilled water was added and the $VOSO_4 \cdot 3.46H_2O$ was dissolved with the aid of a 60° C. water bath. Then, the vanadium solution was added to the round bottom flask containing the molybdenum solution while stirring at 60° C. Sodium dodecyl sulfate (SIGMA-ALDRICH®) (13.57 g) was then added to the round bottom flask containing the vanadium and molybdenum solution while stirring at 60° C. and the mixture was stirred for approximately 30 minutes at 60° C.

After allowing to cool, the solution was then transferred to a 2 L glass liner and the round bottom flask was rinsed with distilled water and the rinse was transferred to the glass liner. The glass liner containing the purple solution was inserted into a 2 L PARR reactor. The head unit was sealed. Subsequently, the PARR reactor headspace was pumped and purged ten times with the combination of nitrogen and vacuum. The headspace was left under approximately 15 psig nitrogen. The reaction was stirred at approximately 150 rpm for about 26 hours at temperature from 230° C. to 247° C. (temperature controller was set to 247° C.; the internal temperature was about 238° C. after running overnight; the set point was then lowered to 239° C. and the internal temperature ranged from 230° C. to 231° C.). After heating, the reaction was allowed to cool overnight while stirring at 150 rpm.

The reaction mixture was then filtered using a Buchner funnel, filter paper, and an aspirator. Subsequently, the collected precalcined catalyst was washed with distilled water and ethanol. The precalcined catalyst was then dried in an oven at approximately 90° C. for 56 hours to yield 18.1 g of precalcined catalyst. Next, a portion of the precalcined catalyst was ground manually with a mortar and pestle.

The precalcined catalyst was then calcined using the general nitrogen calcination process described herein to yield Catalyst 3.6.

Catalyst 3.6 was then submitted for MRU testing. The results are presented in Table 20.

Example 15: Synthesis of Catalyst 3.7

$(NH_4)_6Mo_7O_{24} \cdot 4H_2O$ (SIGMA-ALDRICH®) (8.83 g) was weighed in a 500 mL round bottomed flask. The white solid was dissolved in 100 mL of distilled water with the aid of a 60° C. warm water bath and stirring to create a clear, colorless solution. $VOSO_4 \cdot 3.46H_2O$ (SIGMA-ALDRICH®) (2.81 g) was weighed into a 250 mL beaker. The blue solid was dissolved in 100 mL of distilled water with the aid of a 60° C. warm water bath and stirring to create a clear, blue solution. The blue vanadium solution was added all-at-once to the colorless molybdenum solution to instantly produce a black solution. To the black solution, 2.70 g of sodium dodecyl sulfate (SIGMA-ALDRICH®) surfactant was added as a powder to produce a purple slurry with some emulsion present. The purple-emulsified slurry was stirred for 30 minutes at 60° C. The purple slurry was removed from the 60° C. warm water bath and allowed to cool for 15 minutes.

The purple slurry was added to a glass liner and the glass liner was added to a 600 mL PARR high pressure reactor. The PARR reactor was sealed and purged with 15 psig nitrogen gas and vacuum sequence ten times, then left under 15 psig nitrogen. The PARR reactor was placed into an oven and the oven was heated to 230° C. The reaction proceeded at 230° C. for 20.5 hours before being turned off and allowed to cool to room temperature.

Once cooled, the reactor was vented, opened, and the resulting spongy-slurry was filtered. The filtering was done using a Buchner funnel and 4 layers of qualitative filter paper. The mother liquor was blue and the solids grey. The solids were washed with water until the filtrate ran clear. The solids were further washed with denatured ethanol. The solids were dried at 90° C. overnight and the next morning the dry solids were weighed: 2.46 g.

The precalcined catalyst was manually ground using a mortar and pestle and then loaded into a quartz boat. The quartz boat containing the precalcined catalyst was loaded into a quartz tube, which was placed into a split tube furnace. The quartz tube was purged with bulk nitrogen for 5 hours at 85 sccm, before the nitrogen feed was fed through an oxygen scrubbing bed to further purify the nitrogen to less than 4 ppm oxygen. This ultra-high purity (UHP) nitrogen was purged through the quartz tube for 18 hours at 85 sccm. Next, the UHP nitrogen feed was reduced from 85 sccm to 30 sccm and the furnace was turned on and heated to 400° C. to calcine the catalyst. The heating program for the furnace was: 4 hours ramp from room temperature to 400° C., dwell at 400° C. for 2 hours and then cool to ambient temperature naturally. Calcination yielded Catalyst 3.7.

Catalyst 3.7 was then submitted for ICP-MS analysis using the general ICP-MS procedure described herein using digestion method 2. The results are presented in Table 14.

Catalyst 3.7 was analyzed by EDS as per the general procedure SEM-EDS. The results are presented in Table 15.

Powder XRD data was collected as per General Procedure XRD above. The plot for this catalyst is available in FIG. 3. The raw data PXRD plot was used in establishing the range of the peak intensities presented in Table 16.

PSD analysis results are presented in Table 17.

Figure 10:
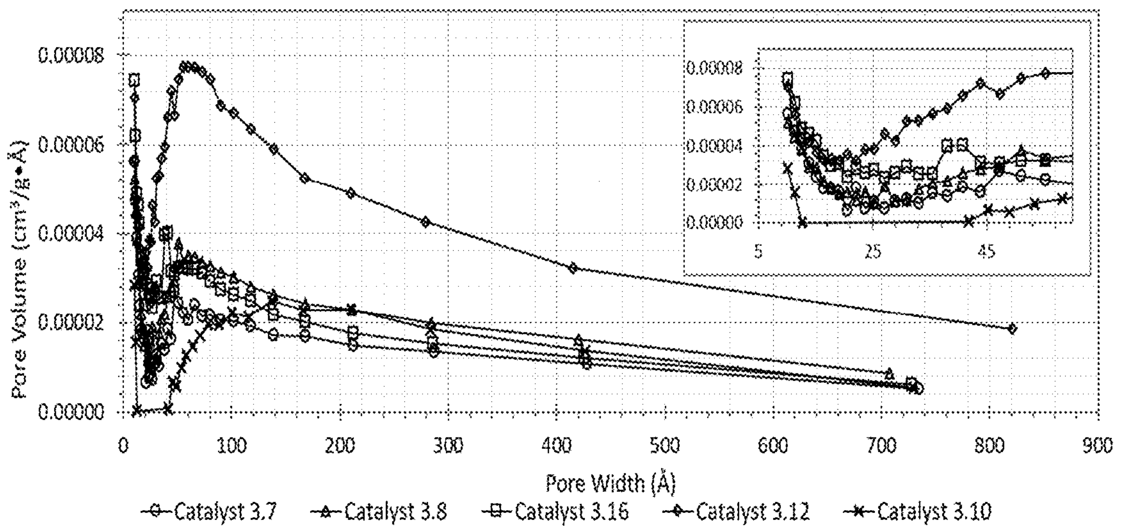
FIG. 10 shows the Barrett-Joyner-Halenda (BJH) plot for Catalysts 3.7-3.8, 3.10, 3.12 and 3.16.

Catalyst 3.7 was analyzed by nitrogen gas adsorption analysis for pore volume, BET surface area, and BJH pore size distributions analysis. Pore volume and BET surface area analysis results are presented in Table 18. BJH analysis results are presented in FIG. 10.

Catalyst 3.7 was then submitted for MRU testing. The results are presented in Table 20.

Example 16: Synthesis of Catalyst 3.8

$(NH_4)_6Mo_7O_{24} \cdot 4H_2O$ (SIGMA-ALDRICH®) (13.26 g) was weighed in a 500 mL round bottomed flask. The white solid was dissolved in 120 mL of distilled water with the aid of a 60° C. warm water bath and stirring to create a clear, colorless solution. $VOSO_4 \cdot 3.46H_2O$ (SIGMA-ALDRICH®) (4.28 g) was weighed into a 250 mL beaker. The blue solid was dissolved in 120 mL of distilled water with the aid of a 60° C. warm water bath and stirring to create a clear, blue solution. The blue vanadium solution was added all-at-once to the colorless molybdenum solution to instantly produce a black solution. To the black solution, 4.11 g of sodium dodecyl sulfate (SIGMA-ALDRICH®) surfactant was added as a powder to produce a purple slurry with some emulsion present. The purple-emulsified slurry was stirred for 30 minutes at 60° C.

The purple slurry was added to a glass liner and the glass liner was added to a 600 mL PARR high pressure reactor. The PARR reactor was sealed and purged with 15 psig nitrogen gas and vacuum sequence ten times, then left under 15 psig nitrogen. The PARR reactor was placed into an oven and the oven was heated to 230° C. The reaction proceeded at 230° C. for 24 hours before being turned off and allowed to cool to room temperature.

Once cooled, the reactor was vented, opened, and the resulting spongy-slurry was filtered. The filtering was done using a Buchner funnel and 4 layers of qualitative filter paper. The mother liquor was blue and the solids grey. The solids were washed with water until the filtrate ran clear. The solids were further washed with denatured ethanol until ran clear. The solids were dried at 90° C. overnight and the next morning the dry solids were weighed: 4.32 g.

The 4.32 g of precalcined catalyst were manually ground using a mortar and pestle and then loaded into a quartz boat. The quartz boat containing the precalcined catalyst was loaded into a quartz tube, which was placed into a split tube furnace. The quartz tube was purged with bulk nitrogen for 5 hours at 85 sccm, before the nitrogen feed was fed through an oxygen scrubbing bed to further purify the nitrogen to less than 4 ppm oxygen. This ultra-high purity (UHP) nitrogen was purged through the quartz tube for 18 hours at 85 sccm. Next, the UHP nitrogen feed was reduced from 85 sccm to 30 sccm and the furnace was turned on and heated to 400° C. to calcine the catalyst. The heating program for the furnace was: 4 hours ramp from room temperature to 400° C., dwell at 400° C. for 2 hours and then cool to ambient temperature naturally. Calcination yielded Catalyst 3.8.

Catalyst 3.8 was then submitted for ICP-MS analysis using the general ICP-MS procedure described herein using digestion method 2. The results are presented in Table 14.

Catalyst 3.8 was analyzed by EDS as per the general procedure SEM-EDS. Results are presented in Table 15.

Powder XRD data was collected as per General Procedure XRD above. The plot for this catalyst is available in FIG. 3. The raw data PXRD plot was used in establishing the range of the peak intensities presented in Table 16.

PSD analysis results are presented in Table 17.

Catalyst 3.8 was analyzed by nitrogen gas adsorption analysis for pore volume, BET surface area, and BJH pore size distributions analysis. Pore volume and BET surface area analysis results are presented in Table 18. BJH analysis results are presented in FIG. 10.

Catalyst 3.8 was then submitted for MRU testing. The results are presented in Table 20.

Example 17: Synthesis of Catalyst 3.9

$(NH_4)_6Mo_7O_{24}\cdot 4H_2O$ (SIGMA-ALDRICH®) (8.83 g) was weighed in a 250 mL round bottomed flask. The white solid was dissolved in 120 mL of distilled water with the aid of a 60° C. warm water bath and stirring to create a clear, colorless solution. $VOSO_4\cdot 3.46H_2O$ (SIGMA-ALDRICH®) (2.81 g) was weighed into a 250 mL beaker. The blue solid was dissolved in 120 mL of distilled water with the aid of a 60° C. warm water bath and stirring to create a clear, blue solution. The blue vanadium solution was added dropwise to the colorless molybdenum solution to produce a brown solution. To the brown solution, 2.71 g of sodium dodecyl sulfate (SIGMA-ALDRICH®) surfactant was added as a powder to produce a purple slurry with some emulsion present. The purple-emulsified slurry was stirred for 30 minutes at 60° C.

The purple slurry was added to a glass liner and the glass liner was added to a 600 mL PARR high pressure reactor. The PARR reactor was sealed and purged with 15 psig nitrogen gas and vacuum sequence ten times, then left under 15 psig nitrogen. The PARR reactor was placed into an oven and the oven was heated to 230° C. The reaction proceeded at 230° C. for 20 hours before being turned off and allowed to cool to room temperature.

Once cooled, the reactor was vented, opened, and the resulting spongy-slurry was filtered. The filtering was done using a Buchner funnel and 4 layers of qualitative filter paper (Whatman 28310-026). The mother liquor was blue and the solids grey. The solids were washed with 0.5 L of distilled water until the filtrate ran clear. The solids were further washed with denatured 0.5 L of ethanol.

The grey solids were transferred to a 200 mL round bottom flask with 50 mL of distilled water to create a suspension. In a 100 mL beaker, an aqueous solution of oxalic acid was made using 4 g of anhydrous oxalic acid and 50 mL water. The aqueous oxalic acid solution was added to the suspension contained in the 200 mL round bottoms flask. The suspension was left mixing at 500 rpm via a magnetic stir bar in the aqueous oxalic acid solution at 80° C. for 40 minutes, after which, the solution was removed from the heat to cool for 15 minutes. The mixture was filtered through a Buchner funnel using 4 Whatman #4 filter papers. The grey filter cake was rinsed with 500 mL of distilled water. The solids were dried at 90° C. overnight.

The precalcined catalyst were manually ground using a mortar and pestle and then loaded into a quartz boat. The quartz boat containing the precalcined catalyst was loaded into a quartz tube, which was placed into a split tube furnace. The quartz tube was purged with bulk nitrogen for 5 hours at 85 sccm, before the nitrogen feed was fed through an oxygen scrubbing bed to further purify the nitrogen to less than 4 ppm oxygen. This ultra-high purity (UHP) nitrogen was purged through the quartz tube for 18 hours at 85 sccm. Next, the UHP nitrogen feed was reduced from 85 sccm to 30 sccm and the furnace was turned on and heated to 400° C. to calcine the catalyst. The heating program for the furnace was: 4 hours ramp from room temperature to 400° C., dwell at 400° C. for 2 hours and then cool to ambient temperature naturally. The calcined catalyst produced Catalyst 3.9.

Catalyst 3.9 was then submitted for ICP-MS analysis using the general ICP-MS procedure described herein using digestion method 2. The results are presented in Table 14.

Catalyst 3.9 was analyzed by EDS as per the general procedure SEM-EDS. Results are presented in Table 15.

Powder XRD data was collected as per General Procedure XRD above. The plot for this catalyst is available in FIG. 3. The raw data PXRD plot was used in establishing the range of the peak intensities presented in Table 16.

Catalyst 3.9 was then submitted for MRU testing. The results are presented in Table 20.

Figure 14:
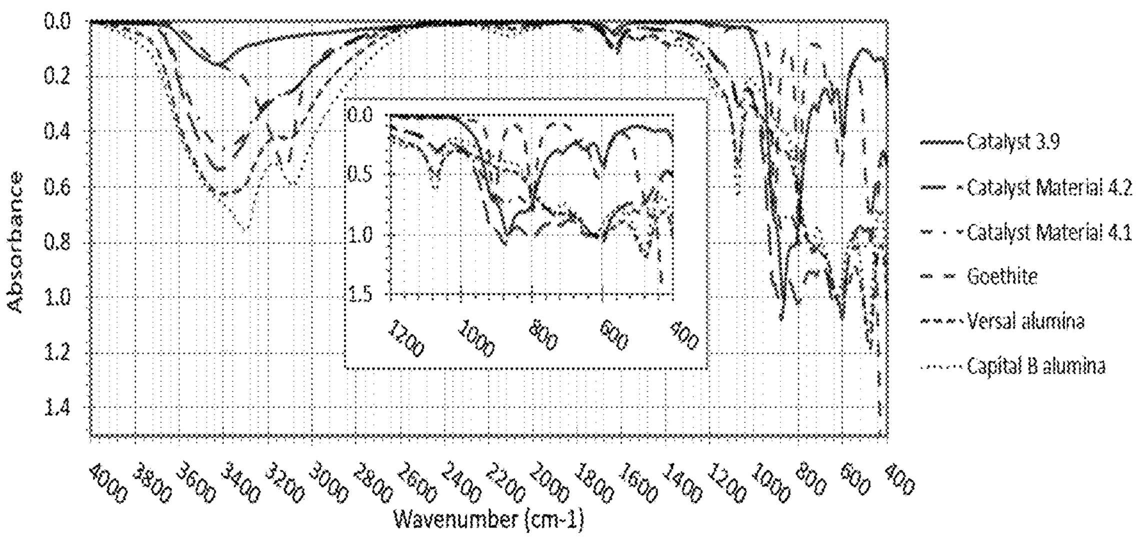
FIG. 14 shows the FTIR plot for Catalysts/Catalyst Materials 3.9, 4.1 and 4.2.

Catalyst 3.9 was then submitted for FTIR fingerprint. The results are presented in FIG. 14.

Example 18: Synthesis of Catalyst 3.10

$(NH_4)_6Mo_7O_{24}\cdot 4H_2O$ (SIGMA-ALDRICH®) (8.83 g) was weighed in a 250 mL round bottomed flask. The white solid was dissolved in 120 mL of distilled water with the aid of a 60° C. warm water bath and stirring to create a clear, colorless solution. $VOSO_4\cdot 3.46H_2O$ (SIGMA-ALDRCH®) (2.81 g) was weighed into a 250 mL beaker. The blue solid was dissolved in 120 mL of distilled water with the aid of a 60° C. warm water bath and stirring to create a clear, blue solution. The blue vanadium solution was added dropwise to the colorless molybdenum solution to produce a brown solution. To the brown solution, 2.70 g of sodium dodecyl sulfate (SIGMA-ALDRICH®) surfactant was added as a powder to produce a purple slurry with some emulsion present. The purple-emulsified slurry was stirred for 30 minutes at 60° C.

The purple slurry was added to a Teflon liner and the Teflon liner was added to a 600 mL PARR high pressure reactor. The PARR reactor was sealed and purged with 20 psig nitrogen gas and vacuum sequence ten times, then left under 20 psig nitrogen. The PARR reactor was placed into an oven and the oven was heated to 230° C. The reaction proceeded at 230° C. for 20 hours before being turned off and allowed to cool to room temperature.

Once cooled, the reactor was vented, opened, and the resulting spongy-slurry was filtered. The filtering was done using a Buchner funnel and 4 layers of qualitative filter paper. The mother liquor was blue and the solids grey. The solids were washed with 0.5 L of distilled water until the filtrate ran clear. The solids were further washed with denatured 0.5 L of ethanol.

The grey solids were transferred to a 200 mL round bottom flask with 50 mL of distilled water to create a suspension. In a 100 mL beaker, an aqueous solution of oxalic acid was made using 4 g of anhydrous oxalic acid and 50 mL water. The aqueous oxalic acid solution was added to the suspension contained in the 200 mL round bottoms flask. The suspension was left mixing at 500 rpm via a magnetic stir bar in the aqueous oxalic acid solution at 80° C. for 40 minutes, after which, the solution was removed from the heat to cool for 15 minutes. The mixture was filtered through a Buchner funnel using 4 Whatman #4 filter papers. The grey filter cake was rinsed with 500 mL of distilled water. The solids were dried at 90° C. overnight.

The precalcined catalyst were manually ground using a mortar and pestle and then loaded into a quartz boat. The quartz boat containing the precalcined catalyst was loaded into a quartz tube, which was placed into a split tube furnace. The quartz tube was purged with bulk nitrogen for 5 hours at 85 sccm, before the nitrogen feed was fed through an oxygen scrubbing bed to further purify the nitrogen to less than 4 ppm oxygen. This ultra-high purity (UHP) nitrogen was purged through the quartz tube for 18 hours at 85 sccm. Next, the UHP nitrogen feed was reduced from 85 sccm to 30 sccm and the furnace was turned on and heated to 400° C. to calcine the catalyst. The heating program for the furnace was: 4 hours ramp from room temperature to 400° C., dwell at 400° C. for 2 hours and then cool to ambient temperature naturally. The calcined catalyst produced was Catalyst 3.10.

Catalyst 3.10 was then submitted for ICP-MS analysis using the general ICP-MS procedure described herein using digestion method 2. The results are presented in Table 14.

Catalyst 3.10 was analyzed by EDS as per the general procedure SEM-EDS. The results are presented in Table 15.

Powder XRD data was collected as per General Procedure XRD above. The plot for this catalyst is available in FIG. 3. The raw data PXRD plot was used in establishing the range of the peak intensities presented in Table 16.

Catalyst 3.10 was analyzed by nitrogen gas adsorption analysis for pore volume, BET surface area, and BJH pore size distributions analysis. Pore volume and BET surface area analysis results are presented in Table 18. BJH analysis results are presented in FIG. 10.

Catalyst 3.10 was then submitted for MRU testing. The results are presented in Table 20.

Example 19: Synthesis of Catalyst 3.11

$(NH_4)_6Mo_7O_{24}\cdot4H_2O$ (SIGMA-ALDRICH®) (8.83 g) was weighed in a 250 mL round bottomed flask. The white solid was dissolved in 120 mL of distilled water with the aid of a 60° C. warm water bath and stirring to create a clear, colorless solution. $VOSO_4\cdot3.46H_2O$ (SIGMA-ALDRICH®) (2.81 g) was weighed into a 250 mL beaker. The blue solid was dissolved in 120 mL of distilled water with the aid of a 60° C. warm water bath and stirring to create a clear, blue solution. The blue vanadium solution was slowly poured into the colorless molybdenum solution to produce a brown solution. To the brown solution, 2.17 g of sodium octyl sulfate surfactant (SOS, SIGMA-ALDRICH®) was added as a powder to produce a purple slurry. The purple slurry was stirred for 30 minutes at 60° C.

The purple slurry was added to a glass liner and the glass liner was added to a 600 mL PARR high pressure reactor. The PARR reactor was sealed and purged with 15 psig nitrogen gas and vacuum sequence ten times, then left under 15 psig nitrogen. The PARR reactor was placed into an oven and the oven was heated to 220° C. The reaction proceeded at 220° C. overnight before being turned off and allowed to cool to room temperature.

Once cooled, the reactor was vented, opened, and the resulting slurry was filtered. The filtering was done using a Buchner funnel and 4 layers of qualitative filter paper. The solids were washed with 50 mL of distilled water. The solids were further washed with denatured 500 mL of ethanol. The solids were dried at 90° C. overnight and weighed to be 1.82 g.

The pre-calcined catalyst was manually ground using a mortar and pestle and then loaded into a quartz boat. The quartz boat containing the pre-calcined catalyst was loaded into a quartz tube, which was placed into a split tube furnace. The quartz tube was purged with bulk nitrogen for 5 hours at 85 sccm, before the nitrogen feed was fed through an oxygen scrubbing bed to further purify the nitrogen to less than 4 ppm oxygen. This ultra-high purity (UHP) nitrogen was purged through the quartz tube for 18 hours at 85 sccm. Next the UHP nitrogen feed was reduced from 85 sccm to 30 sccm and the furnace was turned on and heated to 400° C. to calcine the catalyst. The heating program for the furnace was: 4 hours ramp from room temperature to 400° C., dwell at 400° C. for 2 hours and then cool to ambient temperature naturally. The calcined catalyst produced was Catalyst 3.11.

Catalyst 3.11 was then submitted for ICP-MS analysis using the general ICP-MS procedure described herein using digestion method 2. The results are presented in Table 14.

Catalyst 3.11 was analyzed by EDS as per the general procedure SEM-EDS. Results are presented in Table 15.

Powder XRD data was collected as per General Procedure XRD above. The plot for this catalyst is available in FIG. 3. The raw data PXRD plot was used in establishing the range of the peak intensities presented in Table 16.

Catalyst 3.11 was then submitted for MRU testing. The results are presented in Table 20.

Example 20: Synthesis of Catalyst 3.12

$(NH_4)_6Mo_7O_{24}\cdot4H_2O$ (SIGMA-ALDRICH®) (13.26 g) was weighed in a 500 mL round bottomed flask. The white solid was dissolved in 150 mL of distilled water with the aid of a 60° C. warm water bath and stirring to create a clear, colorless solution. $VOSO_4\cdot3.46\ H_2O$ (SIGMA-ALDRICH®) (4.22 g) was weighed into a beaker. The blue solid was dissolved in 150 mL of distilled water with stirring at room temperature to create a clear, blue solution. The blue vanadium solution was poured slowly to the colorless molybdenum solution to instantly produce a purple solution. The resulting purple solution was stirred at 60° C. for 30 minutes. To the purple solution, 4.07 g of sodium dodecyl sulfate surfactant (SIGMA-ALDRICH®) was added as a powder to produce a purple slurry. The purple slurry was stirred for 30 minutes at 60° C. and then removed from heat and allowed to cool to room temperature.

The purple slurry was added to a glass liner and a magnetic stir bar added. The glass liner was added to a 600 mL PARR high pressure reactor. The PARR reactor was sealed and purged with 15 psig nitrogen gas and vacuum sequence ten times, then left under 15 psig nitrogen. The PARR reactor was setup in a heating mantle and heated via thermocouples and a temperature control box to 230° C. internal process temperature (temperature controller was set to 222° C.; the internal temperature was about 230-231° C. after running overnight). The reaction proceeded at 230-231° C. for 24 hours, with the slurry stirred via magnetic stirring, before being turned off and allowed to cool to room temperature.

Once cooled, the reactor was vented, opened, and the resulting spongy-slurry was filtered. The filtering was done using a Buchner funnel and four layers of qualitative filter paper. The mother liquor was blue and the solids grey. The solids were washed with water (1.5 L) until the filtrate ran clear. The solids were dried at 90° C. overnight and the next morning the dry, grey solids were weighed: 5.16 g.

The sodium dodecyl sulfate decomposition oils were removed from the solids through combustion (air treatment). The 5.16 g of solids were placed in a muffle furnace open to air at 280° C. for 2 hours. After the 280° C. air treatment, the grey solid was weighed to be 4.68 g.

The 4.68 g of precalcined catalyst were manually ground using a mortar and pestle and then loaded into a quartz boat. The quartz boat was loaded into a quartz tube, which was placed into a split tube furnace. The quartz tube was purged with bulk nitrogen for 5 hours at 85 sccm, before the nitrogen feed was fed through an oxygen scrubbing bed to further purify the nitrogen to less than 4 ppm oxygen. This ultra-high purity (UHP) nitrogen was purged through the quartz tube overnight at 85 sccm. The next morning the UHP nitrogen feed was reduced from 85 sccm to 30 sccm and the furnace was turned on and heated to 400° C. to calcine the catalyst. The heating program for the furnace was: 4 hours ramp from room temperature to 400° C., dwell at 400° C. for 2 hours and then cool to ambient temperature naturally. The calcined catalyst produced 4.50 g of black Catalyst 3.12.

Catalyst 3.12 was then submitted for ICP-MS analysis using the general ICP-MS procedure described herein using digestion method 2. The results are presented in Table 14.

Catalyst 3.12 was analyzed by EDS as per the general procedure SEM-EDS. Results are presented in Table 15.

Figure 8:
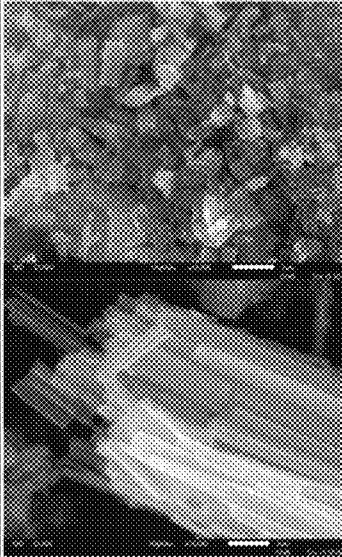
FIG. 8 shows the SEM images of Catalysts 3.12, 3.15-3.16 and 3.18.
Figure 8:
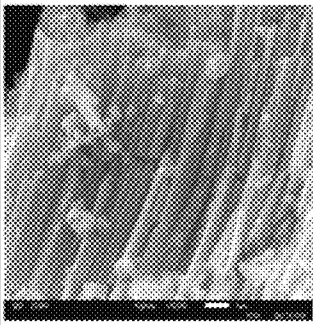
Figure 8:
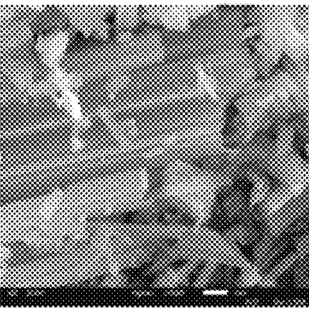
Figure 8:
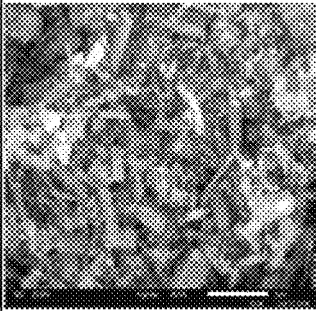
Figure 8:
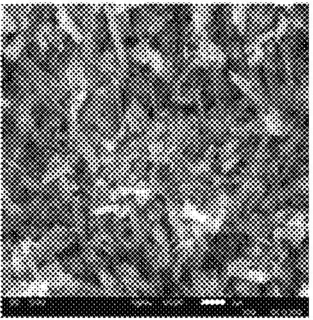
Figure 8:
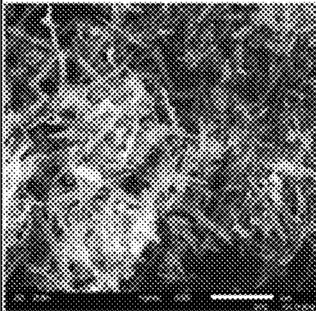
Figure 8:
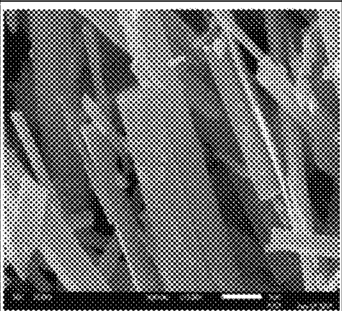
Figure 8:
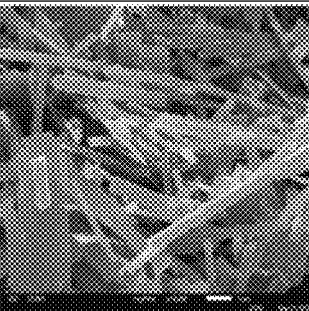
Figure 8:
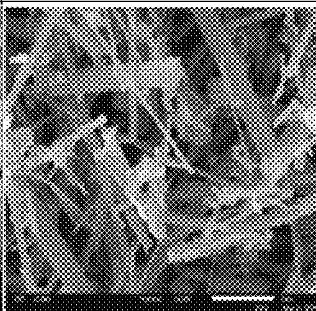

Catalyst 3.12 was submitted for SEM imaging. The results are presented in FIG. 8.

Powder XRD data was collected as per General Procedure XRD above. The plot for Catalyst 3.12 is available in FIG. 3. The raw data PXRD plot was used in establishing the range of the peak intensities presented in Table 16.

PSD analysis results are presented in Table 17.

Catalyst 3.12 was analyzed by nitrogen gas adsorption analysis for pore volume, BET surface area, and BJH pore size distributions analysis. Pore volume and BET surface area analysis results are presented in Table 18. BJH analysis results are presented in FIG. 10.

Catalyst 3.12 was then submitted for MRU testing. The results are presented in Table 20.

Example 21: Synthesis of Precalcined Catalyst 3.13

$(NH_4)_6Mo_7O_{24}\cdot 4H_2O$ (SIGMA-ALDRICH®) (44.20 g) was added to a 2 L round bottom flask with a magnetic stir bar. Subsequently, approximately 600 mL of distilled water was added and the $(NH_4)_6Mo_7O_{24}\cdot 4H_2O$ was dissolved with the aid of a 60° C. water bath. Next, $VOSO_4\cdot 3.46H_2O$ (SIGMA-ALDRICH®) (14.07 g) was placed into a 1 L beaker with a magnetic stir bar. Subsequently, approximately 600 mL of distilled water was added and the $VOSO_4\cdot 3.46H_2O$ was dissolved with the aid of a 60° C. water bath. Then, the vanadium solution was added to the round bottom flask containing the molybdenum solution while stirring at 60° C. Sodium dodecyl sulfate (SIGMA-ALDRICH®) was added to the round bottom flask containing the vanadium and molybdenum solution while stirring at 60° C. and the mixture was stirred for approximately 30 minutes at approximately 60° C.

The round bottom flask was then removed from the water bath and allowed to cool for 15 approximately minutes before transferring the solution to a 2 L glass liner. The round bottom flask was rinsed with distilled water and the rinse was transferred to the glass liner. The glass liner containing the purple solution was inserted into a 2 L PARR reactor. The PARR reactor unit was sealed and subsequently, the PARR reactor headspace was pumped and purged ten times with nitrogen. The headspace was left under approximately 15 psig nitrogen and the top valve on the PARR reactor was closed. Subsequently, the PARR reactor was stirred at approximately 150 rpm using an overhead stirrer at a process temperature of 230° C. (controller temperature set for 248° C.) for approximately 24 hours. The reaction mixture was then allowed to cool to approximately 67° C. and stirred at approximately 150 rpm for 18 hours.

The reaction mixture was filtered warm using a Buchner funnel, 4 qualitative filter papers, and an aspirator. The collected solid precalcined catalyst was rinsed with about 1 L of distilled water to produce precalcined Catalyst 3.13.

Example 22: Synthesis of Catalyst 3.14

A portion of precalcined Catalyst 3.13 was placed in a 100 mL beaker and dried in an oven at 90° C. overnight. The dried precalcined catalyst solids, weighing 7.34 g, were manually ground using a mortar and pestle and then loaded into a quartz boat. The quartz boat was loaded into a quartz tube, which was placed into a split tube furnace. The quartz tube was purged with bulk nitrogen for 5 hours at 85 sccm, before the nitrogen feed was fed through an oxygen scrubbing bed to further purify the nitrogen to less than 4 ppm oxygen. This ultra-high purity (UHP) nitrogen was purged through the quartz tube overnight at 85 sccm. The next morning the UHP nitrogen feed was reduced from 85 sccm to 30 sccm and the furnace was turned on and heated to 400° C. to calcine the catalyst. The heating program for the furnace was: 4 hours ramp from room temperature to 400° C., dwell at 400° C. for 2 hours and then cool to ambient temperature naturally. After the calcination was complete, large amount of yellow oil were observed throughout the tube. The calcined catalyst produced 4.92 g of Catalyst 3.14. CHN analysis was performed on the calcined catalyst (C % 2.18, H % 0.48, N % 0.21).

Catalyst 3.14 was then submitted for MRU testing. The results are presented in Table 20.

Example 23: Synthesis of Catalyst 3.15

A portion of precalcined Catalyst 3.13 was transferred to a Buchner funnel with 4 qualitative filter papers and washed with 500 mL of ethanol using an aspirator vacuum. The solids were dried at 90° C. overnight and weighed to be 4.74 g.

The 4.74 g of precalcined catalyst was manually ground using a mortar and pestle and then loaded into a quartz boat. The quartz boat was loaded into a quartz tube, which was placed into a split tube furnace. The quartz tube was purged with bulk nitrogen for 5 hours at 85 sccm, before the nitrogen feed was fed through an oxygen scrubbing bed to further purify the nitrogen to less than 4 ppm oxygen. This ultra-high purity (UHP) nitrogen was purged through the quartz tube for 18 hours at 85 sccm. Next the UHP nitrogen feed was reduced from 85 sccm to 30 sccm and the furnace was turned on and heated to 400° C. to calcine the catalyst. The heating program for the furnace was: 4 hours ramp from room temperature to 400° C., dwell at 400° C. for 2 hours and then cool to ambient temperature naturally. The calcined catalyst produced 4.70 g of Catalyst 3.15. CHN analysis was performed on the calcined catalyst (C % 0.07, H % 0.30, N % 0.13).

Catalyst 3.15 was then submitted for ICP-MS analysis using the general ICP-MS procedure described herein using digestion method 2. The results are presented in Table 14.

Catalyst 3.15 was analyzed by EDS as per the general procedure SEM-EDS. Results are presented in Table 15.

Catalyst 3.15 was submitted for SEM imaging. The results are presented in FIG. 8.

Powder XRD data was collected as per General Procedure XRD above. The plot for this catalyst is available in FIG. 3. The raw data PXRD plot was used in establishing the range of the peak intensities presented in Table 16.

PSD analysis results are presented in Table 17.

Bulk density measurements are presented in Table 19.

Catalyst 3.15 was then submitted for MRU testing. The results are presented in Table 20.

Example 24: Synthesis of Catalyst 3.16

A portion of precalcined Catalyst 3.13 was transferred to a 100 mL beaker and dried at 90° C. overnight. The dried solids were placed in a muffle furnace open to air at 280° C. for 3 hours. After the 280° C. air treatment, the grey solid was weighed to be 6.49 g.

The 6.49 g of precalcined catalyst was manually ground using a mortar and pestle and then loaded into a quartz boat. The quartz boat was loaded into a quartz tube, which was placed into a split tube furnace. The quartz tube was purged with bulk nitrogen for 5 hours at 85 sccm, before the nitrogen feed was fed through an oxygen scrubbing bed to further purify the nitrogen to less than 4 ppm oxygen. This ultra-high purity (UHP) nitrogen was purged through the quartz tube for 18 hours at 85 sccm. Next the UHP nitrogen feed was reduced from 85 sccm to 30 sccm and the furnace was turned on and heated to 400° C. to calcine the catalyst. The heating program for the furnace was: 4 hours ramp from room temperature to 400° C., dwell at 400° C. for 2 hours and then cool to ambient temperature naturally. The calcination yielded 6.21 g of Catalyst 3.16. CHN analysis was performed on the calcined catalyst (C % 0.54, H % 0.21, N % 0.18).

Catalyst 3.16 was then submitted for ICP-MS analysis using the general ICP-MS procedure described herein using digestion method 2. The results are presented in Table 14.

Catalyst 3.16 was analyzed by EDS as per the general procedure SEM-EDS. Results are presented in Table 15.

Catalyst 3.16 was submitted for SEM imaging. The results are presented in FIG. 8.

Powder XRD data was collected as per General Procedure XRD above. The plot for this catalyst is available in FIG. 3. The raw data PXRD plot was used in establishing the range of the peak intensities presented in Table 16.

PSD analysis results are presented in Table 17.

Catalyst 3.7 was analyzed by nitrogen gas adsorption analysis for pore volume, BET surface area, and BJH pore size distributions analysis. Pore volume and BET surface area analysis results are presented in Table 18. BJH analysis results are presented in FIG. 10.

Catalyst 3.16 was then submitted for MRU testing. The results are presented in Table 20.

Example 25: Synthesis of Catalyst 3.17

A 5.1 g portion of precalcined Catalyst 1.3 was loaded into a quartz boat. The quartz boat containing the precalcined catalyst was loaded into a quartz tube, which was placed into a tube furnace. The quartz tube was purged with bulk nitrogen for 8 hours at 400 sccm, before the nitrogen feed was fed through an oxygen scrubbing bed to further purify the nitrogen to less than 4 ppm oxygen. This ultra-high purity (UHP) nitrogen was purged through the quartz tube overnight at 400 sccm. The next morning, the furnace was turned on and heated to 400° C. to calcine the catalyst. The heating program for the furnace was: 4 hours ramp from room temperature to 400° C., dwell at 400° C. for 2 hours and then cool to ambient temperature naturally. The calcined catalyst, Catalyst 3.17, weighed 4.80 g.

Catalyst 3.17 was analyzed by EDS as per the general procedure SEM-EDS. Results are presented in Table 15.

Powder XRD data was collected as per General Procedure XRD above. The plot for this catalyst is available in FIG. 3. The raw data PXRD plot was used in establishing the range of the peak intensities presented in Table 16.

Catalyst 3.17 was then submitted for MRU testing. The results are presented in Table 20 and Table 30.

Example 26: Synthesis of Catalyst 3.18

$(NH_4)_6Mo_7O_{24}\cdot 4H_2O$ (SIGMA-ALDRICH®) (44.2035 g) was charged to a 2 L round bottom flask with 600 mL of distilled water, this was heated and stirred in a 60° C. oil bath until the solution became clear and colorless (5 minutes). $VOSO_4\cdot 3.36H_2O$ (SIGMA-ALDRICH®) (14.0699 g) was charged to a separate 1 L beaker with 600 mL of distilled water. This was heated and stirred using a 60° C. oil bath until the solution turned an electric blue color (10 minutes). The electric blue vanadyl sulfate solution was transferred to the ammonium molybdate solution in the 2 L round bottom flask, and the resulting purple solution was held at 60° C. To the 2 L round bottom flask was also charged sodium dodecyl sulfate (SIGMA-ALDRICH®, 13.5735 g) at 60° C. The purple solution was stirred in a 60° C. water bath for 30 minutes. Next, the solution was transferred to a 2 L glass liner. The final volume was recorded to be 1340 mL. The glass liner was transferred into the 2 L reactor, the gap between the glass liner and the reactor was filled with distilled water. Afterwards, the reactor was sealed, and the headspace purged ten times by filling the reactor with 15 psi $N_2$ (g) and evacuated with vacuum. Subsequently, 15 psi $N_2$ (g) headspace was left in the reactor. Next, the reactor was placed in an oven for 24 hours at 230° C. with a 1-hour ramp time and a 24-hour cooling time. Afterwards, the reactor was vented, and the contents of the reactor were filtered through 4 qualitative filter papers. The dark purple powder collected on the filter paper was rinsed with 1.25 L of distilled water.

The dark purple powder was dried in the oven at 90° C. overnight. Following the drying step, the purple powder (17.49 g) was air treated in a muffle furnace (1-hour ramp to 280° C. and dwell for 26 hours). After the muffle furnace treatment, the purple powder (14.39 g) was submitted for CHN analysis (C % 0.87, H % 0.11, N % 0.65). The precalcined catalyst was pressed with a spatula into a quartz boat. The quartz boat containing the precalcined catalyst was loaded into a quartz tube, which was placed into a split tube furnace. The quartz tube was purged with bulk nitrogen for 8 hours at 400 sccm, before the nitrogen feed was fed through an oxygen scrubbing bed to further purify the nitrogen to less than 4 ppm oxygen. This ultra-high purity (UHP) nitrogen was purged through the quartz tube for 18 hours at 400 sccm. Next, the furnace was turned on and heated to 400° C. to calcine the catalyst. The heating program for the furnace was: 4 hours ramp from room temperature to 400° C., dwell at 400° C. for 2 hours and then cool to ambient temperature naturally. CHN analysis was performed on the calcined catalyst (C % 0.45, H % 0.02, N % 0.54).

Catalyst 3.18 was analyzed by EDS as per the general procedure SEM-EDS. Results are presented in Table 22.

Catalyst 3.18 was submitted for SEM imaging. The results are presented in FIG. 8.

Powder XRD data was collected as per General Procedure XRD above. The plot for Catalyst 3.18 is available in FIG. 3 The raw data PXRD plot was used in establishing the range of the peak intensities presented in Table 16.

PSD analysis results are presented in Table 17

Catalyst 3.18 was then submitted for MRU testing. The results are presented in Tables 20, 28 and 29.

ICP-MS Analysis of Catalysts 3.7-3.12, 3.15 and 3.16.

The ICP-MS results for Catalysts 3.7-3.12, 3.15 and 3.16 are presented in Table 14.

TABLE 14

| | Measured Concentration (ppm) | | |
|---|---|---|---|
| Sample | Mo | V | Metal Molar Ratio |
| Catalyst 3.7 | 570640 | 130200 | $Mo_1V_{0.43}$ |
| Catalyst 3.8 | 566100 | 124000 | $Mo_1V_{0.41}$ |
| Catalyst 3.9 | 532800 | 123500 | $Mo_1V_{0.44}$ |
| Catalyst 3.10 | 579800 | 131700 | $Mo_1V_{0.43}$ |
| Catalyst 3.11 | 541600 | 137000 | $Mo_1V_{0.48}$ |
| Catalyst 3.12 | 576700 | 132500 | $Mo_1V_{0.43}$ |
| Catalyst 3.15 | 540000 | 115500 | $Mo_1V_{0.40}$ |
| Catalyst 3.16 | 574700 | 137400 | $Mo_1V_{0.45}$ |

EDS Analysis of Catalysts 3.7-3.12 and 3.15-3.18.

The EDS analysis of Catalysts 3.7-3.12 and 3.15-3.18 are presented in Table 15.

TABLE 15

| | Elements | | |
|---|---|---|---|
| Catalyst Code | Mo | V | Catalyst Material Formula |
| Catalyst 3.17 | 52.94 | 11.75 | $Mo_1V_{0.42}$ |
| Catalyst 3.9 | 51.97 | 12.29 | $Mo_1V_{0.45}$ |
| Catalyst 3.10 | 51.89 | 12.25 | $Mo_1V_{0.44}$ |
| Catalyst 3.11 | 51.11 | 12.72 | $Mo_1V_{0.47}$ |
| Catalyst 3.7 | 51.08 | 11.98 | $Mo_1V_{0.44}$ |
| Catalyst 3.8 | 52.57 | 11.77 | $Mo_1V_{0.42}$ |
| Catalyst 3.15 | 51.41 | 11.37 | $Mo_1V_{0.42}$ |
| Catalyst 3.16 | 51.51 | 11.39 | $Mo_1V_{0.42}$ |
| Catalyst 3.12 | 50.96 | 11.67 | $Mo_1V_{0.43}$ |
| Catalyst 3.18 | 52.55 | 12.27 | $Mo_1V_{0.44}$ |

PXRD Analysis of Catalysts 3.7-3.12 and 3.17-3.18.

Figure 3:
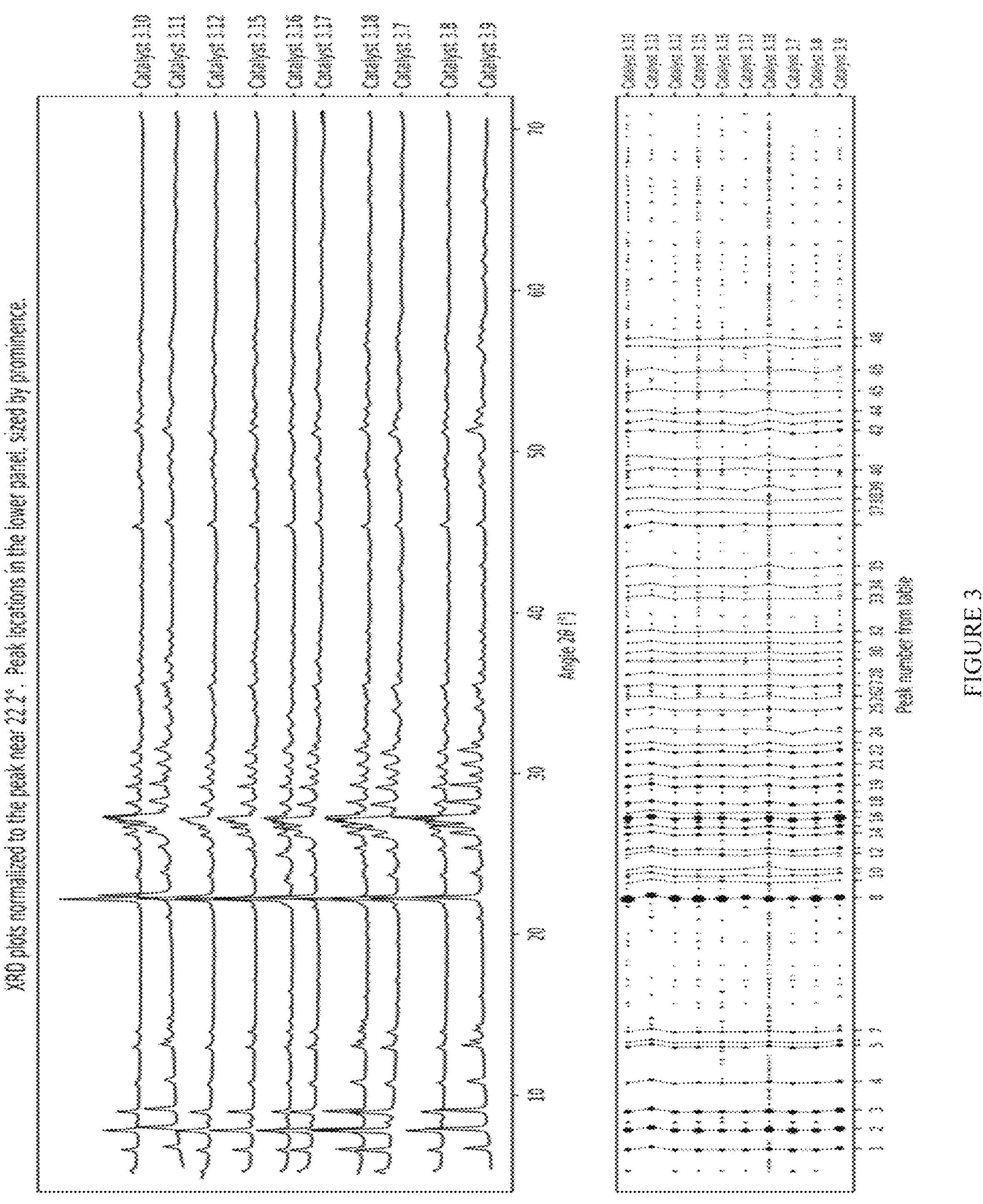
FIG. 3 shows the overlaid XRD plots of Catalysts 3.7-3.12 and 3.15-3.18.

Table 16 presents reflection angles and corresponding intensity for Catalysts 3.7-3.12 and 3.15-3.18 (nitrogen calcined baseline). FIG. 3 presents the plot correlating to peak numbers.

TABLE 16

| Peak Number | Min Angle | Max Angle | Min Intensity | Max Intensity |
|---|---|---|---|---|
| 1 | 6.604 | 6.802 | 32.0% | 73.9% |
| 2 | 7.814 | 8.012 | 50.9% | 119.2% |
| 3 | 8.958 | 9.178 | 40.3% | 81.5% |
| 4 | 10.718 | 10.960 | 21.5% | 43.1% |
| 5 | 12.962 | 13.182 | 24.6% | 47.4% |
| 6 | 13.248 | 13.468 | 18.6% | 36.5% |
| 7 | 13.908 | 14.128 | 22.1% | 42.3% |
| 8 | 22.202 | 22.444 | 100.0% | 100.0% |
| 9 | 23.192 | 23.456 | 17.1% | 36.1% |
| 10 | 23.610 | 23.874 | 20.1% | 40.3% |
| 11 | 24.006 | 24.248 | 18.7% | 36.7% |
| 12 | 24.908 | 25.194 | 18.7% | 38.8% |
| 13 | 25.216 | 25.458 | 23.7% | 44.3% |
| 14 | 26.140 | 26.382 | 32.0% | 58.1% |
| 15 | 26.602 | 26.822 | 35.0% | 75.1% |
| 16 | 27.130 | 27.328 | 50.3% | 118.1% |
| 17 | 27.526 | 27.746 | 22.2% | 39.8% |
| 18 | 28.076 | 28.296 | 31.2% | 61.4% |
| 19 | 29.132 | 29.374 | 31.7% | 56.8% |
| 20 | 29.726 | 29.968 | 23.2% | 41.0% |
| 21 | 30.408 | 30.628 | 25.0% | 45.3% |
| 22 | 31.288 | 31.508 | 25.2% | 48.1% |
| 23 | 31.728 | 31.948 | 19.0% | 37.6% |
| 24 | 32.454 | 32.916 | 17.0% | 33.3% |
| 25 | 33.928 | 34.148 | 18.5% | 36.2% |
| 26 | 34.676 | 34.874 | 17.4% | 35.6% |
| 27 | 35.380 | 35.578 | 22.3% | 37.9% |
| 28 | 36.128 | 36.304 | 17.9% | 33.4% |
| 29 | 36.986 | 37.096 | 18.6% | 35.7% |
| 30 | 37.426 | 37.646 | 17.1% | 32.2% |
| 31 | 38.064 | 38.240 | 17.3% | 32.7% |
| 32 | 38.724 | 38.900 | 16.3% | 32.2% |
| 33 | 40.836 | 41.100 | 15.7% | 30.7% |
| 34 | 41.562 | 41.826 | 16.8% | 31.6% |
| 35 | 42.728 | 43.036 | 16.0% | 31.2% |
| 36 | 45.302 | 45.610 | 24.6% | 36.3% |
| 37 | 46.160 | 46.402 | 16.1% | 31.2% |
| 38 | 46.952 | 47.150 | 15.4% | 30.6% |
| 39 | 47.612 | 47.942 | 17.9% | 32.5% |
| 40 | 48.800 | 48.998 | 20.4% | 33.5% |
| 41 | 49.526 | 49.768 | 18.0% | 35.2% |
| 42 | 51.110 | 51.374 | 22.9% | 40.7% |
| 43 | 51.616 | 51.990 | 20.3% | 36.3% |
| 44 | 52.298 | 52.628 | 19.2% | 34.1% |
| 45 | 53.684 | 53.904 | 18.8% | 35.7% |
| 46 | 54.916 | 55.202 | 17.5% | 33.5% |
| 47 | 56.412 | 56.632 | 18.4% | 34.5% |
| 48 | 56.918 | 57.116 | 18.7% | 34.3% |

PSD Analysis of Catalysts 3.7, 3.8, 3.12, 3.15, and 3.16

The statistical data from the PSD of Catalysts 3.7, 3.8, 3.12, 3.15, and 3.16 is presented in Table 17.

TABLE 17

| Sample | Catalyst 3.8 | Catalyst 3.12 | Catalyst 3.15 | Catalyst 3.16 |
|---|---|---|---|---|
| Maximum | 14.40 | 21.44 | 55.44 | 45.94 |
| Minimum | 0.11 | 0.08 | 0.15 | 0.09 |
| Mean | 1.24 | 1.21 | 2.92 | 2.38 |
| Median | 0.94 | 0.70 | 1.08 | 0.88 |
| Mode | 0.77-1.25 | 0.37-0.47 | 0.77-0.98 | 0.47-0.60 |
| Range | 14.29 | 21.36 | 55.29 | 45.85 |
| Skewness | 4.16 | 5.30 | 5.04 | 5.07 |
| Kurtosis | 30.15 | 41.68 | 29.02 | 33.85 |
| Standard Deviation | 1.18 | 1.70 | 6.37 | 4.41 |
| D10 | 0.35 | 0.25 | 0.40 | 0.26 |
| D25 (Quartile 1) | 0.54 | 0.38 | 0.64 | 0.44 |
| D50 | 0.94 | 0.70 | 1.08 | 0.88 |

TABLE 17-continued

| Sample | Catalyst 3.8 | Catalyst 3.12 | Catalyst 3.15 | Catalyst 3.16 |
|---|---|---|---|---|
| D75 (Quartile 3) | 1.49 | 1.39 | 2.25 | 2.40 |
| D90 | 2.43 | 2.42 | 5.27 | 5.55 |

BET Analysis of Catalysts 3.7, 3.8, 3.10, 3.12, and 3.16

The results of nitrogen gas adsorption analysis for pore volume and BET surface area analysis for Catalysts 3.7, 3.8, 3.10, 3.12, and 3.16 are presented in Table 18.

TABLE 18

| Sample | BET Surface Area ($m^2/g$) | Pore Volume ($cm^3/g$) |
|---|---|---|
| Catalyst 3.7 | 8.3 | 0.02 |
| Catalyst 3.8 | 8.9 | 0.03 |
| Catalyst 3.10 | 6.8 | 0.02 |
| Catalyst 3.12 | 16.0 | 0.05 |
| Catalyst 3.16 | 10.7 | 0.02 |

Bulk Density Measurements for Catalyst 3.15

The bulk density measurements for Catalyst 3.15 are presented in Table 19.

TABLE 19

| Sample | Measurements (g/mL) | Average (g/mL) |
|---|---|---|
| Catalyst 3.15 | 1.2095 | 1.2241 |
| | 1.2367 | |
| | 1.2260 | |

Activity and Selectivity for Catalysts 3.1, 3.6-3.712 and 3.14-3.18

The MRU results for Catalysts 3.1, 3.6-3.12 and 3.14-3.18 are presented in Table 20.

TABLE 20

| Sample | 35 mol. % Ethane Conversion Temperature (° C.) | Selectivity to Ethylene (mol. %) | MRU Loading Method |
|---|---|---|---|
| Catalyst 3.1 | 345 | 83 | Method 1 |
| Catalyst 3.6 | 337 | 80 | Method 1 |
| Catalyst 3.7 | 322 | 85 | Method 1 |
| Catalyst 3.8 | 345 | 84 | Method 1 |
| Catalyst 3.9 | 310 | 86 | Method 1 |
| Catalyst 3.10 | 318 | 86 | Method 1 |
| Catalyst 3.11 | 325 | 83 | Method 1 |
| Catalyst 3.12 | 330 | 87 | Method 1 |
| Catalyst 3.14 | >400 | — | Method 1 |
| Catalyst 3.15 | 313 | 88 | Method 1 |
| Catalyst 3.16 | 334 | 87 | Method 1 |
| Catalyst 3.17 | 348 | 79 | Method 1 |
| Catalyst 3.18 | 326 | 87 | Method 1 |

Synthesis of Catalyst Materials 4.1-4.9

Example 27: Synthesis of Catalyst Material 4.1

Catalyst 3.2 (4.5 g, 32 wt. %) was placed in a 100 mL beaker. Subsequently, 8.44 g (60 wt. %) of VERSAL™ 250 alumina (UOP) and goethite (SIGMA-ALDRICH®) (1.12 g, 8 wt. %) were added to the beaker. Distilled water (approx. 40 mL) was added to the beaker and the mixture was stirred manually. The beaker was then placed in a 100° C. silicone oil bath and the reaction mixture was stirred at approximately 85 rpm. The oil bath temperature was increased to 110° C. after about an hour and the reaction mixture was stirred until it took on a paste-like consistency, which took about 1.5 hours. The beaker was then taken out of the oil bath and placed into an oven at 90° C. and allowed to dry overnight. Subsequently, the material was taken out of the oven and placed in a muffle furnace at 350° C. for 2.5 hours and then allowed to cool overnight to room temperature yielding Catalyst material 4.1.

Catalyst Material 4.1 was analyzed by ICP-MS using the general ICP-MS procedure described herein using digestion method 3. The ICP-MS results for Catalyst material 4.1 are presented in Table 21.

Catalyst Material 4.1 was analyzed by EDS as per the general procedure SEM-EDS. Results are presented in Table 22.

Figure 9:
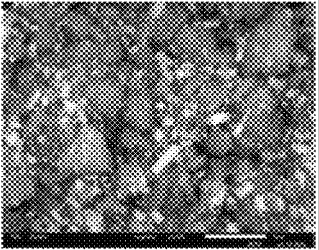
FIG. 9 shows the SEM images of Catalyst Materials 4.1-4.2 and 4.6-4.9.
Figure 9:
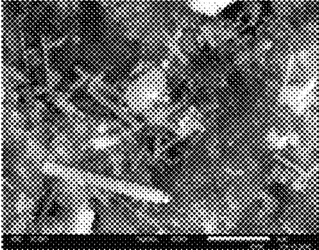
Figure 9:
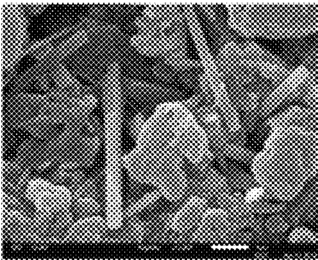
Figure 9:
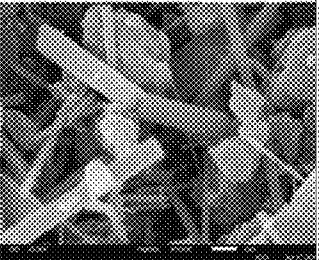
Figure 9:
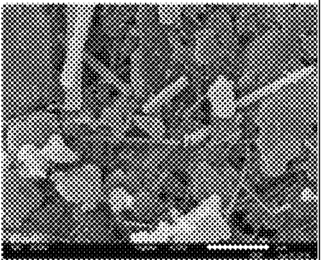
Figure 9:
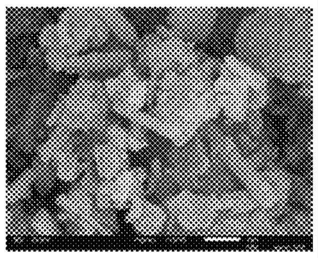
Figure 9:
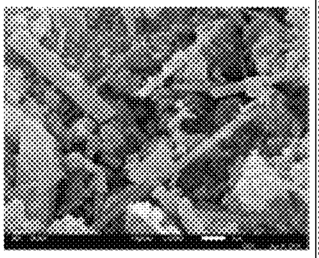
Figure 9:
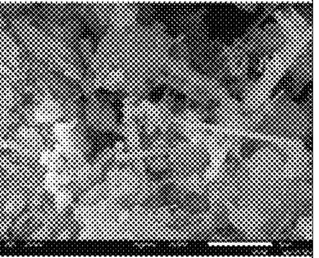
Figure 9:
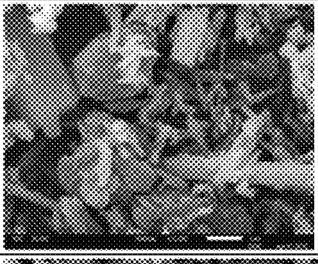
Figure 9:
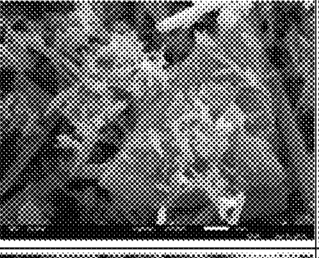
Figure 9:
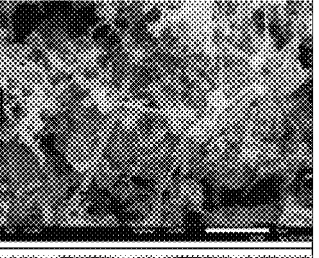
Figure 9:
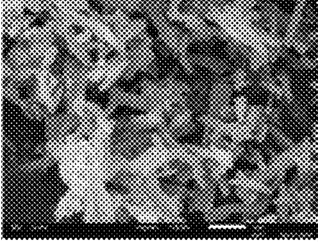
Figure 9:
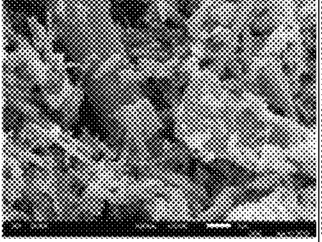
Figure 9:
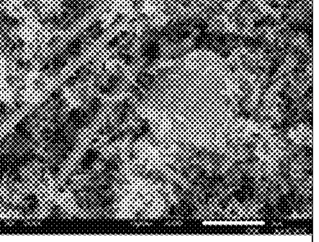

Catalyst Material 4.1 was submitted for SEM imaging. The results are presented in FIG. 9.

Figure 4:
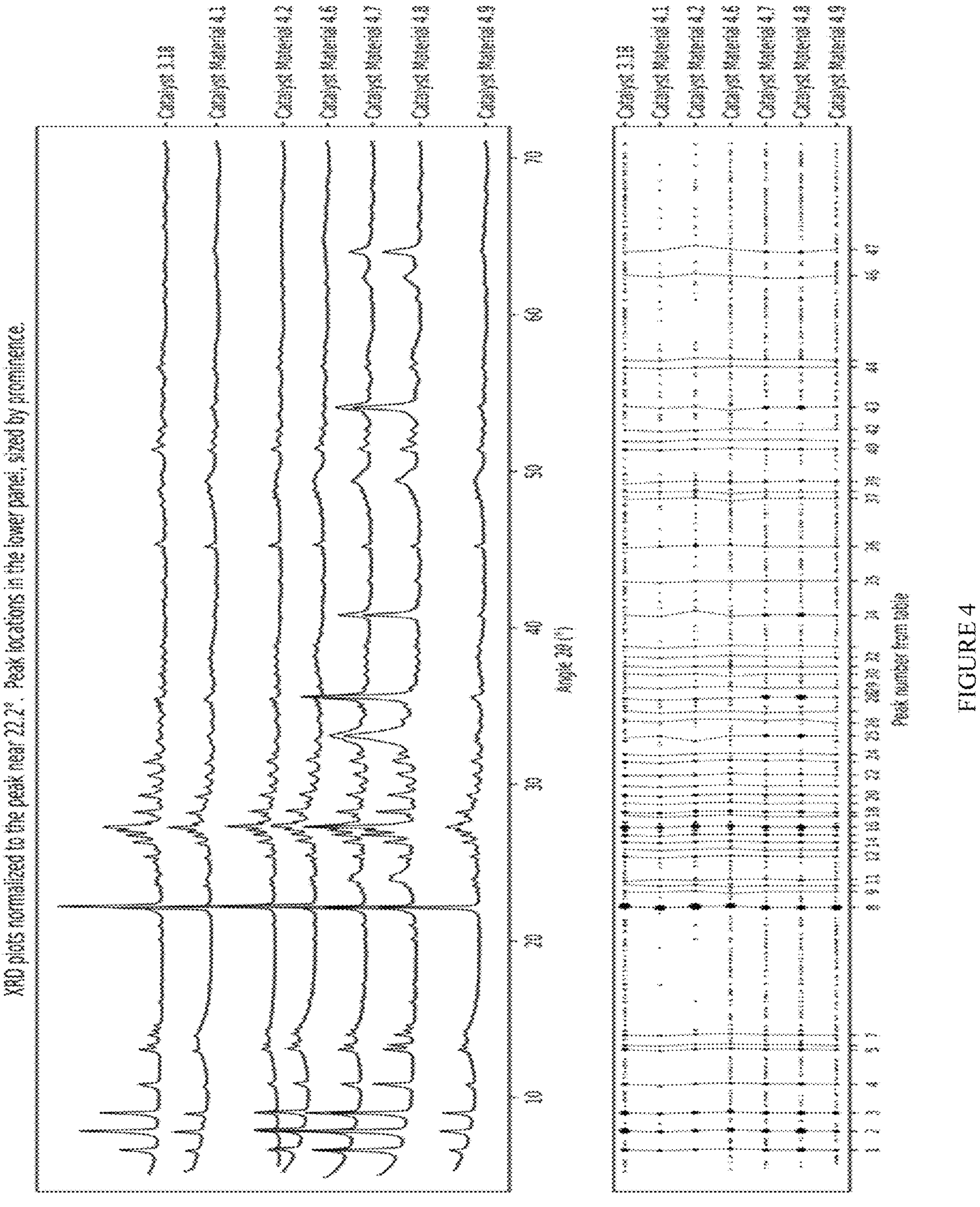
FIG. 4 shows the overlaid XRD plots of Catalyst 3.18 and Catalyst Materials 4.1-4.2 and 4.6-4.9.

Powder XRD data was collected as per the general XRD disclosed herein. The plot for Catalyst Material 4.1 is available in FIG. 4. The raw data PXRD plot was used in establishing the range of the peak intensities presented in Table 23.

Catalyst Material 4.1 was then submitted for particle size distribution analysis by SEM. The results are presented in Table 24.

Figure 12:
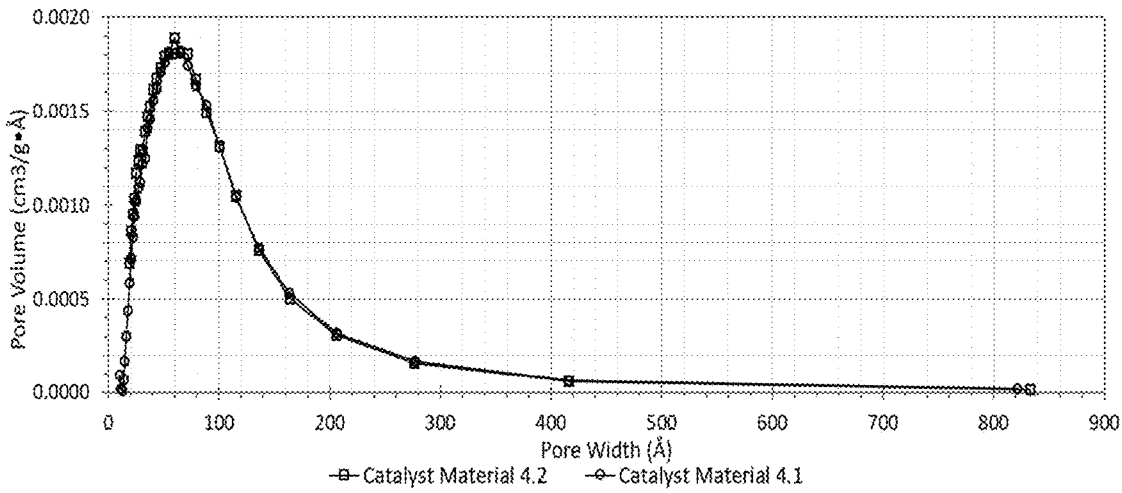
FIG. 12 shows the BJH plot for Catalyst Materials 4.1 and 4.2.
Figure 13:
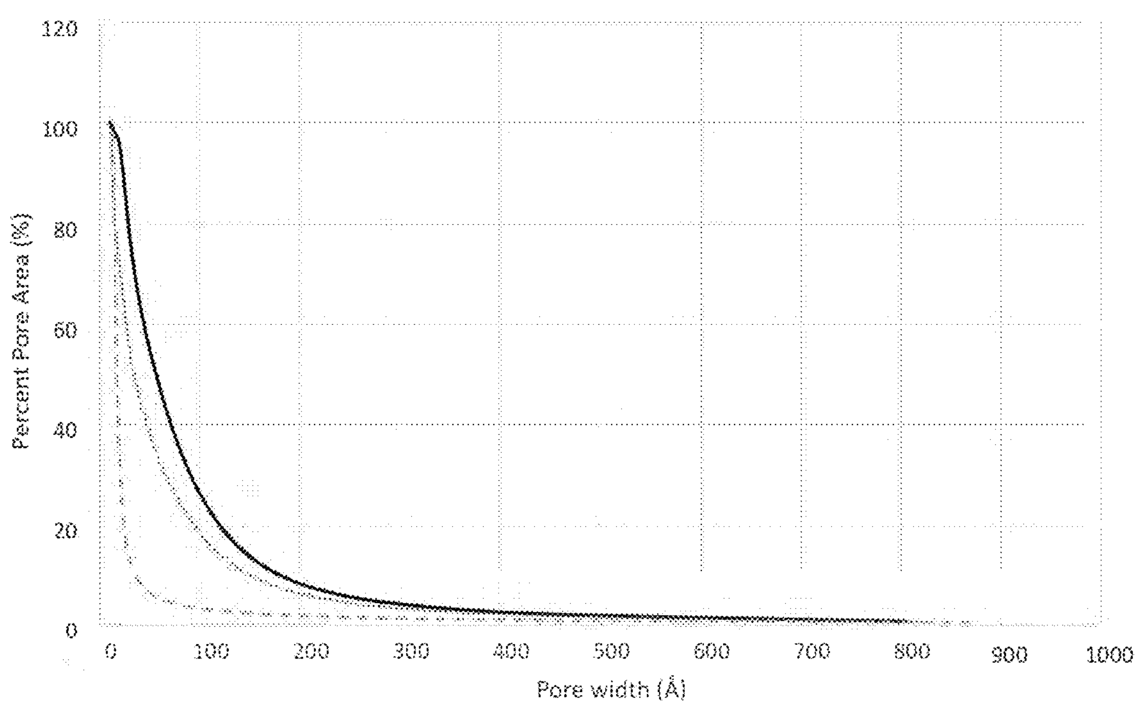
FIG. 13 shows the BET pore volume vs. pore area for Catalyst Materials 4.6-4.8.

BET Analysis results are presented in Table 25. BJH analysis results are presented in FIG. 12.

Bulk density measurements are presented in Table 26.

Catalyst Material 4.1 was then submitted for MRU testing. The results are presented in Table 27.

Catalyst Material 4.1 was submitted for FTIR fingerprint analysis. The results are presented in FIG. 14.

Example 28: Synthesis of Catalyst Material 4.2

To a 100 mL beaker was charged 4.47 g of Catalyst 3.4, 6.705 g of VERSAL™ 250 alumina, and 20 mL of distilled water. The beaker was then placed directly on a heat plate and the heat plate was set to 80° C. Further, an overhead agitator was set up with a glass stir rod and 0.5-inch Teflon stir blade, and the slurry was agitated at 100 rpm. After 1.25 hours the slurry turned into a paste. The material was then dried overnight in a 90° C. oven. Subsequently, the material was calcined in air in a muffle furnace at 350° C. for 2 hours with a ramp time of 30 minutes to yield Catalyst Material 4.2.

Catalyst Material 4.2 was submitted for SEM imaging. The results are presented in FIG. 9.

Powder XRD data was collected as per the general XRD procedure described herein. The plot for Catalyst Material 4.2 is available in FIG. 4. The raw data PXRD plot was used in establishing the range of the peak intensities presented in Table 23.

BET Analysis results are presented in Table 25. BJH analysis results are presented in FIG. 12.

Bulk density measurements are presented in Table 26.

Catalyst Material 4.2 was submitted for MRU testing. The results are presented in Table 27.

Catalyst Material 4.2 submitted for FTIR fingerprint analysis. The results are presented in FIG. 14.

Example 29: Synthesis of Catalyst Material 4.3

13.26 g of $(NH_4)_6Mo_7O_{24}·4H_2O$ was charged into a 500 mL round bottom flask with 180 mL of distilled water. The white powder was dissolved using a magnetic stir bar while being placed in a 60° C. water bath. To a 250 mL beaker with a magnetic stir bar was charged 4.22 g of $VOSO_4·3.46H_2O$ and 180 mL of distilled water. The beaker, which contained a magnetic stir bar, was clamped into a 60° C. water bath, and the solution was stirred for 30 minutes at 60° C. to dissolve. After which, the electric blue solution of $VOSO_4$ was charged into the round bottom flask containing the $(NH_4)_6Mo_7O_{24}$ solution while continuously stirring at 60° C. Following this addition, 4.07 g of sodium dodecyl sulfate was charged into the round bottom flask. The mixture was stirred for 30 minutes at 60° C. Subsequently, the solution in the round bottom flask was removed from the water bath for one hour and cooled to room temperature. The room temperature solution was transferred to a 600 mL glass PARR rector liner. Rinsings from the round bottom flask were charged to the 600 mL liner. The reactor was sealed and evacuated ten times with vacuum and 15 psi nitrogen. Following, the tenth evacuation and nitrogen back fill the PARR reactor was left under 15 psi of nitrogen and scaled. The PARR reactor was placed in a 230° C. oven for 19 hours and 15 minutes. After which, it was removed from the oven and left to cool for 2 hours. Subsequently, the pressure was released, the reactor was opened, and the contents were filtered through 4 quantitative filter papers using a Buchner funnel. The resulting purple, grey powder was rinsed with distilled water and ethanol. Following the filtration the grey catalyst was dried in an oven at 90° C. for 90 hours.

The catalyst was taken out of oven and cooled to room temperature. After which, the catalyst was ground using a mortar and pestle. 4.95 g of the light and fluffy catalyst was transferred into two split tube boats, purged with bulk nitrogen gas at 14 scpm for 6 hours. Subsequently, the split tube containing the catalyst was purged with purified nitrogen at 14 scpm overnight. The temperature program on the split tube was turned on. The split tube hated up to 400° C. over 4 hours, held at 400° C. for 2 hours and then cooled down to room temperature with a flow of 5.5 scpm. The calcination yielded 4.65 g of catalyst which was removed from the split tube.

A portion of the catalyst prepared above (4.0 g), VERSAL™ 250 alumina (UOP) (6.0 g), SUPERFLOC® (CYTEC) (0.023 g; polyacrylamide N-100/300), and distilled water (approx. 40 mL) were added to a 100 mL beaker. The beaker was then placed into an oil bath at approximately 100° C. and the mixture was stirred at approximately 85 rpm until the mixture formed a paste, which took about 1.5 hours. The beaker was then taken out of the oil bath and placed in an oven at approximately 90° C. overnight to dry.

Next, the material was taken out of the oven and placed into a muffle furnace at 350° C. for 2.5 hours yielding Catalyst Material 4.3. Catalyst Material 4.3 was then allowed to cool.

Catalyst Material 4.3 was then submitted for MRU testing. The results are presented in Table 27.

Example 30: Synthesis of Catalyst Material 4.4

To a 500 mL RBF with a magnetic stir bar was charged 13.26 g of $(NH_4)_6Mo_7O_{24}\cdot 4H_2O$ and 180 ml of distilled water. The round bottom flask was clamped into a water bath, and heated to 60° C. To a separate 250 mL beaker with a magnetic stir bar was charged 4.22 g of $VOSO_4\cdot 3.46H_2O$ and 180 mL of distilled water. The beaker was clamped into a 60° C. water bath and the $VOSO_4\cdot 3.46H_2O$ was stirred to dissolve over the course of 20 minutes. Following that, the electric blue vanadyl solution was charged to the clear and colorless ammonium molybdate solution at 60° C. To this purple solution was charged 4.07 g of sodium dodecylsulfate while continuously stirring the solution at 60° C. This mixture was stirred at 60° C. for 30 minutes. Subsequently, the solution was removed from the water bath, cooled to room temperature and transferred to a 600 mL PARR reactor glass liner. The liner was placed into the PARR reactor and the reactor was sealed. Following this, the PARR reactor was purged with nitrogen gas and evacuated slowly ten times. The PARR reactor was left under 15 psig of nitrogen gas. The PARR reactor was placed in an oven and heated to 230° C. for 22.5 hours. Next, the PARR reactor was cooled, the pressure was released and the glass liner containing the catalyst aqueous mixture was removed.

Subsequently, the purple/grey catalyst aqueous mixture was filtered through a Buchner funnel with 4 qualitative filter papers. A water aspirator was set up to draw vacuum on the catalyst mixture. The catalyst mixture on the filter paper was rinsed with 1.2 L of distilled water and 500 mL of ethanol resulting in a grey colored catalyst filter cake. Following the filtration and rinsing step the catalyst was dried at 90° C. for 18 hours. Following the drying step, the light and fluffy catalyst powder was ground using a mortar and pestle. To a calcination boat was weighed 5.47 g of catalyst. This boat was placed into the split tube calcination furnace and purged with bulk nitrogen at 14 slpm for 6 hours. Following that, the split tube furnace was purged using purified nitrogen at 14 slpm for 18 hours. Subsequently, the split tube furnace was ramped up to 400° C. for 4 hours, held at 400° C. for 2 hours and cooled to room temperature under a 5.5 slpm flow of purified nitrogen. This yielded 4.97 g of a grey catalyst material.

Catalyst prepared from the description above (4.0 g), VERSAL™ 250 alumina (UOP) (6.0 g), SUPERFLOC® (CYTEC) (0.022 g; polyacrylamide N-100/300), and distilled water (approx. 25 mL) were added to a 100 mL beaker. The beaker was then placed into an oil bath at approximately 100° C. and the mixture was stirred at approximately 85 rpm until the mixture formed a paste, which took about 1 hour. The beaker was then taken out of the oil bath and placed in an oven at approximately 90° C. overnight to dry.

Next, the material was taken out of the oven and placed into a muffle furnace at 350° C. for 2.5 hours to yield Catalyst Material 4.4.

Catalyst Material 4.4 was then submitted for MRU testing. The results are presented in Table 27.

Example 31: Synthesis of Catalyst Material 4.5

Catalyst 3.6 (3.52 g), VERSAL™ 250 alumina (UOP) (6.6 g), goethite (0.88 g), and distilled water (approx. 40 mL) were added to a 100 mL beaker. Next, the beaker was placed into an oil bath at approximately 100° C. and stirred at approximately 80 rpm until the mixture took on a past-like consistency, which took approximately 1.5 hours. The reaction mixture was stirred using an electronic overhead stirrer equipped with Teflon blade agitator. The beaker was then taken out of the oil bath and placed in an oven at approximately 90° C. allowed to dry over the weekend. Subsequently, the material was broken up with a spatula and then placed in a muffle furnace at 350° C. for 4.5 hours to yield Catalyst Material 4.5 (10.14 g).

Catalyst Material 4.5 was analyzed by ICP-MS using the general ICP-MS procedure described herein using ICP digestion method 3. The ICP-MS results for Catalyst Material 4.5 are presented in Table 21.

Catalyst Material 4.5 was then submitted for MRU testing. The results are presented in Table 27.

Example 32: Synthesis of Catalyst Material 4.6

Catalyst 3.18 (2.75 g), VERSAL™ 250 alumina (UOP) (6.41 g) and distilled water (approximately 20 mL) were added to a 100 mL beaker which formed a light purple suspension. Subsequently, the beaker was clamped into an oil bath at approximately 100° C. and stirred at approximately 106 ppm until the mixture took on a periwinkle purple past-like consistency, which took approximately 1.4 hours. The reaction mixture was stirred using an electronic overhead stirrer equipped with a half inch Teflon agitator blade and glass stir shaft. Subsequently the beaker was removed from the oil bath and placed in a 90° C. oven to dry for approximately 18 hours. The light purple powder was crushed up and heated in an air muffle furnace at 350° C. for 2 hours with a ramp time of 0.5 hours. This yielded a light grey Catalyst Material 4.6 (7.79 g).

Catalyst Material 4.6 was analyzed by EDS as per the general SEM-EDS procedure described herein. Results are presented in Table 22.

Catalyst Material 4.6 was submitted for SEM imaging. The results are presented in FIG. 9.

Powder XRD data was collected as per the general XRD procedure described herein. The plot for Catalyst Material 4.6 is available in FIG. 4. The raw data PXRD plot was used in establishing the range of the peak intensities presented in Table 23.

PSD analysis results are presented in Table 24.

Catalyst Material 4.6 was then submitted for MRU testing. The results are presented in Tables 28 and 29.

Example 33: Synthesis of Catalyst Material 4.7

Catalyst 3.18 (1.51 g), VERSAL™ 250 alumina (UOP) (1.50 g), goethite (2.09 g), and distilled water (approximately 20 mL) were added to a 100 mL beaker which formed a purple suspension. Next, the beaker was clamped into an oil bath at approximately 100° C. and stirred at approximately 100 rpm until the mixture took on a dark green paste-like consistency, which took approximately 4 hours. The reaction mixture was stirred using an electronic overhead stirrer equipped with a half inch Teflon agitator blade and glass stir shaft. The beaker was then removed from the oil bath and placed in an oven at approximately 90° C. to dry for approximately 18 hours. Afterwards, the golden-brown powder was crushed up and heated in an air muffle furnace at 350° C. for 2 hours with a ramp time of 0.5 hours. This yielded a merlot red catalyst material, Catalyst Material 4.7 (4.54 g).

Catalyst Material 4.7 was analyzed by ICP-MS using the general ICP-MS procedure described herein using ICP digestion method 3. The ICP-MS results for Catalyst Material 4.7 are presented in Table 21.

Catalyst Material 4.7 was analyzed by EDS as per the general procedure SEM-EDS. Results are presented in Table 22.

Catalyst Material 4.7 was submitted for SEM imaging. The results are presented in FIG. 9.

Powder XRD data was collected as per the general XRD procedure described herein. The plot for Catalyst Material 4.7 is available in FIG. 4. The raw data PXRD plot was used in establishing the range of the peak intensities presented in Table 23.

PSD analysis results are presented in Table 24.

Catalyst Material 4.7 was then submitted for MRU testing. The results are presented in Tables 28 and 29.

Example 34: Synthesis of Catalyst Material 4.8

Catalyst 3.18 (1.26 g), goethite (2.92 g), and distilled water (approximately 20 mL) were charged to a 10 mL beaker which formed an olive-green suspension. Afterwards, the beaker was clamped into an oil bath at approximately 100° C. and stirred at approximately 110 rpm until the mixture took on an olive-green paste-like consistency, which took approximately 1.5 hours. The reaction mixture was stirred using an electronic overhead stirrer equipped with a half inch Teflon agitator blade and glass stir shaft. Next, the beaker was removed from the oil bath and placed in an oven at approximately 90° C. to dry for approximately 18 hours. Subsequently, the olive-green powder was crushed and heated in an air muffle furnace at 350° C. for 2 hours with a ramp time of 0.5 hours. This yielded a merlot red, orange catalyst material, Catalyst Material 4.8 (3.50 g).

Catalyst Material 4.8 was analyzed by ICP-MS using the general ICP-MS procedure described herein using ICP digestion method 3. The ICP-MS results for Catalyst Material 4.8 are presented in Table 21.

Catalyst Material 4.8 was analyzed by EDS as per the general SEM-EDS procedure described herein. The results are presented in Table 22.

Catalyst Material procedure was submitted for SEM imaging. The results are presented in FIG. 9.

Powder XRD data was collected as per the general XRD procedure described herein. The plot for this catalyst is available in FIG. 4. The raw data PXRD plot was used in establishing the range of the peak intensities presented in Table 23.

PSD analysis results are presented in Table 24.

Catalyst Material 4.8 was then submitted for MRU testing. The results are presented in Tables 28 and 29.

Example 35: Synthesis of Catalyst Material 4.9

Catalyst 3.18 (3.29 g), goethite (0.82 g), VERSAL™ 250 alumina (UOP) (6.17 g), and distilled water (25 mL) was charged to a 100 mL beaker. Next, the beaker was clamped in an oil bath, an overhead agitator assembly was set up using a half inch stir blade and a glass sir shaft. Following the setup, the oil bath was heated to 100° C. and the agitator was set to 80 rpm. Subsequently, the suspension was heated and stirred until it became a paste (approximately 1.5 hours). Next, the paste (22.6713 g) was dried in an oven at 90° C. overnight. The resulting powder was air calcined in a muffle furnace at 350° C. for 2.5 hours with a ramp time of 1 hour. After calcination, 9.07 g of Catalyst Material 4.9 was recovered.

Catalyst Material 4.9 was analyzed by EDS as per the general SEM-EDS procedure described herein. The results are presented in Table 22.

Catalyst Material 4.9 was submitted for SEM imaging. The results are presented in FIG. 9.

Powder XRD data was collected as per the general XRD procedure described herein. The plot for this catalyst is available in FIG. 4. The raw data PXRD plot was used in establishing the range of the peak intensities presented in Table 23.

PSD analysis results are presented in Table 24.

Catalyst Material 4.9 was then submitted for MRU testing. The results are presented in Tables 28 and 29.

ICP-MS Analysis of Catalyst Materials 4.1, 4.2, 4.5, 4.7, and 4.8

The results for the ICP-MS analysis of Catalyst Materials 4.1, 4.5, 4.7, and 4.8 are present in Table 21.

TABLE 21

| | Starting Material Ratios (wt. %) | | | Measured Concentration (ppm) | | | | |
|---|---|---|---|---|---|---|---|---|
| | | α- | γ- | | | | | |
| Sample | Catalyst | FeOOH | AlO(OH) | Mo | V | Fe | Al | Metal Molar Ratio |
| Catalyst Material 4.1 | 32 | 8 | 60 | 216000 | 36720 | 49790 | 238900 | $Mo_1V_{0.32}Fe_{0.40}Al_{3.93}$ |
| Catalyst Material 4.5 | 32 | 8 | 60 | 199200 | 39820 | 52220 | 239900 | $Mo_1V_{0.38}Fe_{0.45}Al_{4.28}$ |
| Catalyst Material 4.7 | 30 | 40 | 30 | 181900 | 37910 | 267700 | 109100 | $Mo_1V_{0.39}Fe_{2.53}Al_{2.13}$ |
| Catalyst Material 4.8 | 30 | 70 | 0 | 169500 | 34970 | 446400 | — | $Mo_1V_{0.39}Fe_{4.52}$ |

EDS Analysis of Catalyst 3.18 and Catalyst Materials 4.1, 4.2, and 4.6-4.9

The EDS analysis of Catalyst 3.18 and Catalyst Materials 4.6-4.9 are presented in Table 22.

TABLE 22

| | Starting Material Ratios (wt. %) | | | Elemental Mass % | | | | |
|---|---|---|---|---|---|---|---|---|
| | | α- | γ- | | | | | |
| Sample | Catalyst | FeOOH | AlO(OH) | Mo | V | Fe | Al | Metal Molar Ratio |
| Catalyst 3.18 | 100 | 0 | 0 | 52.55 | 12.27 | 0.03 | 0.22 | $Mo_1V_{0.44}$ |
| Catalyst Material 4.1 | 32 | 8 | 60 | 19.12 | 4.22 | 5.85 | 20.08 | $Mo_1V_{0.42}Fe_{0.53}Al_{3.73}$ |
| Catalyst Material 4.2 | 40 | 0 | 60 | 23.82 | 5.28 | 0.06 | 20.11 | $Mo_1V_{0.42}Al_{3.00}$ |
| Catalyst Material 4.6 | 30 | 0 | 70 | 15.73 | 3.77 | 0.04 | 26.95 | $Mo_1V_{0.45}Al_{6.09}$ |
| Catalyst Material 4.7 | 30 | 40 | 30 | 16.85 | 3.74 | 25.04 | 10.61 | $Mo_1V_{0.42}Fe_{2.55}Al_{2.24}$ |
| Catalyst Material 4.8 | 30 | 70 | 0 | 15.80 | 3.58 | 43.83 | 0.21 | $Mo_1V_{0.43}Fe_{4.77}$ |
| Catalyst Material 4.9 | 32 | 8 | 60 | 17.66 | 4.04 | 5.07 | 22.26 | $Mo_1V_{0.43}Fe_{0.49}Al_{4.48}$ |

PXRD Analysis of Catalyst 3.18 and Catalyst Materials 4.1-4.2 and 4.6-4.9

Table 23 presents the reflection angles and corresponding intensity for Catalyst 3.18 and Catalyst Materials 4.1-4.2 and 4.6-4.9. A plot correlating to peak numbers is presented in FIG. 4.

TABLE 23

| Peak Number | Min Angle | Max Angle | Min Intensity | Max Intensity |
|---|---|---|---|---|
| 1 | 6.604 | 6.736 | 23.2% | 102.6% |
| 2 | 7.814 | 7.946 | 32.1% | 138.1% |
| 3 | 8.958 | 9.112 | 32.6% | 95.8% |
| 4 | 10.784 | 10.938 | 22.6% | 64.7% |
| 5 | 12.984 | 13.138 | 27.6% | 56.4% |
| 6 | 13.292 | 13.424 | 25.6% | 52.5% |
| 7 | 13.952 | 14.084 | 24.9% | 48.3% |
| 8 | 22.114 | 22.246 | 100.0% | 100.0% |
| 9 | 23.038 | 23.192 | 19.7% | 37.3% |
| 10 | 23.456 | 23.610 | 21.5% | 40.8% |
| 11 | 23.808 | 23.962 | 20.7% | 52.2% |
| 12 | 25.304 | 25.458 | 24.8% | 45.0% |
| 13 | 25.766 | 25.898 | 20.3% | 37.0% |
| 14 | 26.250 | 26.382 | 30.1% | 56.5% |
| 15 | 26.690 | 26.822 | 34.2% | 73.2% |
| 16 | 27.240 | 27.350 | 49.3% | 110.6% |
| 17 | 27.900 | 28.054 | 26.9% | 39.8% |
| 18 | 28.164 | 28.296 | 36.6% | 62.5% |

TABLE 23-continued

| Peak Number | Min Angle | Max Angle | Min Intensity | Max Intensity |
|---|---|---|---|---|
| 19 | 28.714 | 28.868 | 22.5% | 36.4% |
| 20 | 29.220 | 29.374 | 28.4% | 53.5% |
| 21 | 29.814 | 29.990 | 21.9% | 39.6% |
| 22 | 30.562 | 30.694 | 22.0% | 46.0% |
| 23 | 31.332 | 31.552 | 24.0% | 49.3% |
| 24 | 31.838 | 31.992 | 19.4% | 45.4% |
| 25 | 32.762 | 33.114 | 17.9% | 85.5% |
| 26 | 33.950 | 34.192 | 17.4% | 42.7% |
| 27 | 34.566 | 34.720 | 17.0% | 37.9% |
| 28 | 35.402 | 35.600 | 21.7% | 118.6% |
| 29 | 36.128 | 36.282 | 17.6% | 37.4% |
| 30 | 36.920 | 37.074 | 17.6% | 33.7% |
| 31 | 37.470 | 37.558 | 17.5% | 32.4% |
| 32 | 38.086 | 38.240 | 17.5% | 32.4% |
| 33 | 38.702 | 38.878 | 18.4% | 32.7% |
| 34 | 40.748 | 41.122 | 14.9% | 72.3% |
| 35 | 42.882 | 43.014 | 14.9% | 32.8% |
| 36 | 45.104 | 45.302 | 21.3% | 35.8% |
| 37 | 48.140 | 48.338 | 19.0% | 34.6% |
| 38 | 48.580 | 48.756 | 19.4% | 36.6% |
| 39 | 49.196 | 49.394 | 18.1% | 47.3% |
| 40 | 51.330 | 51.484 | 20.1% | 43.2% |
| 41 | 51.880 | 52.034 | 16.4% | 38.2% |
| 42 | 52.518 | 52.694 | 16.7% | 36.0% |
| 43 | 53.882 | 54.124 | 13.7% | 79.1% |
| 44 | 56.566 | 56.720 | 15.6% | 36.2% |
| 45 | 57.050 | 57.248 | 14.3% | 35.4% |

TABLE 23-continued

| Peak Number | Min Angle | Max Angle | Min Intensity | Max Intensity |
|---|---|---|---|---|
| 46 | 62.374 | 62.616 | 12.3% | 41.1% |
| 47 | 63.980 | 64.420 | 13.0% | 57.3% |

PSD Analysis of Catalyst 3.18 and Catalyst Materials 4.1, 4.6-4.9

Table 24 presents the statistical data from the PSD analysis of Catalyst 3.18 and Catalyst Materials 4.6-4.9.

TABLE 24

| Sample | Catalyst 3.18 | Catalyst Material 4.1 | Catalyst Material 4.6 | Catalyst Material 4.7 | Catalyst Material 4.8 | Catalyst Material 4.9 |
|---|---|---|---|---|---|---|
| Maximum | 240.40 | 50.73 | 219.20 | 108.70 | 142.80 | 211.10 |
| Minimum | 0.10 | 0.10 | 0.26 | 0.09 | 0.09 | 0.20 |
| Mean | 61.92 | 4.17 | 15.59 | 9.81 | 10.43 | 12.96 |
| Median | 26.77 | 1.71 | 7.91 | 4.02 | 1.01 | 3.45 |
| Mode | 37.64-48.01 | 0.60-0.77 | 6.86-8.75 | 0.98-1.25 | 0.77-0.98 | 0.98-1.25 |
| Range | 240.30 | 50.63 | 218.94 | 108.61 | 142.71 | 210.90 |
| Skewness | 2.03 | 3.19 | 3.73 | 3.02 | 2.69 | 3.91 |
| Kurtosis | 3.42 | 14.87 | 18.58 | 13.14 | 9.22 | 16.63 |
| Standard Deviation | 88.32 | 5.87 | 22.94 | 14.07 | 18.67 | 28.61 |
| D10 | 1.77 | 0.41 | 1.62 | 0.45 | 0.35 | 0.70 |
| D25 (Quartile 1) | 5.72 | 0.70 | 3.35 | 0.87 | 0.57 | 1.22 |
| D50 | 26.77 | 1.71 | 7.91 | 4.02 | 1.01 | 3.45 |
| D75 (Quartile 3) | 70.77 | 5.69 | 17.46 | 14.54 | 13.54 | 9.28 |
| D90 | 202.90 | 11.04 | 36.05 | 25.01 | 35.22 | 28.39 |

BET Analysis of Catalyst 3.18 and Catalyst Materials 4.1-4.2, 4.6-4.8

The results of nitrogen gas adsorption analysis for pore volume and BET surface area analysis for Catalyst 3.18 and Catalyst Materials 4.1-4.2 and 4.6-4.8 are shown in Table 25.

TABLE 25

| Sample | BET Surface Area ($m^2/g$) | Pore Volume ($cm^3/g$) |
|---|---|---|
| Catalyst 3.18 | 6 | 0.02 |
| Catalyst Material 4.2 | 153.0 | 0.32 |
| Catalyst Material 4.1 | 154.0 | 0.32 |
| Catalyst Material 4.6 | 197 | 0.48 |
| Catalyst Material 4.7 | 110 | 0.21 |
| Catalyst Material 4.8 | 71 | 0.07 |

Bulk Density Measurements of Catalyst Materials 4.1-4.2

Table 26 presents the bulk density measurements for Catalyst Material 4.1 and 4.2.

TABLE 26

| Sample | Measurements (g/mL) | Average (g/mL) |
|---|---|---|
| Catalyst Material 4. 1 | 0.9026<br>0.9235<br>0.9339 | 0.9200 |
| Catalyst Material 4.2 | 0.9225<br>0.9676<br>0.9349 | 0.9417 |

Activity and Selectivity for Catalyst and Catalyst Materials

Table 27 presents the MRU results for Catalyst Materials 4.1-4.5.

TABLE 27

| Sample | 35 mol. % Ethane Conversion Temperature (° C.) | Selectivity to Ethylene (mol. %) | MRU Loading Method | Acetic Acid Concentration in Collected Condensate (wt. %) |
|---|---|---|---|---|
| Catalyst Material 4. 1 | 324 | 88 | Method 2 | 14.39 |
| Catalyst Material 4.2 | 323 | 91 | Method 2 | 18.90 |
| Catalyst Material 4.3 | 334 | 89 | Method 1 | 20.00 |

TABLE 27-continued

| Sample | 35 mol. % Ethane Conversion Temperature (° C.) | Selectivity to Ethylene (mol. %) | MRU Loading Method | Acetic Acid Concentration in Collected Condensate (wt. %) |
|---|---|---|---|---|
| Catalyst Material 4.4 | 326 | 87 | Method 2 | 12.80 |
| Catalyst Material 4.5 | 340 | 87 | Method 2 | 13.49-15.60 |

Table 28 presents the MRU results for Catalyst 3.18 and Catalyst Materials 4.6-4.9. during first days of MRU testing.

TABLE 28

| Sample | Length of Run (day) | 35 mol.% Ethane Conversion Temperature at Start of Run (° C.) | Selectivity to Ethylene (mol. %) | MRU Loading Method | Acetic Acid Concentration in Condensate Samples Collected (wt. %) |
|---|---|---|---|---|---|
| Catalyst 3.18 | 1 | 327 | 87 | Method 1 | 17.42 |
| Catalyst Material 4.6 | 1 | 335 | 88 | Method 2 | 15.06 |
| Catalyst Material 4.7 | 4 | 345 | 79 | Method 2 | 9.75 |
| Catalyst Material 4.8 | 1 | 364 | 70 | Method 1 | 5.48 |
| Catalyst Material 4.9 | 1 | 330 | 86 | Method 2 | 14.49 |

Table 29 presents the MRU results for Catalyst 3.18 and Catalyst Materials 4.6-4.9. after several days of MRU testing, illustrating performance changes arising from the catalyst being exposed to the ethylene conversion process.

TABLE 29

| | | Starting Material Ratios (wt. %) | | | Length | Temp. at End | Ethane conversion at end of | Selectivity to Ethylene at end of | Acetic Acid Conc. in Collected |
|---|---|---|---|---|---|---|---|---|---|
| Sample | Molar Formula | Catalyst | α-Fe0OH | γ-AlO(OH) | of Run (days) | of Run (° C.) | run (mol %) | run (mol %) | Condensate (wt. %) |
| Catalyst 3.18 | $Mo_1V_{0.44}$* | 100 | 0 | 0 | 5 | 327 | 38.5 | 89.4 | 17.21 |
| Catalyst Material 4.6 | $Mo_1V_{0.45}Al_{6.09}$* | 30 | 0 | 70 | 3 | 340 | 35.1 | 89.1 | 19.37 |
| Catalyst Material 4.7 | $Mo_1V_{0.39}Fe_{2.53}Al_{2.13}$‡ | 30 | 40 | 30 | 5 | 360 | 35.3-33.9 | 86.0-86.9 | 9.95 |
| Catalyst Material 4.8 | $Mo_1V_{0.39}Fe_{4.52}$‡ | 30 | 70 | 0 | 6 | 367 | 34.3 | 82.1 | 5.69 |
| Catalyst Material 4.9 | $Mo_1V_{0.43}Fe_{0.4}9Al_{4.48}$‡ | 32 | 8 | 60 | 5 | 336 | 35.7 | 89.3 | 14.87 |

*Molar formula as determined by EDS
‡molar formula from ICP-MS

Synthesis of Catalyst Material 5.1

Example 36: Synthesis of Catalyst Material 5.1

Catalyst 1.4 (1.75 g) and Catalyst 3.17 (1.93 g) were combined with 3.6823 g of PB 250 alumina (Alumax) and 1.84 g of goethite in a beaker. The combined solids were dry mixed together, then 60 mL of water was added to create a green suspension. The green suspension was heated in the beaker using a 100° C. oil bath and mixed at 80 rpm using a motor-driven overhead stirring Teflon agitator. After 2.5 hours, the water was evaporated to a smearable paste. The sample was dried in the oven at 90° C. overnight, then calcined at 350° C. for 2.5 hours under air in a muffle furnace. The resulting 8.24 g of red solids were Catalyst Material 5.1.

Catalyst Material 5.1 was analyzed by EDS as per the general SEM-EDS procedure described herein. The results are presented in Table 30.

Powder XRD data was collected as per the general XRD procedure described herein. The plot for Catalyst Material 5.1 is available in FIG. 5. The raw data PXRD plot was used in establishing the range of the peak intensities is presented in Table 31.

Catalyst Material 5.1 was then submitted for MRU testing. The results are presented in Table 32.

EDS Analysis of Catalyst Material 5.1

Table 30 presents the EDS Analysis results for Catalyst Material 5.1.

TABLE 30

| | Starting Material Ratios (wt. %) | | | Elemental Mass % | | | | |
|---|---|---|---|---|---|---|---|---|
| Sample | Catalyst | α-FeOOH | γ-AlO(OH) | Mo | V | Fe | Al | Metal Molar Ratio |
| Catalyst Material 5.1 | 40 | 20 | 40 | 23.07 | 5.12 | 13.51 | 13.08 | $Mo_1V_{0.42}Fe_{1.01}Al_{2.02}$ |

PXRD Analysis of Catalyst Material 5.1

Figure 5:
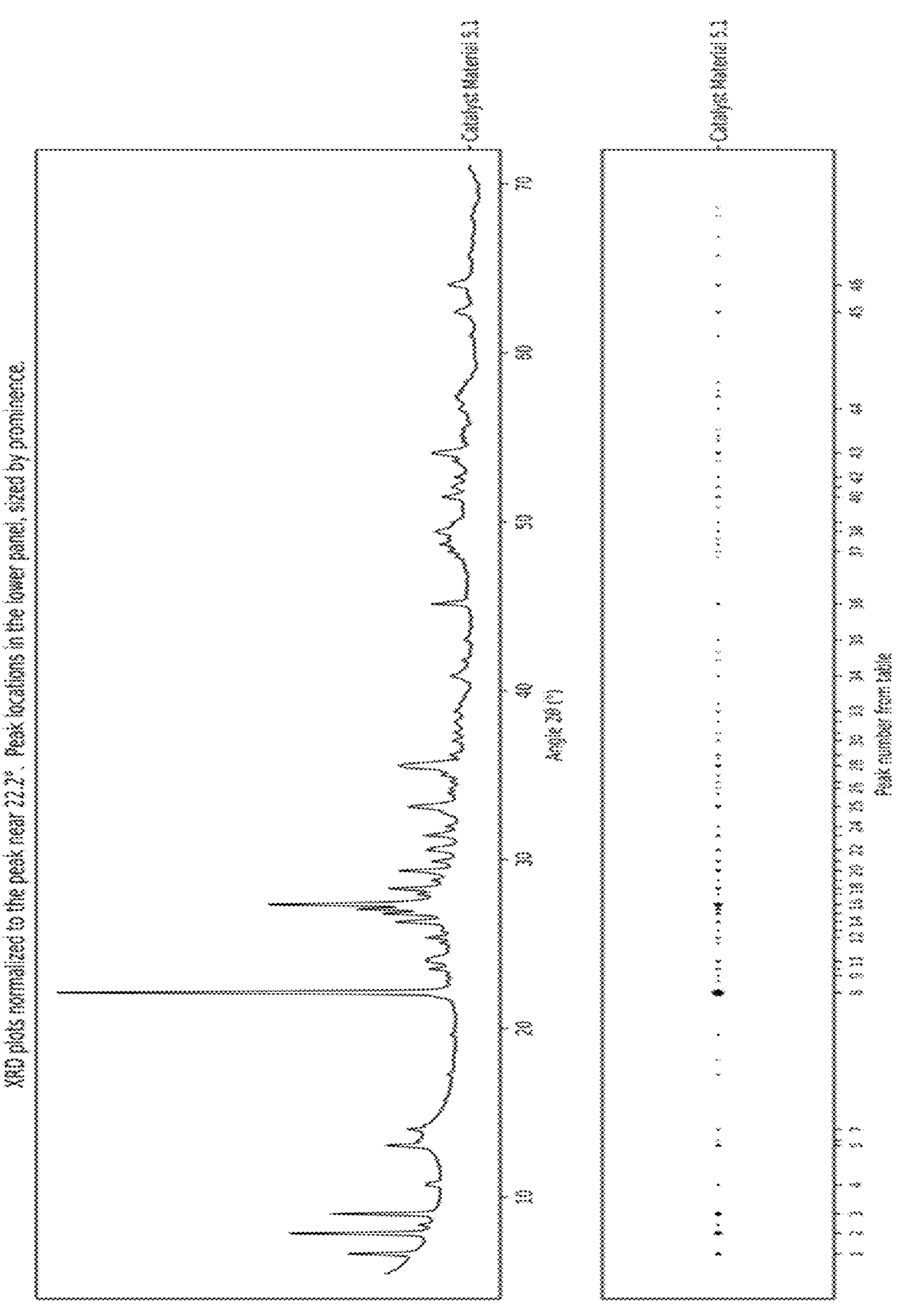
FIG. 5 shows the XRD plot of Catalysts/Catalyst Materials 5.1.

Table 31 presents the reflection angles and corresponding intensity for Catalyst Material 5.1. FIG. 5 is the plot correlating to peak numbers.

TABLE 31

| Peak | Angle | Intensity |
|---|---|---|
| 1 | 6.648 | 43.2% |
| 2 | 7.880 | 54.5% |
| 3 | 9.024 | 46.4% |
| 4 | 10.740 | 28.1% |
| 5 | 13.072 | 35.7% |
| 6 | 13.358 | 29.7% |
| 7 | 14.018 | 31.7% |
| 8 | 22.114 | 100.0% |
| 9 | 23.126 | 24.0% |
| 10 | 23.522 | 27.4% |
| 11 | 23.962 | 28.0% |
| 12 | 25.370 | 28.0% |
| 13 | 25.788 | 25.0% |
| 14 | 26.316 | 33.7% |
| 15 | 26.800 | 36.4% |
| 16 | 27.328 | 58.7% |
| 17 | 27.944 | 29.9% |
| 18 | 28.274 | 35.4% |
| 19 | 28.758 | 26.9% |
| 20 | 29.330 | 33.3% |
| 21 | 29.902 | 26.9% |
| 22 | 30.562 | 27.9% |
| 23 | 31.420 | 28.4% |
| 24 | 31.948 | 24.1% |
| 25 | 33.136 | 31.4% |
| 26 | 34.236 | 23.2% |
| 27 | 34.610 | 23.1% |
| 28 | 35.578 | 33.2% |
| 29 | 36.194 | 23.3% |
| 30 | 37.052 | 22.8% |

TABLE 31-continued

| Peak | Angle | Intensity |
|---|---|---|
| 31 | 37.492 | 22.5% |
| 32 | 38.174 | 22.5% |
| 33 | 38.768 | 22.5% |
| 34 | 40.858 | 23.2% |
| 35 | 43.014 | 20.4% |
| 36 | 45.148 | 27.0% |
| 37 | 48.250 | 23.6% |
| 38 | 49.438 | 26.4% |
| 39 | 49.966 | 22.9% |
| 40 | 51.462 | 25.0% |
| 41 | 52.056 | 23.0% |
| 42 | 52.628 | 22.4% |
| 43 | 54.058 | 26.9% |
| 44 | 56.698 | 21.7% |
| 45 | 62.418 | 22.4% |
| 46 | 64.002 | 23.6% |

Activity and Selectivity for Catalysts 1.4 and 3.17, and Catalyst Material 5.1

Table 32 presents the MRU results for Catalysts 1.4 and 3.17, and Catalyst Material 5.1.

TABLE 32

| Sample | 35 mol. % Ethane Conversion Temperature (° C.) | Selectivity to Ethylene (mol. %) | MRU Loading Method | Acetic Acid Concentration in Collected Condensate (wt. %) |
|---|---|---|---|---|
| Catalyst 1.4 | 348 | 80 | Method 1 | — |
| Catalyst 3.17 | 348 | 79 | Method 1 | — |
| Catalyst Material 5.1 | 350 | 87 | Method 2 | 14.2 |

Amorphous Content Analysis and XRD Phase Fitting

Table 33 presents the amorphous content analysis for Catalyst 1.1, Catalyst 1.4-1.6, Catalyst 3.7-3.12, Catalyst 3.15-3.18, Catalyst Material 4.1-4.2, Catalyst Material 4.6-4.9, Catalyst Material 5.1.

TABLE 33

| | Fitted Phases | | | | | |
|---|---|---|---|---|---|---|
| Sample | M1 Phase (wt. %) | Other Mixed Metal Oxide Phases (wt. %) | Fe Phases (wt. %) | Al Phases (wt. %) | Amorphous Content (wt. %) | Total (wt. %) |
| Catalyst 1.1 | 46.4 | 10.2 | 0.0 | 0.0 | 43.4 | 100.0 |
| Catalyst 1.4 | 56.1 | 8.7 | 0.0 | 0.0 | 35.2 | 100.0 |
| Catalyst 1.5 | 51.0 | 5.7 | 0.0 | 0.0 | 43.3 | 100.0 |
| Catalyst 1.6 | 42.2 | 0.9 | 0.7 | 0.2 | 55.9 | 99.9 |
| Catalysts 3.7 | 55.8 | 7.3 | 0.0 | 0.0 | 37.8 | 100.9 |
| Catalysts 3.8 | 45.5 | 3.1 | 0.0 | 0.0 | 51.4 | 100.0 |
| Catalysts 3.9 | 53.5 | 3.4 | 0.0 | 0.0 | 43.1 | 100.0 |
| Catalysts 3.10 | 53.3 | 4.7 | 0.0 | 0.0 | 42.0 | 100.0 |
| Catalysts 3.11 | 47.6 | 25.7 | 0.0 | 1.0 | 25.7 | 100.0 |
| Catalysts 3.12 | 50.9 | 0.9 | 0.0 | 0.0 | 48.2 | 100.0 |
| Catalysts 3.15 | 62.5 | 4.5 | 0.0 | 0.0 | 33.0 | 100.0 |
| Catalysts 3.16 | 31.9 | 23.0 | 0.0 | 0.0 | 45.0 | 99.9 |
| Catalysts 3.17 | 27.36 | 2.17 | 0.09 | 0.15 | 70.26 | 100.03 |
| Catalysts 3.18 | 67.3 | 8.5 | 0.00 | 0.1 | 24.3 | 100.2 |
| Catalyst Materials 4.1 | 14.5 | 1.0 | 3.2 | 26.0 | 55.4 | 100.1 |
| Catalyst Materials 4.2 | 36.1 | 1.0 | 0.0 | 1.2 | 61.8 | 100.1 |
| Catalyst Materials 4.6 | 16.2 | 3.0 | 0.0 | 24.0 | 56.8 | 100.0 |
| Catalyst Materials 4.7 | 23.5 | 5.9 | 28.0 | 16.7 | 25.8 | 99.9 |
| Catalyst Materials 4.8 | 22.9 | 6.2 | 49.3 | 1.1 | 20.5 | 100 |
| Catalyst Materials 4.9 | 17.1 | 1.2 | 2.4 | 15.3 | 63.9 | 99.9 |
| Catalyst Materials 5.1 | 27.2 | 1.2 | 15.1 | 26.5 | 29.9 | 99.9 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

INDUSTRIAL APPLICABILITY

Catalyst materials for the oxidative dehydrogenation of alkanes such as ethane.

The invention claimed is:

1. A catalyst material, consisting of:
molybdenum;
vanadium;
oxygen; and
iron,
wherein:
a molar ratio of molybdenum to vanadium is from 1:0.25 to 1:0.50;
a molar ratio of molybdenum to iron is from 1:0.25 to 1:5.5; and
oxygen is present at least in an amount to satisfy the valency of any present metal oxides; and
wherein the catalyst material has a Brunauer-Emmett-Teller (BET) surface area from 35 $m^2/g$ to 250 $m^2/g$ as determined by a nitrogen physisorption analysis.

2. The catalyst material of claim 1, wherein the molar ratio of molybdenum to vanadium is from 1:0.30 to 1:0.45.

3. The catalyst material of claim 1, wherein the molar ratio of molybdenum to iron is from 1:3 to 1:5.5.

4. The catalyst material of claim 1, wherein at least a portion of the iron comprises at least one member selected from the group consisting of an iron oxide and an iron oxide hydroxide.

5. The catalyst material of claim 1, wherein at least a portion of the iron comprises at least one iron selected from the group consisting of hematite (α-$Fe_2O_3$), maghemite (γ-$Fe_2O_3$), and magnetite ($Fe_3O_4$).

6. The catalyst material of claim 1, wherein the catalyst material has at least ten powder X-ray diffraction (PXRD) peaks (2θ degrees) chosen from 6.7±0.2, 7.9±0.2, 9.0±0.2, 10.9±0.2, 13.1±0.2, 14.0±0.2, 22.1±0.2, 26.3±0.2, 26.8±0.2, 27.3±0.2, 28.3±0.2, 29.3±0.2, 30.6±0.2, 31.5±0.2, 33.1±0.2, 35.6±0.2, 40.9±0.2, 45.2=0.2, 54.1±0.2, and 64.0=0.2, wherein the PXRD is obtained using CuKα radiation.

7. The catalyst material of claim 1, wherein the catalyst material has at least five powder X-ray diffraction (PXRD) peaks (2θ degrees) chosen from 6.7±0.2, 7.9±0.2, 9.0±0.2, 10.9±0.2, 13.1±0.2, and 22.1±0.2 wherein the PXRD is obtained using CuKα radiation.

8. The catalyst material of claim 1, wherein the catalyst material has a pore volume from 0.03 $cm^3/g$ to 0.60 $cm^3/g$ as determined by a nitrogen physisorption analysis with a Barrett-Joyner-Halenda (BJH) model.

9. The catalyst material of claim 1, wherein the catalyst material is an oxidative dehydrogenation catalyst material.

10. A catalyst material, consisting of:
molybdenum;
vanadium;
oxygen; and
iron,
wherein:
a molar ratio of molybdenum to vanadium is from 1:0.25 to 1:0.50;
a molar ratio of molybdenum to iron is from 1:3 to 1:5.5; and
oxygen is present at least in an amount to satisfy the valency of any present metal oxides; and
wherein the catalyst material is an oxidative dehydrogenation catalyst material for the oxidative dehydrogenation of an alkane.

11. The catalyst material of claim 10, wherein at least a portion of the iron comprises at least one member selected from the group consisting of an iron oxide and an iron oxide hydroxide.

12. The catalyst material of claim 10, wherein at least a portion of the iron comprises at least one iron selected from the group consisting of hematite (α-$Fe_2O_3$), maghemite (γ-$Fe_2O_3$), and magnetite ($Fe_3O_4$).

13. The catalyst material of claim 10, wherein the catalyst material has a Brunauer-Emmett-Teller (BET) surface area from 35 $m^2/g$ to 250 $m^2/g$ as determined by a nitrogen physisorption analysis.

* * * * *